US012286478B2

(12) United States Patent
Langermann et al.

(10) Patent No.: US 12,286,478 B2
(45) Date of Patent: Apr. 29, 2025

(54) B7-H4 ANTIBODIES AND METHODS OF USE THEREOF

(71) Applicant: NextCure, Inc., Beltsville, MD (US)

(72) Inventors: Solomon Langermann, Baltimore, MD (US); Dallas Benjamin Flies, Rockville, MD (US); Linda Liu, Clarksville, MD (US)

(73) Assignee: NextCure, Inc., Beltsville, MD (US)

( * ) Notice: Subject to any disclaimer, the term of this patent is extended or adjusted under 35 U.S.C. 154(b) by 1200 days.

(21) Appl. No.: 16/964,133

(22) PCT Filed: Jan. 23, 2019

(86) PCT No.: PCT/US2019/014748
§ 371 (c)(1),
(2) Date: Mar. 31, 2021

(87) PCT Pub. No.: WO2019/147670
PCT Pub. Date: Aug. 1, 2019

(65) Prior Publication Data
US 2021/0032346 A1    Feb. 4, 2021

Related U.S. Application Data

(60) Provisional application No. 62/620,545, filed on Jan. 23, 2018.

(51) Int. Cl.
*C07K 16/28*     (2006.01)
*C07K 14/705*    (2006.01)

(52) U.S. Cl.
CPC .... *C07K 16/2827* (2013.01); *C07K 14/70532* (2013.01); *C07K 2317/31* (2013.01); *C07K 2317/51* (2013.01); *C07K 2317/515* (2013.01); *C07K 2317/565* (2013.01); *C07K 2317/732* (2013.01)

(58) Field of Classification Search
CPC .......... C07K 16/2827; C07K 14/70532; C07K 2317/31; C07K 2317/51; C07K 2317/515; C07K 2317/565; C07K 2317/732
See application file for complete search history.

(56) References Cited

U.S. PATENT DOCUMENTS

| | | | |
|---|---|---|---|
| 2009/0087416 | A1 | 4/2009 | Chen |
| 2011/0085970 | A1 | 4/2011 | Terrett et al. |
| 2013/0156770 | A1 | 6/2013 | Kufer et al. |
| 2014/0356364 | A1 | 12/2014 | Langermann et al. |
| 2015/0315275 | A1 | 11/2015 | Langermann et al. |
| 2016/0017040 | A1 | 1/2016 | Leong et al. |
| 2017/0334999 | A1* | 11/2017 | Sathyanarayanan .......... C07K 16/3015 |
| 2023/0107639 | A1 | 4/2023 | Monroe et al. |

FOREIGN PATENT DOCUMENTS

| | | |
|---|---|---|
| CN | 101951959 A | 1/2011 |
| CN | 104955475 A | 9/2015 |
| CN | 105189552 A | 12/2015 |
| CN | 107106679 A | 8/2017 |
| EP | 3743447 A1 | 12/2020 |
| JP | 2014-531409 A | 11/2014 |
| RU | 2015129551 A | 1/2017 |
| RU | 2020127875 A | 2/2022 |
| WO | 2009/073533 A2 | 6/2009 |
| WO | 2016/070001 A1 | 5/2016 |
| WO | 2019/147670 A1 | 8/2019 |

OTHER PUBLICATIONS

Qian, Y., et al., "Development of a Novel Monoclonal Antibody to B7-H4: Characterization and Biological Activity", Eur. J. Med. Res., 16: 295-302 (2011).
Supplementary European Search Report received on Oct. 6, 2021 regarding EP 19743902.9 (7 pages).
Intention to Grant received for European Application No. 19743902. 9, mailed on Oct. 6, 2023, 2 pages.
Office Action received for Chinese Patent Application No. 201980021260.8, mailed on Oct. 31, 2023, 16 pages (10 pages of English Translation and 6 pages of Original Document).
Office Action received for Japanese Patent Application No. 2020-561589, mailed on Nov. 27, 2023, 6 pages (3 pages of English Translation and 3 pages of Original Document).
Office Action received for Japanese Patent Application No. 2020-561589, mailed on Mar. 1, 2023, 6 pages (3 pages of English Translation and 3 pages of Original Document).
Mariuzza, "The structural basis of antigen-antibody recognition", Ann. Rev. Biophys. Biophys. Chem., vol. 16, 1987, pp. 139-159.
Office Action received for Russian Patent Application No. 2020127875, mailed on Dec. 9, 2022, 14 pages (6 pages of English Translation and 8 pages of Original Document).
Search Report received for Russian Patent Application No. 2020127875, mailed on Dec. 9, 2022, 4 pages (2 pages of English Translation and 2 pages of Original Document).
Office Action received for Russian Patent Application No. 2020127875, mailed on Jul. 12, 2022, 13 pages (6 pages of English Translation and 7 pages of Original Document).
Leong, S. R., et al., "An Anti-B7-H4 Antibody-Drug Conjugate for the Treatment of Breast Cancer", Molecular Pharmaceutics, vol. 12, Apr. 8, 2015, pp. 1717-172.

(Continued)

*Primary Examiner* — Mark Halvorson
*Assistant Examiner* — Dennis J Sullivan
(74) *Attorney, Agent, or Firm* — Smith, Gambrell & Russell, LLP; Judy Jarecki-Black; Sharon Ngwenya

(57) ABSTRACT

Compositions and methods of use thereof for modulating B7-H4 are provided. For example, immunomodulatory agents are provided that reduce B7-H4 expression, ligand binding, crosslinking, negative signaling, or a combination thereof. Such agents can be used to increase an immune response in a subject in need thereof. Immunomodulatory agents are also provided that increase B7-H4 expression, ligand binding, crosslinking, negative signaling, or a combination thereof. Such agents can be used to reduce an immune response in a subject in need thereof.

16 Claims, No Drawings
Specification includes a Sequence Listing.

(56) References Cited

OTHER PUBLICATIONS

Second Office Action received for Chinese Patent Application No. 201980021260.8, mailed on Apr. 3, 2024, 8 pages (5 pages of English Translation and 3 pages of Original Document).
Office Action received for Australian Patent Application No. 2019211326, mailed on Nov. 6, 2024, 7 pages.
Office Action received for Korean Patent Application No. 10-2020-7024024, mailed on Nov. 15, 2024, 8 pages (4 pages of English Translation and 4 pages of Original Document).

\* cited by examiner

SEQUENCE LISTING

<160> NUMBER OF SEQ ID NOS: 131

<210> SEQ ID NO 1
<211> LENGTH: 282
<212> TYPE: PRT
<213> ORGANISM: Homo sapiens

<400> SEQUENCE: 1

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
                20                  25                  30

Gly Arg His Ser Ile Thr Val Thr Thr Val Ala Ser Ala Gly Asn Ile
            35                  40                  45

Gly Glu Asp Gly Ile Leu Ser Cys Thr Phe Glu Pro Asp Ile Lys Leu
        50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
        275                 280

<210> SEQ ID NO 2
<211> LENGTH: 283
<212> TYPE: PRT
<213> ORGANISM: Mus musculus

<400> SEQUENCE: 2

Met Ala Ser Leu Gly Gln Ile Ile Phe Trp Ser Ile Ile Asn Ile Ile
1               5                   10                  15

Ile Ile Leu Ala Gly Ala Ile Ala Leu Ile Ile Gly Phe Gly Ile Ser
            20                  25                  30

Gly Lys His Phe Ile Thr Val Thr Thr Phe Thr Ser Ala Gly Asn Ile
        35                  40                  45

Gly Glu Asp Gly Thr Leu Ser Cys Thr Phe Glu Pro Asp Ile Lys Leu
    50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95

Phe Arg Gly Arg Thr Ala Val Phe Ala Asp Gln Val Val Gly Asn
            100                 105                 110

Ala Ser Leu Arg Leu Lys Asn Val Gln Leu Thr Asp Ala Gly Thr Tyr
        115                 120                 125

Thr Cys Tyr Ile Arg Thr Ser Lys Gly Lys Gly Asn Ala Asn Leu Glu
130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
                245                 250                 255

Gly Pro Ser Pro Cys Val Phe Ser Ala Phe Val Ala Gly Trp Ala
            260                 265                 270

Leu Leu Ser Leu Ser Cys Cys Leu Met Leu Arg
        275                 280

<210> SEQ ID NO 3
<211> LENGTH: 107
<212> TYPE: PRT
<213> ORGANISM: Mus musculus

<400> SEQUENCE: 3

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Arg Thr Ala
            20                  25                  30

Val Ala Trp Tyr Gln Gln Lys Pro Gly Gln Ser Pro Lys Leu Leu Ile
        35                  40                  45

```
Tyr Ser Thr Ser Tyr Arg Tyr Thr Gly Val Pro Asp Arg Phe Thr Gly
            50                  55                  60

Ser Gly Ser Gly Thr Glu Phe Thr Phe Thr Ile Ser Ser Val Gln Ala
 65                  70                  75                  80

Glu Asp Leu Ala Val Tyr Tyr Cys Gln Gln Tyr Tyr Val Thr Pro Leu
                 85                  90                  95

Thr Phe Gly Ala Gly Thr Lys Leu Glu Leu Lys
            100                 105

<210> SEQ ID NO 4
<211> LENGTH: 11
<212> TYPE: PRT
<213> ORGANISM: Mus musculus

<400> SEQUENCE: 4

Lys Ala Ser Gln Asp Val Arg Thr Ala Val Ala
1               5                   10

<210> SEQ ID NO 5
<211> LENGTH: 7
<212> TYPE: PRT
<213> ORGANISM: Mus musculus

<400> SEQUENCE: 5

Ser Thr Ser Tyr Arg Tyr Thr
1               5

<210> SEQ ID NO 6
<211> LENGTH: 9
<212> TYPE: PRT
<213> ORGANISM: Mus musculus

<400> SEQUENCE: 6

Gln Gln Tyr Tyr Val Thr Pro Leu Thr
1               5

<210> SEQ ID NO 7
<211> LENGTH: 321
<212> TYPE: DNA
<213> ORGANISM: Mus musculus

<400> SEQUENCE: 7
gacattgtga tgacccagtc tcacaaattc atgtccacat cagtaggaga cagggtcagt      60
atcacctgca aggccagtca ggatgtgaga actgctgtag cctggtatca acagaaacca     120
ggacaatctc ctaaactact gatttactcg acatcctacc ggtacactgg agtccctgat     180
cgcttcactg gcagtggatc tgggacggaa ttcactttca ccatcagcag tgtgcaggct     240
gaagacctgg cagtttatta ctgtcagcaa tattatgtta ctccgctcac gttcggtgct     300
gggaccaagc tggagctgaa a                                                321

<210> SEQ ID NO 8
<211> LENGTH: 117
<212> TYPE: PRT
<213> ORGANISM: Mus musculus

<400> SEQUENCE: 8

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
                20                  25                  30
```

Trp Met His Trp Ile Lys Gln Arg Pro Gly Gln Gly Leu Glu Trp Ile
             35                  40                  45

Gly Ala Ile Tyr Pro Gly Asn Ser Asp Thr Lys Tyr Asn Gln Lys Phe
         50                  55                  60

Lys Asp Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                 85                  90                  95

Thr Ser Thr Val Arg Asn Val Met Asp Tyr Trp Gly Gln Gly Thr Ser
            100                 105                 110

Val Thr Val Ser Ser
        115

<210> SEQ ID NO 9
<211> LENGTH: 5
<212> TYPE: PRT
<213> ORGANISM: Mus musculus

<400> SEQUENCE: 9

Ser Tyr Trp Met His
1               5

<210> SEQ ID NO 10
<211> LENGTH: 18
<212> TYPE: PRT
<213> ORGANISM: Mus musculus

<400> SEQUENCE: 10

Ala Ile Tyr Pro Gly Asn Ser Asp Thr Lys Tyr Asn Gln Lys Phe Lys
1               5                   10                  15

Asp Lys

<210> SEQ ID NO 11
<211> LENGTH: 8
<212> TYPE: PRT
<213> ORGANISM: Mus musculus

<400> SEQUENCE: 11

Thr Val Arg Asn Val Met Asp Tyr
1               5

<210> SEQ ID NO 12
<211> LENGTH: 351
<212> TYPE: DNA
<213> ORGANISM: Mus musculus

<400> SEQUENCE: 12
gaggttcagc tccagcagtc tgggactgtg ctggcaaggc ctggggcttc agtgaagatg    60
tcctgcaagg cttctggcta cacctttacc agctactgga tgcactggat aaaacagagg   120
cctggacagg gtctggaatg gattggcgct atttatcctg gaaatagtga tactaaatac   180
aaccagaagt tcaaggacaa ggccaaactg actgcagtca catctgccag cactgcctac   240
atggagctca gcagcctgac aaatgaggac tctgcggtct attactgtac atctacggta   300
cggaatgtta tggactactg gggtcaagga acctcagtca ccgtctcctc a            351

<210> SEQ ID NO 13
<211> LENGTH: 107
<212> TYPE: PRT
<213> ORGANISM: Mus musculus

<400> SEQUENCE: 13

Glu Ile Gln Met Thr Gln Ser Pro Ser Ser Met Ser Ala Ser Leu Gly
1               5                   10                  15

Asp Arg Ile Thr Ile Thr Cys Gln Ala Thr Gln Asp Ile Val Lys Ser
            20                  25                  30

Leu Asn Trp Tyr Gln Gln Lys Pro Gly Lys Pro Ser Phe Leu Ile
        35                  40                  45

Tyr Tyr Thr Ala Gln Leu Ala Glu Gly Val Pro Ser Arg Phe Ser Gly
50                  55                  60

Ser Gly Ser Gly Ser Asp Tyr Ser Leu Thr Ile Ser Asn Leu Glu Ser
65                  70                  75                  80

Glu Asp Phe Ala Asp Tyr Tyr Cys Leu Gln Phe Tyr Glu Phe Pro Pro
                85                  90                  95

Thr Phe Gly Gly Gly Thr Lys Leu Glu Ile Lys
            100                 105

<210> SEQ ID NO 14
<211> LENGTH: 11
<212> TYPE: PRT
<213> ORGANISM: Mus musculus

<400> SEQUENCE: 14

Gln Ala Thr Gln Asp Ile Val Lys Ser Leu Asn
1               5                   10

<210> SEQ ID NO 15
<211> LENGTH: 7
<212> TYPE: PRT
<213> ORGANISM: Mus musculus

<400> SEQUENCE: 15

Tyr Thr Ala Gln Leu Ala Glu
1               5

<210> SEQ ID NO 16
<211> LENGTH: 9
<212> TYPE: PRT
<213> ORGANISM: Mus musculus

<400> SEQUENCE: 16

Leu Gln Phe Tyr Glu Phe Pro Pro Thr
1               5

<210> SEQ ID NO 17
<211> LENGTH: 321
<212> TYPE: DNA
<213> ORGANISM: Mus musculus

<400> SEQUENCE: 17
gaaatccaga tgacccagtc tccatcctct atgtctgcat ctctgggaga cagaataacc      60
atcacttgcc aggcaactca agacattgtt aagagtttaa actggtatca acaaaaacca     120
gggaaacccc cttcattcct gatctattat acagctcaac tggcagaagg ggtcccatca     180
aggttcagtg gcagtgggtc tgggtcagac tattctctga caatcagcaa cctggagtct     240
gaagattttg cagactatta ctgtctacag ttttatgagt ttcctccgac gttcggtgga     300
ggcaccaagc tggaaatcaa a                                                321

<210> SEQ ID NO 18

```
<211> LENGTH: 107
<212> TYPE: PRT
<213> ORGANISM: Mus musculus

<400> SEQUENCE: 18

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65              70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
            100                 105

<210> SEQ ID NO 19
<211> LENGTH: 107
<212> TYPE: PRT
<213> ORGANISM: Artificial Sequence
<220> FEATURE:
<223> OTHER INFORMATION: Synthetic

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Gln Ala Thr Gln Asp Ile Val Lys Ser
            20                  25                  30

Leu Asn Trp Tyr Gln Gln Lys Pro Gly Lys Pro Pro Lys Phe Leu Ile
        35                  40                  45

Tyr Tyr Thr Ala Gln Leu Ala Glu Gly Val Pro Ser Arg Phe Ser Gly
    50                  55                  60

Ser Gly Ser Gly Thr Asp Tyr Thr Leu Thr Ile Ser Ser Leu Gln Ser
65              70                  75                  80

Glu Asp Phe Ala Thr Tyr Tyr Cys Leu Gln Phe Tyr Glu Phe Pro Pro
            85                  90                  95

Thr Phe Gly Gly Gly Thr Lys Val Glu Ile Lys
            100                 105

<210> SEQ ID NO 20
<211> LENGTH: 107
<212> TYPE: PRT
<213> ORGANISM: Artificial Sequence
<220> FEATURE:
<223> OTHER INFORMATION: Synthetic

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Gln Ala Thr Gln Asp Ile Val Lys Ser
            20                  25                  30

Leu Asn Trp Tyr Gln Gln Lys Pro Gly Lys Pro Pro Lys Phe Leu Ile
        35                  40                  45

Tyr Tyr Thr Ala Gln Leu Ala Glu Gly Val Pro Ser Arg Phe Ser Gly
    50                  55                  60
```

```
Ser Gly Ser Gly Thr Asp Tyr Thr Leu Thr Ile Ser Ser Leu Gln Pro
 65                  70                  75                  80

Glu Asp Phe Ala Thr Tyr Tyr Cys Leu Gln Phe Tyr Glu Phe Pro Pro
                 85                  90                  95

Thr Phe Gly Gly Gly Thr Lys Val Glu Ile Lys
            100                 105

<210> SEQ ID NO 21
<211> LENGTH: 107
<212> TYPE: PRT
<213> ORGANISM: Artificial Sequence
<220> FEATURE:
<223> OTHER INFORMATION: Synthetic

<400> SEQUENCE: 21

Asp Ile Gln Met Thr Gln Ser Pro Ser Ser Leu Ser Ala Ser Val Gly
 1               5                  10                  15

Asp Arg Val Thr Ile Thr Cys Gln Ala Thr Gln Asp Ile Val Lys Ser
                 20                  25                  30

Leu Asn Trp Tyr Gln Gln Lys Pro Gly Lys Ala Pro Lys Phe Leu Ile
             35                  40                  45

Tyr Tyr Thr Ala Gln Leu Ala Glu Gly Val Pro Ser Arg Phe Ser Gly
         50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Leu Gln Phe Tyr Glu Phe Pro Pro
                 85                  90                  95

Thr Phe Gly Gly Gly Thr Lys Val Glu Ile Lys
            100                 105

<210> SEQ ID NO 22
<211> LENGTH: 107
<212> TYPE: PRT
<213> ORGANISM: Artificial Sequence
<220> FEATURE:
<223> OTHER INFORMATION: Synthetic

<400> SEQUENCE: 22

Asp Ile Gln Met Thr Gln Ser Pro Ser Ser Leu Ser Ala Ser Val Gly
 1               5                  10                  15

Asp Arg Val Thr Ile Thr Cys Gln Ala Thr Gln Asp Ile Val Lys Ser
                 20                  25                  30

Leu Asn Trp Tyr Gln Gln Lys Pro Gly Lys Pro Pro Lys Phe Leu Ile
             35                  40                  45

Tyr Tyr Thr Ala Gln Leu Ala Glu Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Phe Tyr Glu Phe Pro Pro
                 85                  90                  95

Thr Phe Gly Gly Gly Thr Lys Val Glu Ile Lys
            100                 105

<210> SEQ ID NO 23
<211> LENGTH: 107
<212> TYPE: PRT
<213> ORGANISM: Artificial Sequence
<220> FEATURE:
<223> OTHER INFORMATION: Synthetic
```

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Gln Ala Thr Gln Asp Ile Val Lys Ser
            20                  25                  30

Leu Asn Trp Tyr Gln Gln Lys Pro Gly Lys Pro Pro Lys Phe Ala Ile
        35                  40                  45

Tyr Tyr Thr Ala Gln Leu Ala Glu Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Phe Tyr Glu Phe Pro Pro
                85                  90                  95

Thr Phe Gly Gly Gly Thr Lys Val Glu Ile Lys
            100                 105

<210> SEQ ID NO 24
<211> LENGTH: 214
<212> TYPE: PRT
<213> ORGANISM: Artificial Sequence
<220> FEATURE:
<223> OTHER INFORMATION: Synthetic

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Gln Ala Thr Gln Asp Ile Val Lys Ser
            20                  25                  30

Leu Asn Trp Tyr Gln Gln Lys Pro Gly Lys Pro Pro Lys Phe Leu Ile
        35                  40                  45

Tyr Tyr Thr Ala Gln Leu Ala Glu Gly Val Pro Ser Arg Phe Ser Gly
    50                  55                  60

Ser Gly Ser Gly Thr Asp Tyr Thr Leu Thr Ile Ser Ser Leu Gln Ser
65                  70                  75                  80

Glu Asp Phe Ala Thr Tyr Tyr Cys Leu Gln Phe Tyr Glu Phe Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 214

```
<212> TYPE: PRT
<213> ORGANISM: Artificial Sequence
<220> FEATURE:
<223> OTHER INFORMATION: Synthetic

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Gln Ala Thr Gln Asp Ile Val Lys Ser
            20                  25                  30

Leu Asn Trp Tyr Gln Gln Lys Pro Gly Lys Pro Lys Phe Leu Ile
        35                  40                  45

Tyr Tyr Thr Ala Gln Leu Ala Glu Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Phe Tyr Glu Phe Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 26
<211> LENGTH: 214
<212> TYPE: PRT
<213> ORGANISM: Artificial Sequence
<220> FEATURE:
<223> OTHER INFORMATION: Synthetic

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Gln Ala Thr Gln Asp Ile Val Lys Ser
            20                  25                  30

Leu Asn Trp Tyr Gln Gln Lys Pro Gly Lys Ala Pro Lys Phe Leu Ile
        35                  40                  45

Tyr Tyr Thr Ala Gln Leu Ala Glu Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Phe Tyr Glu Phe Pro Pro
                85                  90                  95

Thr Phe Gly Gly Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 27
<211> LENGTH: 214
<212> TYPE: PRT
<213> ORGANISM: Artificial Sequence
<220> FEATURE:
<223> OTHER INFORMATION: Synthetic

<400> SEQUENCE: 27

```
Asp Ile Gln Met Thr Gln Ser Pro Ser Ser Leu Ser Ala Ser Val Gly
1               5                   10                  15

Asp Arg Val Thr Ile Thr Cys Gln Ala Thr Gln Asp Ile Val Lys Ser
            20                  25                  30

Leu Asn Trp Tyr Gln Gln Lys Pro Gly Lys Pro Pro Lys Phe Leu Ile
        35                  40                  45

Tyr Tyr Thr Ala Gln Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Phe Tyr Glu Phe Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 28
<211> LENGTH: 214
<212> TYPE: PRT
<213> ORGANISM: Artificial Sequence
<220> FEATURE:
<223> OTHER INFORMATION: Synthetic

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Gln Ala Thr Gln Asp Ile Val Lys Ser
            20                  25                  30

Leu Asn Trp Tyr Gln Gln Lys Pro Gly Lys Pro Lys Phe Leu Ile
        35                  40                  45

Tyr Tyr Thr Ala Gln Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Phe Tyr Glu Phe Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 29
<211> LENGTH: 117
<212> TYPE: PRT
<213> ORGANISM: Mus musculus

<400> SEQUENCE: 29

Glu Val Gln Leu Gln Gln Ser Gly Thr Val Leu Ala Arg Pro Gly Ala
1               5                   10                  15

Ser Val Lys Met Ser Cys Lys Val Ser Gly Tyr Pro Phe Thr Ser Tyr
            20                  25                  30

Trp Met His Trp Val Lys Gln Arg Pro Gly Gln Gly Leu Glu Trp Ile
        35                  40                  45

Gly Ala Ile Tyr Pro Gly Lys Ser Asp Thr Glu Tyr Asn Pro Asn Phe
    50                  55                  60

Lys Gly Lys Ala Lys Leu Thr Ala Val Thr Ser Ala Thr Thr Ala Tyr
65                  70                  75                  80

Met Glu Leu Ser Ser Leu Thr Asn Glu Asp Ser Ala Val Tyr Tyr Cys
                85                  90                  95

Thr Ser Thr Trp Thr His Tyr Phe Asp Tyr Trp Gly Gln Gly Thr Thr
            100                 105                 110

Leu Thr Val Ser Ser
        115

<210> SEQ ID NO 30
<211> LENGTH: 17
<212> TYPE: PRT
<213> ORGANISM: Mus musculus

<400> SEQUENCE: 30

Ala Ile Tyr Pro Gly Lys Ser Asp Thr Glu Tyr Asn Pro Asn Phe Lys
1               5                   10                  15

Gly

<210> SEQ ID NO 31
<211> LENGTH: 351
<212> TYPE: DNA
<213> ORGANISM: Mus musculus

<400> SEQUENCE: 31
gaggttcagc tccagcagtc tgggactgtt ctggcaaggc ctggggcttc agtgaagatg      60
tcctgcaagg tttctggcta ccccttacc agctactgga tgcactgggt aaaacagagg     120
cctggacagg gtctggaatg gattggcgct atttatcctg gaaaaagtga cactgaatac     180
aacccgaact tcaagggcaa ggccaaactg actgcagtca catctgccac cactgcctac     240
atggagctca gcagcctgac aaatgaggac tctgcggtct attactgtac aagtacctgg     300
acccactact ttgactactg gggccaaggc accactctca cagtctcctc a              351

<210> SEQ ID NO 32
<211> LENGTH: 330
<212> TYPE: PRT
<213> ORGANISM: Mus musculus

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 33
<211> LENGTH: 330
<212> TYPE: PRT
<213> ORGANISM: Mus musculus

<400> SEQUENCE: 33

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Leu Pro Glu Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
```

```
                      245                 250                 255
Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 34
<211> LENGTH: 117
<212> TYPE: PRT
<213> ORGANISM: Artificial Sequence
<220> FEATURE:
<223> OTHER INFORMATION: Synthetic

<400> SEQUENCE: 34

Glu Val Gln Leu Val Gln Ser Gly Ala Glu Val Lys Lys Pro Gly Ala
1               5                   10                  15

Ser Val Lys Val Ser Cys Lys Val Ser Gly Tyr Pro Phe Thr Ser Tyr
            20                  25                  30

Trp Met His Trp Val Arg Gln Ala Pro Gly Gln Gly Leu Glu Trp Ile
        35                  40                  45

Gly Ala Ile Tyr Pro Gly Lys Ser Asp Thr Glu Tyr Ala Pro Lys Phe
    50                  55                  60

Gln Gly Arg Val Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Thr Trp Thr His Tyr Phe Asp Tyr Trp Gly Gln Gly Thr Thr
            100                 105                 110

Val Thr Val Ser Ser
        115

<210> SEQ ID NO 35
<211> LENGTH: 117
<212> TYPE: PRT
<213> ORGANISM: Artificial Sequence
<220> FEATURE:
<223> OTHER INFORMATION: Synthetic

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Val Ser Gly Tyr Pro Phe Thr Ser Tyr
            20                  25                  30

Trp Met His Trp Val Arg Gln Ala Pro Gly Gln Gly Leu Glu Trp Met
        35                  40                  45

Gly Ala Ile Tyr Pro Gly Lys Ser Asp Thr Glu Tyr Ala Gln Lys Phe
    50                  55                  60

Gln Gly Arg Val Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Thr Ser Thr Trp Thr His Tyr Phe Asp Tyr Trp Gln Gly Thr Thr
            100                 105                 110

Val Thr Val Ser Ser
        115

<210> SEQ ID NO 36
<211> LENGTH: 117
<212> TYPE: PRT
<213> ORGANISM: Artificial Sequence
<220> FEATURE:
<223> OTHER INFORMATION: Synthetic

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Val Ser Gly Tyr Pro Phe Thr Ser Tyr
            20                  25                  30

Trp Met His Trp Val Arg Gln Ala Pro Gly Gln Gly Leu Glu Trp Met
        35                  40                  45

Gly Ala Ile Tyr Pro Gly Lys Ser Asp Thr Glu Tyr Ala Gln Lys Phe
    50                  55                  60

Gln Gly Arg Val Thr Leu Thr Ala Asp Thr Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Thr Ser Thr Trp Thr His Tyr Phe Asp Tyr Trp Gln Gly Thr Thr
            100                 105                 110

Val Thr Val Ser Ser
        115

<210> SEQ ID NO 37
<211> LENGTH: 117
<212> TYPE: PRT
<213> ORGANISM: Artificial Sequence
<220> FEATURE:
<223> OTHER INFORMATION: Synthetic

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Val Ser Gly Tyr Pro Phe Thr Ser Tyr
            20                  25                  30

Tyr Met His Trp Val Arg Gln Ala Pro Gly Gln Gly Leu Glu Trp Met
        35                  40                  45

Gly Ala Ile Tyr Pro Gly Lys Ser Asp Thr Glu Tyr Ala Gln Lys Phe
    50                  55                  60

Gln Gly Arg Val Thr Leu Thr Ala Asp Thr Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Thr Ser Thr Trp Thr His Tyr Phe Asp Tyr Trp Gln Gly Thr Thr
            100                 105                 110

Val Thr Val Ser Ser
        115

<210> SEQ ID NO 38
<211> LENGTH: 447
<212> TYPE: PRT
<213> ORGANISM: Artificial Sequence
<220> FEATURE:
<223> OTHER INFORMATION: Synthetic

<400> SEQUENCE: 38

Glu Val Gln Leu Val Gln Ser Gly Ala Glu Val Lys Lys Pro Gly Ala
1               5                   10                  15

Ser Val Lys Val Ser Cys Lys Val Ser Gly Tyr Pro Phe Thr Ser Tyr
                20                  25                  30

Trp Met His Trp Val Arg Gln Ala Pro Gly Gln Gly Leu Glu Trp Ile
            35                  40                  45

Gly Ala Ile Tyr Pro Gly Lys Ser Asp Thr Glu Tyr Ala Pro Lys Phe
        50                  55                  60

Gln Gly Arg Val Thr Leu Thr Ala Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Thr Trp Thr His Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

```
Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 39
<211> LENGTH: 447
<212> TYPE: PRT
<213> ORGANISM: Artificial Sequence
<220> FEATURE:
<223> OTHER INFORMATION: Synthetic

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Val Ser Gly Tyr Pro Phe Thr Ser Tyr
            20                  25                  30

Trp Met His Trp Val Arg Gln Ala Pro Gly Gln Gly Leu Glu Trp Met
        35                  40                  45

Gly Ala Ile Tyr Pro Gly Lys Ser Asp Thr Glu Tyr Ala Gln Lys Phe
    50                  55                  60

Gln Gly Arg Val Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Thr Trp Thr His Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

```
Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 40
<211> LENGTH: 447
<212> TYPE: PRT
<213> ORGANISM: Artificial Sequence
<220> FEATURE:
<223> OTHER INFORMATION: Synthetic

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Val Ser Gly Tyr Pro Phe Thr Ser Tyr
            20                  25                  30

Trp Met His Trp Val Arg Gln Ala Pro Gly Gln Gly Leu Glu Trp Met
        35                  40                  45

Gly Ala Ile Tyr Pro Gly Lys Ser Asp Thr Glu Tyr Ala Gln Lys Phe
    50                  55                  60

Gln Gly Arg Val Thr Leu Thr Ala Asp Thr Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Thr Ser Thr Trp Thr His Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240
```

```
Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Synthetic

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Val Ser Gly Tyr Pro Phe Thr Ser Tyr
            20                  25                  30

Tyr Met His Trp Val Arg Gln Ala Pro Gly Gln Gly Leu Glu Trp Met
        35                  40                  45

Gly Ala Ile Tyr Pro Gly Lys Ser Asp Thr Glu Tyr Ala Gln Lys Phe
    50                  55                  60

Gln Gly Arg Val Thr Leu Thr Ala Asp Thr Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Thr Ser Thr Trp Thr His Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160
```

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Synthetic

<400> SEQUENCE: 42

Glu Val Gln Leu Val Gln Ser Gly Ala Glu Val Lys Lys Pro Gly Ala
1               5                   10                  15

Ser Val Lys Val Ser Cys Lys Val Ser Gly Tyr Pro Phe Thr Ser Tyr
            20                  25                  30

Trp Met His Trp Val Arg Gln Ala Pro Gly Gln Gly Leu Glu Trp Ile
        35                  40                  45

Gly Ala Ile Tyr Pro Gly Lys Ser Asp Thr Glu Tyr Ala Pro Lys Phe
    50                  55                  60

Gln Gly Arg Val Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Ser Thr Trp Thr His Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Asp Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Leu Pro Glu Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 43
<211> LENGTH: 447
<212> TYPE: PRT
<213> ORGANISM: Artificial Sequence
<220> FEATURE:
<223> OTHER INFORMATION: Synthetic

<400> SEQUENCE: 43

```
Gln Val Gln Leu Val Gln Ser Gly Ala Glu Lys Lys Pro Gly Ala
1               5                   10                  15

Ser Val Lys Val Ser Cys Lys Val Ser Gly Tyr Pro Phe Thr Ser Tyr
            20                  25                  30

Trp Met His Trp Val Arg Gln Ala Pro Gly Gln Gly Leu Glu Trp Met
            35                  40                  45

Gly Ala Ile Tyr Pro Gly Lys Ser Asp Thr Glu Tyr Ala Gln Lys Phe
50                  55                  60

Gln Gly Arg Val Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Thr Ser Thr Trp Thr His Tyr Phe Asp Tyr Trp Gly Gln Gly Thr Thr
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Asp Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Leu Pro Glu Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415
```

```
Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 44
<211> LENGTH: 447
<212> TYPE: PRT
<213> ORGANISM: Artificial Sequence
<220> FEATURE:
<223> OTHER INFORMATION: Synthetic

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Val Ser Gly Tyr Pro Phe Thr Ser Tyr
            20                  25                  30

Trp Met His Trp Val Arg Gln Ala Pro Gly Gln Gly Leu Glu Trp Met
        35                  40                  45

Gly Ala Ile Tyr Pro Gly Lys Ser Asp Thr Glu Tyr Ala Gln Lys Phe
    50                  55                  60

Gln Gly Arg Val Thr Leu Thr Ala Asp Thr Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Thr Ser Thr Trp Thr His Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Asp Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Leu Pro Glu Glu Lys Thr Ile
                325                 330                 335
```

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 45
<211> LENGTH: 447
<212> TYPE: PRT
<213> ORGANISM: Artificial Sequence
<220> FEATURE:
<223> OTHER INFORMATION: Synthetic

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Val Ser Gly Tyr Pro Phe Thr Ser Tyr
            20                  25                  30

Tyr Met His Trp Val Arg Gln Ala Pro Gly Gln Gly Leu Glu Trp Met
        35                  40                  45

Gly Ala Ile Tyr Pro Gly Lys Ser Asp Thr Glu Tyr Ala Gln Lys Phe
    50                  55                  60

Gln Gly Arg Val Thr Leu Thr Ala Asp Thr Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Thr Ser Thr Trp Thr His Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Asp Val
225                 230                 235                 240

Phe Leu Phe Pro Pro Lys Pro Lys Asp Thr Leu Met Ile Ser Arg Thr
                245                 250                 255

```
Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Leu Pro Glu Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 46
<211> LENGTH: 107
<212> TYPE: PRT
<213> ORGANISM: Mus musculus

<400> SEQUENCE: 46

Glu Ile Gln Met Thr Gln Ser Pro Ser Ser Met Ser Ala Ser Leu Gly
1               5                   10                  15

Asp Thr Ile Thr Ile Thr Cys Gln Ala Thr Gln Asp Ile Val Lys Ser
            20                  25                  30

Leu Asn Trp Tyr Gln Gln Lys Pro Gly Lys Pro Ser Phe Leu Ile
        35                  40                  45

Tyr Tyr Thr Thr Gln Leu Ala Glu Gly Val Pro Ser Arg Phe Ser Gly
    50                  55                  60

Ser Gly Ser Gly Ser Asp Tyr Ser Leu Thr Ile Ser Asn Leu Asp Ser
65                  70                  75                  80

Glu Asp Phe Ala Asp Tyr Tyr Cys Leu Gln Phe Tyr Glu Phe Pro Pro
                85                  90                  95

Thr Phe Gly Gly Gly Thr Lys Leu Glu Ile Lys
            100                 105

<210> SEQ ID NO 47
<211> LENGTH: 8
<212> TYPE: PRT
<213> ORGANISM: Mus musculus

<400> SEQUENCE: 47

Tyr Tyr Thr Thr Gln Leu Ala Glu
1               5

<210> SEQ ID NO 48
<211> LENGTH: 321
```

```
<212> TYPE: DNA
<213> ORGANISM: Mus musculus

<400> SEQUENCE: 48
gaaatccaga tgacccagtc tccatcctct atgtctgcat ctctgggaga cacaataacc    60
atcacttgcc aggcaactca agacattgtt aagagtttaa actggtatca acaaaaacca   120
gggaaacccc cttcattcct gatctattat acaactcaac tggcagaagg ggtcccatca   180
aggttcagtg gcagtgggtc tgggtcagac tattctctga caatcagcaa cctggactct   240
gaagattttg cagactatta ctgtctacag ttttatgagt ttcctccgac gttcggtgga   300
ggcaccaagc tggaaatcaa a                                             321

<210> SEQ ID NO 49
<211> LENGTH: 117
<212> TYPE: PRT
<213> ORGANISM: Mus musculus

<400> SEQUENCE: 49

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Ser Ser Tyr
            20                  25                  30

Trp Met His Trp Val Lys Gln Arg Pro Gly Gln Gly Leu Glu Trp Ile
        35                  40                  45

Gly Ala Ile Tyr Pro Gly Lys Ser Asp Thr Glu Tyr Asn Gln Lys Phe
    50                  55                  60

Gln Gly Lys Ala Lys Leu Thr Ala Val Thr Ser Ala Ser Thr Ala Phe
65                  70                  75                  80

Met Glu Leu Thr Ser Leu Thr Asn Glu Asp Ser Ala Val Tyr Tyr Cys
                85                  90                  95

Thr Ser Thr Trp Thr His Tyr Phe Asp Tyr Trp Gly Gln Gly Thr Thr
            100                 105                 110

Leu Thr Val Ser Ser
        115

<210> SEQ ID NO 50
<211> LENGTH: 17
<212> TYPE: PRT
<213> ORGANISM: Mus musculus

<400> SEQUENCE: 50

Ala Ile Tyr Pro Gly Lys Ser Asp Thr Glu Tyr Asn Pro Asn Phe Lys
1               5                   10                  15

Gly

<210> SEQ ID NO 51
<211> LENGTH: 351
<212> TYPE: DNA
<213> ORGANISM: Mus musculus

<400> SEQUENCE: 51
gaggttcagc tccagcagtc tgggactgtt ctggcaaggc ctggggcttc agtgaagatg    60
tcctgcaagg cttctggcta cacctttttcc agctactgga tgcactgggt aaaacagagg   120
cctggacagg gtctggaatg gattggcgct atttatcctg gaaaaagtga tactagctac   180
aaccagaagt tccagggcaa ggccaaactg actgcagtca catctgccag cactgccttc   240
atggagctca ccagcctgac aaatgaggac tctgcggtct attactgtac aagtacctgg   300
```

```
acccactact tgactactg gggccaaggc accactctca cagtctcctc a            351
```

<210> SEQ ID NO 52
<211> LENGTH: 107
<212> TYPE: PRT
<213> ORGANISM: Mus musculus

<400> SEQUENCE: 52

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Ile Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Ser Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Phe Lys
            100                 105

<210> SEQ ID NO 53
<211> LENGTH: 11
<212> TYPE: PRT
<213> ORGANISM: Mus musculus

<400> SEQUENCE: 53

Arg Ala Ser Gln Asp Ile Ser Asn Tyr Leu Asn
1               5                   10

<210> SEQ ID NO 54
<211> LENGTH: 7
<212> TYPE: PRT
<213> ORGANISM: Mus musculus

<400> SEQUENCE: 54

Tyr Thr Ser Arg Leu His Ser
1               5

<210> SEQ ID NO 55
<211> LENGTH: 9
<212> TYPE: PRT
<213> ORGANISM: Mus musculus

<400> SEQUENCE: 55

Gln Gln Gly Asn Thr Leu Pro Trp Thr
1               5

<210> SEQ ID NO 56
<211> LENGTH: 321
<212> TYPE: DNA
<213> ORGANISM: Mus musculus

<400> SEQUENCE: 56

```
gatatccaga tgacacaaac tacatcctcc ctgtctgcct ctctgggaga cagagtcacc    60
atcagttgca gggcaagtca ggacattagc aattatttaa actggtatca gcagaaacca   120
gatggaacta ttaaactcct gatctattac acatcaagat acattccagg agtcccatca   180
```
aggttcagtg gcagtgggtc tggatcagat tattctctca ccattagcaa cctggagcaa    240
gaagatattg ccacttactt ttgccaacag ggtaatacgc ttccgtggac gttcggtgga    300
ggcaccaagc tggaattcaa a    321

<210> SEQ ID NO 57
<211> LENGTH: 214
<212> TYPE: PRT
<213> ORGANISM: Mus musculus

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Thr Ile Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 58
<211> LENGTH: 107
<212> TYPE: PRT
<213> ORGANISM: Artificial Sequence
<220> FEATURE:
<223> OTHER INFORMATION: Synthetic

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Thr Ile Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro

```
                65                  70                  75                  80
Glu Asp Phe Ala Thr Tyr Phe Cys Gln Gln Gly Asn Thr Leu Pro Trp
                    85                  90                  95

Thr Phe Gly Gln Gly Thr Lys Leu Glu Ile Lys
            100                 105

<210> SEQ ID NO 59
<211> LENGTH: 107
<212> TYPE: PRT
<213> ORGANISM: Artificial Sequence
<220> FEATURE:
<223> OTHER INFORMATION: Synthetic

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                    85                  90                  95

Thr Phe Gly Gln Gly Thr Lys Leu Glu Ile Lys
            100                 105

<210> SEQ ID NO 60
<211> LENGTH: 107
<212> TYPE: PRT
<213> ORGANISM: Artificial Sequence
<220> FEATURE:
<223> OTHER INFORMATION: Synthetic

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Gln Thr Leu Pro Trp
                    85                  90                  95

Thr Phe Gly Gln Gly Thr Lys Leu Glu Ile Lys
            100                 105

<210> SEQ ID NO 61
<211> LENGTH: 107
<212> TYPE: PRT
<213> ORGANISM: Artificial Sequence
<220> FEATURE:
<223> OTHER INFORMATION: Synthetic

<400> SEQUENCE: 61
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Ser Thr Leu Pro Trp
                85                  90                  95

Thr Phe Gly Gln Gly Thr Lys Leu Glu Ile Lys
            100                 105
```

<210> SEQ ID NO 62
<211> LENGTH: 214
<212> TYPE: PRT
<213> ORGANISM: Artificial Sequence
<220> FEATURE:
<223> OTHER INFORMATION: Synthetic

<400> SEQUENCE: 62

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 63
<211> LENGTH: 214
<212> TYPE: PRT
<213> ORGANISM: Artificial Sequence
<220> FEATURE:
<223> OTHER INFORMATION: Synthetic

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Gln Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 64
<211> LENGTH: 214
<212> TYPE: PRT
<213> ORGANISM: Artificial Sequence
<220> FEATURE:
<223> OTHER INFORMATION: Synthetic

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Ser Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly 115                 120                 125
Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 65
<211> LENGTH: 116
<212> TYPE: PRT
<213> ORGANISM: Mus musculus

<400> SEQUENCE: 65

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Arg Gln Ser His Gly Lys Ser Leu Glu Trp Ile
        35                  40                  45

Gly Arg Val Asn Pro Ser Asn Gly Gly Thr Asn Tyr Asn Gln Lys Phe
    50                  55                  60

Lys Gly Lys Ala Thr Leu Thr Val Asp Lys Ser Leu Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Arg His Asn Tyr Ala Asp Phe Trp Gly Gln Gly Thr Thr Leu
            100                 105                 110

Thr Val Ser Ser
        115

<210> SEQ ID NO 66
<211> LENGTH: 5
<212> TYPE: PRT
<213> ORGANISM: Mus musculus

<400> SEQUENCE: 66

Asp Tyr Tyr Met Asn
1               5

<210> SEQ ID NO 67
<211> LENGTH: 17
<212> TYPE: PRT
<213> ORGANISM: Mus musculus

<400> SEQUENCE: 67

Arg Val Asn Pro Ser Asn Gly Gly Thr Asn Tyr Asn Gln Lys Phe Lys
1               5                   10                  15

Gly

<210> SEQ ID NO 68
<211> LENGTH: 7

```
<212> TYPE: PRT
<213> ORGANISM: Mus musculus

<400> SEQUENCE: 68

Arg His Asn Tyr Ala Asp Phe
1               5

<210> SEQ ID NO 69
<211> LENGTH: 348
<212> TYPE: DNA
<213> ORGANISM: Mus musculus

<400> SEQUENCE: 69
gaggtccagc tgcaacagtc tggacctgag ctggtgaagc ctggggcttc agtgaagatg    60
tcctgtaagg cttctggata cacattcact gactactaca tgaactgggt gaggcagagt   120
catggaaaga gccttgagtg gattggacgt gttaatccta gcaatggtgg tactaactac   180
aaccagaaat tcaagggcaa ggccacattg acagtagaca atccctcag cacagcctac    240 atgcagctca gcagcctgac atctgaggac tctgcggtct attactgtgc aagacgacat   300
aactacgcag acttctgggg ccaaggcacc actctcacag tctcctca                348

<210> SEQ ID NO 70
<211> LENGTH: 116
<212> TYPE: PRT
<213> ORGANISM: Artificial Sequence
<220> FEATURE:
<223> OTHER INFORMATION: Synthetic

<400> SEQUENCE: 70

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Arg Val Asn Pro Ser Asn Gly Gly Thr Asn Tyr Ala Gln Lys Phe
    50                  55                  60

Gln Gly Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg His Asn Tyr Ala Asp Phe Trp Gly Gln Gly Thr Thr Val
            100                 105                 110

Thr Val Ser Ser
        115

<210> SEQ ID NO 71
<211> LENGTH: 116
<212> TYPE: PRT
<213> ORGANISM: Artificial Sequence
<220> FEATURE:
<223> OTHER INFORMATION: Synthetic

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
```

```
                35                  40                  45
Gly Arg Val Asn Pro Ala Asn Gly Gly Thr Asn Tyr Ala Gln Lys Phe
    50                  55                  60
Gln Gly Arg Val Thr Leu Thr Val Asp Thr Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Arg His Asn Tyr Ala Asp Phe Trp Gly Gln Gly Thr Thr Val
                100                 105                 110
Thr Val Ser Ser
        115

<210> SEQ ID NO 72
<211> LENGTH: 116
<212> TYPE: PRT
<213> ORGANISM: Artificial Sequence
<220> FEATURE:
<223> OTHER INFORMATION: Synthetic

<400> SEQUENCE: 72

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
                20                  25                  30
Tyr Met Asn Trp Val Arg Gln Ala Pro Gly Gln Gly Leu Glu Trp Met
                35                  40                  45
Gly Arg Val Asn Pro Ser Ser Gly Gly Thr Asn Tyr Ala Gln Lys Phe
    50                  55                  60
Gln Gly Arg Val Thr Leu Thr Val Asp Thr Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Arg His Asn Tyr Ala Asp Phe Trp Gly Gln Gly Thr Thr Val
                100                 105                 110
Thr Val Ser Ser
        115

<210> SEQ ID NO 73
<211> LENGTH: 116
<212> TYPE: PRT
<213> ORGANISM: Artificial Sequence
<220> FEATURE:
<223> OTHER INFORMATION: Synthetic

<400> SEQUENCE: 73

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
                20                  25                  30
Tyr Met Asn Trp Val Arg Gln Ala Pro Gly Gln Gly Leu Glu Trp Met
                35                  40                  45
Gly Arg Val Asn Pro Ser Asn Gly Gly Thr Asn Tyr Ala Gln Lys Phe
    50                  55                  60
Gln Gly Arg Val Thr Leu Thr Val Asp Thr Ser Lys Ser Thr Ala Tyr
65                  70                  75                  80
Met Glu Leu Ser Ser Leu Arg Ser Glu Asp Thr Ala Val Tyr Tyr Cys
                85                  90                  95
```

-continued

Ala Arg Arg His Asn Tyr Ala Asp Phe Trp Gly Gln Gly Thr Thr Val
            100                 105                 110

Thr Val Ser Ser
        115

<210> SEQ ID NO 74
<211> LENGTH: 116
<212> TYPE: PRT
<213> ORGANISM: Artificial Sequence
<220> FEATURE:
<223> OTHER INFORMATION: Synthetic

<400> SEQUENCE: 74

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Arg Val Asn Pro Ser Ser Gly Gly Thr Asn Tyr Ala Gln Lys Phe
    50                  55                  60

Gln Gly Arg Val Thr Leu Thr Val Asp Thr Ser Lys Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg His Asn Tyr Ala Asp Phe Trp Gly Gln Gly Thr Thr Val
            100                 105                 110

Thr Val Ser Ser
        115

<210> SEQ ID NO 75
<211> LENGTH: 446
<212> TYPE: PRT
<213> ORGANISM: Artificial Sequence
<220> FEATURE:
<223> OTHER INFORMATION: Synthetic

<400> SEQUENCE: 75

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Arg Val Asn Pro Ser Asn Gly Gly Thr Asn Tyr Ala Gln Lys Phe
    50                  55                  60

Gln Gly Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg His Asn Tyr Ala Asp Phe Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 76
<211> LENGTH: 446
<212> TYPE: PRT
<213> ORGANISM: Artificial Sequence
<220> FEATURE:
<223> OTHER INFORMATION: Synthetic

<400> SEQUENCE: 76

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Arg Val Asn Pro Ala Asn Gly Gly Thr Asn Tyr Ala Gln Lys Phe
    50                  55                  60

Gln Gly Arg Val Thr Leu Thr Val Asp Thr Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Arg Arg His Asn Tyr Ala Asp Phe Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 77
<211> LENGTH: 446
<212> TYPE: PRT
<213> ORGANISM: Artificial Sequence
<220> FEATURE:
<223> OTHER INFORMATION: Synthetic

<400> SEQUENCE: 77
```

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Arg Val Asn Pro Ser Ser Gly Gly Thr Asn Tyr Ala Gln Lys Phe
    50                  55                  60

Gln Gly Arg Val Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg His Asn Tyr Ala Asp Phe Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

```
Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
        435                 440                 445

<210> SEQ ID NO 78
<211> LENGTH: 446
<212> TYPE: PRT
<213> ORGANISM: Artificial Sequence
<220> FEATURE:
<223> OTHER INFORMATION: Synthetic

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Arg Val Asn Pro Ser Asn Gly Gly Thr Asn Tyr Ala Gln Lys Phe
50                  55                  60

Gln Gly Arg Val Thr Leu Thr Val Asp Thr Ser Lys Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg His Asn Tyr Ala Asp Phe Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335
```

```
Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 79
<211> LENGTH: 446
<212> TYPE: PRT
<213> ORGANISM: Artificial Sequence
<220> FEATURE:
<223> OTHER INFORMATION: Synthetic

<400> SEQUENCE: 79

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Arg Val Asn Pro Ser Ser Gly Gly Thr Asn Tyr Ala Gln Lys Phe
    50                  55                  60

Gln Gly Arg Val Thr Leu Thr Val Asp Thr Ser Lys Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg His Asn Tyr Ala Asp Phe Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255
```

-continued

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 80
<211> LENGTH: 446
<212> TYPE: PRT
<213> ORGANISM: Artificial Sequence
<220> FEATURE:
<223> OTHER INFORMATION: Synthetic

<400> SEQUENCE: 80

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met Asn Trp Val Arg Gln Ala Pro Gly Gln Gly Leu Glu Trp Ile
            35                  40                  45

Gly Arg Val Asn Pro Ser Asn Gly Gly Thr Asn Tyr Ala Gln Lys Phe
        50                  55                  60

Gln Gly Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg His Asn Tyr Ala Asp Phe Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Asp Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Leu Pro Glu Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
    435                 440                 445

<210> SEQ ID NO 81
<211> LENGTH: 446
<212> TYPE: PRT
<213> ORGANISM: Artificial Sequence
<220> FEATURE:
<223> OTHER INFORMATION: Synthetic

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Arg Val Asn Pro Ala Asn Gly Gly Thr Asn Tyr Ala Gln Lys Phe
    50                  55                  60

Gln Gly Arg Val Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg His Asn Tyr Ala Asp Phe Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Asp Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Leu Pro Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
    435                 440                 445

<210> SEQ ID NO 82
<211> LENGTH: 446
<212> TYPE: PRT
<213> ORGANISM: Artificial Sequence
<220> FEATURE:
<223> OTHER INFORMATION: Synthetic

<400> SEQUENCE: 82

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Arg Val Asn Pro Ser Ser Gly Gly Thr Asn Tyr Ala Gln Lys Phe
    50                  55                  60

Gln Gly Arg Val Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg His Asn Tyr Ala Asp Phe Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Asp Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Leu Pro Glu Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys

-continued

```
            435             440             445
```

<210> SEQ ID NO 83
<211> LENGTH: 446
<212> TYPE: PRT
<213> ORGANISM: Artificial Sequence
<220> FEATURE:
<223> OTHER INFORMATION: Synthetic

<400> SEQUENCE: 83

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Arg Val Asn Pro Ser Asn Gly Gly Thr Asn Tyr Ala Gln Lys Phe
    50                  55                  60

Gln Gly Arg Val Thr Leu Thr Val Asp Thr Ser Lys Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg His Asn Tyr Ala Asp Phe Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Asp Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Leu Pro Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
```

```
                355                 360                 365
Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 84
<211> LENGTH: 446
<212> TYPE: PRT
<213> ORGANISM: Artificial Sequence
<220> FEATURE:
<223> OTHER INFORMATION: Synthetic

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met Asn Trp Val Arg Gln Ala Pro Gly Gln Gly Leu Glu Trp Met
            35                  40                  45

Gly Arg Val Asn Pro Ser Ser Gly Gly Thr Asn Tyr Ala Gln Lys Phe
        50                  55                  60

Gln Gly Arg Val Thr Leu Thr Val Asp Thr Ser Lys Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg His Asn Tyr Ala Asp Phe Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Asp Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
```

-continued

```
                    275                 280                 285
Lys Pro Arg Glu Glu Gln Tyr Asn Ser Thr Tyr Arg Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Leu Pro Glu Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
                435                 440                 445

<210> SEQ ID NO 85
<211> LENGTH: 107
<212> TYPE: PRT
<213> ORGANISM: Mus musculus

<400> SEQUENCE: 85

Glu Thr Val Met Thr Gln Ser His Lys Ile Met Ser Thr Ser Val Gly
1               5                   10                  15

Asp Arg Val Thr Ile Thr Cys Lys Ala Ser Gln Asp Val Arg Thr Ala
                20                  25                  30

Val Ala Trp Tyr Gln Gln Lys Pro Gly Gln Ser Pro Lys Leu Leu Ile
            35                  40                  45

Ser Ser Ala Ser Tyr Gln Tyr Thr Gly Val Pro Asp Arg Phe Thr Gly
        50                  55                  60

Ser Gly Ser Gly Thr Asp Phe Thr Phe Thr Ile Ser Ser Leu Gln Ala
65                  70                  75                  80

Glu Asp Leu Ala Val Tyr Tyr Cys His Gln Tyr Tyr Asn Thr Pro Leu
                85                  90                  95

Thr Phe Gly Ala Gly Thr Lys Leu Glu Leu Arg
            100                 105

<210> SEQ ID NO 86
<211> LENGTH: 7
<212> TYPE: PRT
<213> ORGANISM: Mus musculus

<400> SEQUENCE: 86

Ser Ala Ser Tyr Gln Tyr Thr
1               5

<210> SEQ ID NO 87
<211> LENGTH: 9
<212> TYPE: PRT
<213> ORGANISM: Mus musculus

<400> SEQUENCE: 87
```

```
His Gln Tyr Tyr Asn Thr Pro Leu Thr
1               5
```

<210> SEQ ID NO 88
<211> LENGTH: 321
<212> TYPE: DNA
<213> ORGANISM: Mus musculus

<400> SEQUENCE: 88

```
gaaactgtga tgacccagtc tcacaaaatc atgtccactt cagtaggaga cagggtcacc      60
atcacctgca aggccagtca ggatgtgaga actgctgtgg cctggtatca acagaaacca    120
ggacaatctc ctaaattact aatttcctcg gcatcctacc aatacactgg agtccctgat    180
cgcttcactg gcagtggatc tgggacggat ttcactttca ccatcagcag tttgcaggct    240
gaagacctgg cagtttatta ctgtcatcag tattataata ctccgctcac gttcggtgct    300
gggaccaagc tggagctgag a                                              321
```

<210> SEQ ID NO 89
<211> LENGTH: 117
<212> TYPE: PRT
<213> ORGANISM: Mus musculus

<400> SEQUENCE: 89

```
Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Ala Ile Tyr Pro Gly Lys Ser Asp Thr Thr Tyr Asn Gln Lys Phe
    50                  55                  60

Glu Gly Lys Ala Lys Leu Thr Ala Val Thr Ser Asp Ser Thr Ala Tyr
65                  70                  75                  80

Met Asp Leu Ser Ser Leu Thr Asn Glu Asp Ser Ala Val Tyr Tyr Cys
                85                  90                  95

Thr Ser Ser Val Arg Asn Ala Met Asp Tyr Trp Gly Gln Gly Thr Ser
            100                 105                 110

Val Thr Val Ser Ser
        115
```

<210> SEQ ID NO 90
<211> LENGTH: 17
<212> TYPE: PRT
<213> ORGANISM: Mus musculus

<400> SEQUENCE: 90

```
Ala Ile Tyr Pro Gly Lys Ser Asp Thr Thr Tyr Asn Gln Lys Phe Glu
1               5                   10                  15

Gly
```

<210> SEQ ID NO 91
<211> LENGTH: 8
<212> TYPE: PRT
<213> ORGANISM: Mus musculus

<400> SEQUENCE: 91

```
Ser Val Arg Asn Ala Met Asp Tyr
1               5
```

<210> SEQ ID NO 92
<211> LENGTH: 351
<212> TYPE: DNA
<213> ORGANISM: Mus musculus

<400> SEQUENCE: 92

```
gaggttcagc tccagcagtc tgggactgtg ctggcaaggc ctggggcttc agtgaagatg      60
tcctgcaagg cttctggcta caccttcacc agctactgga tgcactgggt aaaacagagg     120
cctggacagg gtctggaatg gattggcgct atttatcctg gaaaaagtga tactacctac     180
aaccagaagt tcgagggcaa ggccaaactg actgcagtca catctgacag cacagcctac     240
atggatctca gtagcctgac aaatgaggac tctgcggtct attactgtac atcttcggtt     300
cggaatgcta tggactactg gggtcaagga acctcagtca ccgtctcctc a              351
```

<210> SEQ ID NO 93
<211> LENGTH: 112
<212> TYPE: PRT
<213> ORGANISM: Mus musculus

<400> SEQUENCE: 93

```
Asp Val Leu Met Thr Gln Thr Pro Leu Ser Leu Pro Val Ser Leu Gly
1               5                   10                  15

Gly Gln Ala Ser Ile Ser Cys Arg Ser Ser Gln Ile Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110
```

<210> SEQ ID NO 94
<211> LENGTH: 16
<212> TYPE: PRT
<213> ORGANISM: Mus musculus

<400> SEQUENCE: 94

```
Arg Ser Ser Gln Ile Ile Val His Ser Asn Gly Asn Thr Tyr Leu Glu
1               5                   10                  15
```

<210> SEQ ID NO 95
<211> LENGTH: 7
<212> TYPE: PRT
<213> ORGANISM: Mus musculus

<400> SEQUENCE: 95

```
Lys Val Ser Asn Arg Phe Ser
1               5
```

<210> SEQ ID NO 96
<211> LENGTH: 9
<212> TYPE: PRT
<213> ORGANISM: Mus musculus

<400> SEQUENCE: 96

Phe Gln Gly Ser His Val Pro Trp Thr
1               5

<210> SEQ ID NO 97
<211> LENGTH: 336
<212> TYPE: DNA
<213> ORGANISM: Mus musculus

<400> SEQUENCE: 97
gatgttttga tgacccaaac tccactctcc ctgcctgtca gtcttggagg tcaagcctcc      60
atctcttgca gatctagtca gatcattgta catagtaatg aaacaccta tttagaatgg     120 tacctgcaga aaccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgttccg    300
tggacgttcg gtggaggcac caagctggaa atcaaa                              336

<210> SEQ ID NO 98
<211> LENGTH: 119
<212> TYPE: PRT
<213> ORGANISM: Mus musculus

<400> SEQUENCE: 98

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Ile Ser Tyr
            20                  25                  30

Trp Met His Trp Val Lys Gln Arg Pro Gly Gln Gly Leu Glu Trp Ile
        35                  40                  45

Gly Glu Ile Asp Pro Ser Asp Ser Tyr Thr Tyr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Lys Thr Trp Asp Trp Tyr Phe Asp Val Trp Gly Ala Gly
            100                 105                 110

Thr Thr Val Thr Val Ser Ser
        115

<210> SEQ ID NO 99
<211> LENGTH: 17
<212> TYPE: PRT
<213> ORGANISM: Mus musculus

<400> SEQUENCE: 99

Glu Ile Asp Pro Ser Asp Ser Tyr Thr Tyr Tyr Asn Gln Lys Phe Lys
1               5                   10                  15

Gly

<210> SEQ ID NO 100
<211> LENGTH: 10
<212> TYPE: PRT
<213> ORGANISM: Mus musculus

<400> SEQUENCE: 100

Arg Lys Thr Trp Asp Trp Tyr Phe Asp Val
1               5                   10

<210> SEQ ID NO 101
<211> LENGTH: 357
<212> TYPE: DNA
<213> ORGANISM: Mus musculus

<400> SEQUENCE: 101
caggtccagc tgcagcagcc tggggctgaa ctggtgaagc ctggggcttc agtgaagctg     60
tcctgcaagg cttctggata caccttcatt agctactgga tgcactgggt gaagcagagg    120
cctggacaag gccttgagtg gatcggagag attgatcctt ctgatagtta tacttactac    180
aatcaaaagt tcaagggcaa ggccacattg actgtagaca atcctccag cacagcctac     240 atgcaactca gcagcctgac atctgaggac tctgcggtct attactgtgc aagaaggaaa    300
acctgggact ggtacttcga tgtctggggc gcagggacca cggtcaccgt ctcctca       357

<210> SEQ ID NO 102
<211> LENGTH: 106
<212> TYPE: PRT
<213> ORGANISM: Mus musculus

<400> SEQUENCE: 102

Asp Ile Val Met Thr Gln Ser His Lys Phe Met Ser Thr Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Ser Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Thr
                85                  90                  95

Phe Gly Gly Gly Thr Lys Leu Glu Ile Arg
            100                 105

<210> SEQ ID NO 103
<211> LENGTH: 11
<212> TYPE: PRT
<213> ORGANISM: Mus musculus

<400> SEQUENCE: 103

Lys Ala Ser Gln Asp Val Ser Thr Ala Val Ala
1               5                   10

<210> SEQ ID NO 104
<211> LENGTH: 7
<212> TYPE: PRT
<213> ORGANISM: Mus musculus

<400> SEQUENCE: 104

Ser Ala Ser Tyr Arg Tyr Thr
1               5

<210> SEQ ID NO 105
<211> LENGTH: 8
<212> TYPE: PRT
<213> ORGANISM: Mus musculus

<400> SEQUENCE: 105

```
Gln Gln His Tyr Ser Thr Pro Thr
1               5
```

<210> SEQ ID NO 106
<211> LENGTH: 318
<212> TYPE: DNA
<213> ORGANISM: Mus musculus

<400> SEQUENCE: 106

```
gacattgtga tgacccagtc tcacaaattc atgtccacat cagtaggaga cagggtcact      60
atcacctgca aggccagtca ggatgtgagt actgctgtag cctggtatca acagaaacca     120
ggacagtctc ctaaactact gatttcctcg gcatcctacc ggtacactgg agtccctgat     180
cgcttcactg gcagtggatc tgggacggat ttcactttca ccatcagcag tgtgcaggct     240
gaagacctgg cagtttatta ctgtcagcaa cattatagta ctccgacgtt cggtggaggc     300
accaagctgg aaatcaga                                                   318
```

<210> SEQ ID NO 107
<211> LENGTH: 116
<212> TYPE: PRT
<213> ORGANISM: Mus musculus

<400> SEQUENCE: 107

```
Val Gln Leu Gln Gln Ser Gly Thr Val Leu Ala Arg Pro Gly Ala Ser
1               5                   10                  15

Val Lys Met Ser Cys Lys Ala Ser Gly Tyr Thr Phe Thr Ser Tyr Trp
            20                  25                  30

Met His Trp Val Lys Glu Arg Pro Gly Gln Gly Leu Glu Trp Ile Gly
        35                  40                  45

Ala Ile Tyr Pro Gly Asp Ser Asp Thr Arg Tyr Asn Gln Lys Phe Lys
    50                  55                  60

Gly Arg Ala Lys Leu Thr Ala Val Thr Ser Ala Asn Thr Ala Tyr Met
65                  70                  75                  80

Glu Leu Ser Ser Leu Thr Asn Asp Asp Ser Ala Val Phe Tyr Cys Thr
                85                  90                  95

Cys Thr Thr Ala Gly Val Leu Asp Tyr Trp Gly Gln Gly Thr Ser Val
            100                 105                 110

Thr Val Ser Ser
        115
```

<210> SEQ ID NO 108
<211> LENGTH: 17
<212> TYPE: PRT
<213> ORGANISM: Mus musculus

<400> SEQUENCE: 108

```
Ala Ile Tyr Pro Gly Asp Ser Asp Thr Arg Tyr Asn Gln Lys Phe Lys
1               5                   10                  15

Gly
```

<210> SEQ ID NO 109
<211> LENGTH: 8
<212> TYPE: PRT
<213> ORGANISM: Mus musculus

<400> SEQUENCE: 109

```
Thr Thr Ala Gly Val Leu Asp Tyr
1               5
```

<210> SEQ ID NO 110
<211> LENGTH: 351
<212> TYPE: DNA
<213> ORGANISM: Mus musculus

<400> SEQUENCE: 110
gaggttcagc tccagcagtc tgggactgtg ctggcaaggc ctggggcttc agtgaagatg     60
tcctgcaagg cttctggcta cacctttacc agctactgga tgcactgggt aaaagagagg    120
cctggacagg gtctggaatg gattggcgct atttatcctg agatagtga tactaggtat     180 aatcagaagt tcaagggcag ggccaaactg actgcagtca catctgccaa cactgcctac    240
atggagctca gcagcctgac aaatgatgac tctgcggtct tctactgtac atgtactacg    300
gctggtgttt tggactactg gggtcaagga acctcagtca ccgtctcctc a             351

<210> SEQ ID NO 111
<211> LENGTH: 112
<212> TYPE: PRT
<213> ORGANISM: Mus musculus

<400> SEQUENCE: 111

Asp Val Val Met Thr Gln Thr Pro Leu Ser Leu Pro Val Ser Leu Gly
1               5                   10                  15

Asp Gln Ala Ser Ile Ser Cys Thr Ser Ser Gln Ser Ile Val His Gly
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 112
<211> LENGTH: 16
<212> TYPE: PRT
<213> ORGANISM: Mus musculus

<400> SEQUENCE: 112

Thr Ser Ser Gln Ser Ile Val His Gly Asn Gly Asn Thr Tyr Leu Glu
1               5                   10                  15

<210> SEQ ID NO 113
<211> LENGTH: 9
<212> TYPE: PRT
<213> ORGANISM: Mus musculus

<400> SEQUENCE: 113

Phe Gln Gly Ser His Val Pro Tyr Thr
1               5

<210> SEQ ID NO 114
<211> LENGTH: 336
<212> TYPE: DNA
<213> ORGANISM: Mus musculus

<400> SEQUENCE: 114

```
gatgttgtga tgacccaaac tccactctcc ctgcctgtca gtcttggaga tcaggcctcc    60
atctcttgca catctagtca gagcattgta catggtaatg gaaacaccta tttagaatgg   120
tacctgcaga agccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tattactgct ttcaaggttc acatgttccg   300
tacacgttcg gaggggggac caagctggaa ataaaa                             336
```

<210> SEQ ID NO 115
<211> LENGTH: 123
<212> TYPE: PRT
<213> ORGANISM: Mus musculus

<400> SEQUENCE: 115

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Ser Phe Thr Ser Tyr
            20                  25                  30

Trp Met Asn Trp Val Lys Gln Arg Pro Gly Arg Gly Leu Glu Trp Ile
        35                  40                  45

Gly Arg Ile His Pro Ser Asp Ser Glu Thr His Tyr Asn Gln Lys Phe
    50                  55                  60

Lys Ser Lys Ala Thr Leu Thr Val Asp Lys Ser Ser Ser Thr Ala Tyr
65                  70                  75                  80

Ile Gln Leu Ser Ser Leu Thr Ser Glu Asp Ser Ala Val Tyr Phe Cys
                85                  90                  95

Ala Arg Tyr Gly Leu Phe Tyr Gly Asn Asp Gly Tyr Ala Met Asp His
            100                 105                 110

Trp Gly Gln Gly Thr Ser Val Thr Val Ser Ser
        115                 120
```

<210> SEQ ID NO 116
<211> LENGTH: 5
<212> TYPE: PRT
<213> ORGANISM: Mus musculus

<400> SEQUENCE: 116

```
Ser Tyr Trp Met Asn
1               5
```

<210> SEQ ID NO 117
<211> LENGTH: 17
<212> TYPE: PRT
<213> ORGANISM: Mus musculus

<400> SEQUENCE: 117

```
Arg Ile His Pro Ser Asp Ser Glu Thr His Tyr Asn Gln Lys Phe Lys
1               5                   10                  15

Ser
```

<210> SEQ ID NO 118
<211> LENGTH: 14
<212> TYPE: PRT
<213> ORGANISM: Mus musculus

<400> SEQUENCE: 118

```
Tyr Gly Leu Phe Tyr Gly Asn Asp Gly Tyr Ala Met Asp His
1               5                   10
```

<210> SEQ ID NO 119
<211> LENGTH: 355
<212> TYPE: DNA
<213> ORGANISM: Mus musculus

<400> SEQUENCE: 119
caggtccaac tgcagcagcc tggggctgaa ctggtgaagc ctggggcttc agtgaagctg      60
tcctgcaagg cttctggcta ctctttcacc agctactgga tgaactgggt gaagcagagg     120
cctggacgag gcctcgagtg gattggaagg attcatcctt ctgatagtga aactcactac     180
aatcaaaagt tcaagagcaa ggccacactg actgtagaca atcctccag cacagcctac      240 atccaactca gcagcctgac atctgaggac tctgcggtct attttgtgc aagatacggg      300 ctcttctatg gtaacgacgg atatgctatg gaccactggg gtcaaggaac ctcag          355

<210> SEQ ID NO 120
<211> LENGTH: 107
<212> TYPE: PRT
<213> ORGANISM: Mus musculus

<400> SEQUENCE: 120

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Phe Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 121
<211> LENGTH: 11
<212> TYPE: PRT
<213> ORGANISM: Mus musculus

<400> SEQUENCE: 121

Arg Ala Ser Gln Asp Ile Ser Phe Tyr Leu Asn
1               5                   10

<210> SEQ ID NO 122
<211> LENGTH: 321
<212> TYPE: DNA
<213> ORGANISM: Mus musculus

<400> SEQUENCE: 122
gatatccaga tgacacagac tacatcctcc ctgtctgcct ctctgggaga cagagtcacc      60
atcagttgca gggcaagtca ggacattagc ttttatttaa actggtatca gcagaaacca    120
gatggaactg ttaaactcct gatctactac acatcaagat tacactcagg agtcccatca    180
aggttcagtg gcagtgggtc tggaacagat tattctctca ccattagcaa cctggagcaa    240
gaagatattg ccacttactt ttgccaacag ggtaatacac ttccgtggac gttcggtgga    300

```
ggcaccaagc tggaaatcaa a                                              321
```

<210> SEQ ID NO 123
<211> LENGTH: 116
<212> TYPE: PRT
<213> ORGANISM: Mus musculus

<400> SEQUENCE: 123

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Arg Val Asn Pro Ser Asn Gly Gly Thr Ser Tyr Asn Gln Lys Phe
    50                  55                  60

Lys Gly Lys Ala Thr Leu Thr Val Asp Lys Ser Leu Ser Ala Ala Tyr
65                  70                  75                  80

Met Gln Leu Asn Ser Leu Thr Ser Glu Asp Ser Ala Val Tyr Tyr Cys
                85                  90                  95

Ala Arg Arg His Asn Tyr Pro Asp Tyr Trp Gly Gln Gly Thr Thr Leu
            100                 105                 110

Thr Val Ser Ser
        115
```

<210> SEQ ID NO 124
<211> LENGTH: 17
<212> TYPE: PRT
<213> ORGANISM: Mus musculus

<400> SEQUENCE: 124

```
Arg Val Asn Pro Ser Asn Gly Gly Thr Ser Tyr Asn Gln Lys Phe Lys
1               5                   10                  15

Gly
```

<210> SEQ ID NO 125
<211> LENGTH: 7
<212> TYPE: PRT
<213> ORGANISM: Mus musculus

<400> SEQUENCE: 125

```
Arg His Asn Tyr Pro Asp Tyr
1               5
```

<210> SEQ ID NO 126
<211> LENGTH: 348
<212> TYPE: DNA
<213> ORGANISM: Mus musculus

<400> SEQUENCE: 126

```
gaggtccagc tgcaacagtc tggacctgaa ctggtgaagc ctggggcttc agtgaagatg     60
tcctgtaagg cttctggata cacattcact gactactaca tgaactgggt gaagcagagt    120
catggaaaga gccttgagtg gattggacgt gttaatccta gcaatggtgg tactagctac    180
aaccagaagt tcaagggcaa ggccacattg acagtagaca atccctcag cgcagcctat     240 atgcagctca acagcctgac atctgaggac tctgcggtct attactgtgc aagaaggcat    300
aactaccctg actactgggg ccaaggcacc actctcacag tctcctca                 348
```

-continued

<210> SEQ ID NO 127
<211> LENGTH: 320
<212> TYPE: DNA
<213> ORGANISM: Mus musculus

<400> SEQUENCE: 127

```
gaaatccaga tgacccagtc tccatcctct atgtctgcat ctctgggaga cagaataacc      60
atcacttgcc aggcaactca agacattgtt aagagtttaa actggtatca acaaaaacca     120
gggaaacccc cttcattcct gatctattat acagctcaac tggcagaagg ggtcccgtca     180
aggttcagtg gcagtgggtc tgggtcagac tattctctga caatcagcaa cctggagtct     240
gaagattttg cagactatta ctgtctacag ttttatgagt ttcctccgac gttcggtgga     300
ggcaccaagc tggaaatcaa                                                 320
```

<210> SEQ ID NO 128
<211> LENGTH: 117
<212> TYPE: PRT
<213> ORGANISM: Mus musculus

<400> SEQUENCE: 128

```
Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Pro Phe Thr Ser Tyr
            20                  25                  30

Trp Met His Trp Val Lys Gln Arg Pro Gly Gln Gly Leu Glu Trp Ile
        35                  40                  45

Gly Ala Ile Tyr Pro Gly Asn Ser Asp Thr Arg Tyr Asn Pro Asn Phe
    50                  55                  60

Lys Gly Lys Ala Asn Leu Thr Ala Val Thr Ser Ala Thr Thr Ala Tyr
65                  70                  75                  80

Met Glu Leu Ser Ser Leu Thr Asn Glu Glu Ser Ala Val Tyr Tyr Cys
                85                  90                  95

Thr Ser Thr Trp Thr His Tyr Phe Asp Tyr Trp Gly Gln Gly Thr Thr
            100                 105                 110

Leu Thr Val Ser Ser
        115
```

<210> SEQ ID NO 129
<211> LENGTH: 17
<212> TYPE: PRT
<213> ORGANISM: Mus musculus

<400> SEQUENCE: 129

```
Ala Ile Tyr Pro Gly Asn Ser Asp Thr Arg Tyr Asn Pro Asn Phe Lys
1               5                   10                  15

Gly
```

<210> SEQ ID NO 130
<211> LENGTH: 8
<212> TYPE: PRT
<213> ORGANISM: Mus musculus

<400> SEQUENCE: 130

```
Thr Trp Thr His Tyr Phe Asp Tyr
1               5
```

<210> SEQ ID NO 131
<211> LENGTH: 351
<212> TYPE: DNA

```
<213> ORGANISM: Mus musculus

<400> SEQUENCE: 131
gaggttcagc tccagcagtc tgggactgtg ctggcaaggc ctggggcttc agtgaagatg        60
tcctgcaagg cttctggcta cccctttacc agctactgga tgcactgggt aaagcagagg       120
cctggacagg gtctggaatg gattggcgct atttatcctg gaaatagtga tactaggtac       180
aacccgaatt tcaagggcaa ggccaacctg actgcagtca catctgccac cactgcctac       240
atggagctca gcagcctgac aaatgaggaa tctgcggtct attactgtac aagtacctgg       300
acccactact ttgactactg gggccaaggc accactctca cagtctcctc a                351
```

B7-H4 ANTIBODIES AND METHODS OF USE THEREOF

CROSS REFERENCE TO RELATED APPLICATIONS

This application is a national stage application, filed under 35 U.S.C. § 371, of International Patent Application No. PCT/US2019/014748 filed on Jan. 23, 2019, which claims benefit of and priority to U.S. Provisional Application No. 62/620,545 filed on Jan. 23, 2018, all of which are incorporated by reference in their entireties where permissible.

REFERENCE TO A SEQUENCE LISTING

The Sequence Listing submitted Jan. 23, 2019 as a text file named "064467.005PCT_seqlist_ST25" created on Jan. 23, 2019, and having a size of 357 MB is hereby incorporated by reference pursuant to 37 C.F.R. § 1,52 (e)(5).

FIELD OF THE INVENTION

The invention is generally related to the field of immunomodulation, and more particularly to compositions and methods for modulating B7-H4 signaling to increase or decrease an immune response.

BACKGROUND OF THE INVENTION

The B7 family plays an important role in both positive and negative regulation of immune responses by engaging a variety of receptors on lymphocytes (Rahbar, R. et al., Cancer Immunol Res, 3(2):184-195(2015)). B7-H4 (also referred to as VTCN1 or B7x or B7S1) is a member of the B7 family and inhibits T-cell function. It is also upregulated on a variety of tumors and has been proposed to promote tumor growth. High B7-H4 expression is found in numerous tumor tissues providing a correlation of the level of expression on tumor cells with adverse clinical and pathologic features, including tumor aggressiveness The biological activity of B7-H4 has been associated with decreased inflammatory $CD4^+$ T-cell responses and a correlation between B7-H4-expressing tumor-associated macrophages and FoxP3+ regulatory T cells (Tregs) within the tumor microenvironment. Since B7-H4 is expressed on tumor cells and tumor-associated macrophages in various cancer types, therapeutic blockade of B7-H4 could favorably alter the tumor microenvironment allowing for antigen-specific clearance of tumor cells (Podojil, J R. and Miller, S D, Immunol Rev, 276(1):40-51 (2017)).

cDNA encoding the human B7-H4 protein was identified and cloned from placental cDNA (Sica, G. L. et al. (2003) "B7-H4, A Molecule Of The B7 Family, Negatively Regulates T Cell Immunity," Immunity 18:849-861; Zang, X. et al. (2003) B7x: A Widely Expressed B7 Family Member That Inhibits T Cell Activation," Proc. Natl. Acad. Sci. (USA) 100:10388-10392). B7-H4 is discussed in U.S. Pat. Nos. 7,931,896; 7,875,702; 7,847,081; and 7,622,565.

Anti-B7-H4 antibodies are disclosed in U.S. Pat. Nos. 9,574,000; 7,888,477; 7,737,255; 7,619,068; and 6,962,980.

Human B7-H4 protein possesses 282 amino acid residues, which have been categorized as including an amino terminal extracellular domain, a large hydrophobic transmembrane domain and a very short intracellular domain (consisting of only 2 amino acid residues). Like other B7 family members, B7-H4 possesses a pair of Ig-like regions in its extracellular domain. The B7-H4 protein has an overall structure of a type I transmembrane protein. The protein has minimal (about 25%) homology with other B7 family members (Zang, X. et al. (2003) "B7x: A Widely Expressed B7 Family Member That Inhibits T Cell Activation," Proc. Natl. Acad. Sci. (USA) 100:10388-10392).

B7-H4 is also expressed on tumor-associated macrophages (TAMs). TAMs inhibit anti-tumor immune responses through the release of humoral mediators and also protect tumors from immune recognition by hampering cell-mediated immune responses through the cell-surface expression of inhibitory molecules such as B7-H4. TAMs derive from resident macrophages or from monocytes recruited by the tumor microenvironment and polarized at the tumor site. Tumor infiltration with TAMs has been associated with poor patient survival and targeting TAMs represents a promising strategy against cancer. Several approaches have already been developed, including depletion with clodronate liposomes; tumor recruitment inhibition by CF SR-1 and CCL2 targeting; and "re-education" through activation via anti-CD40 mAbs, or HRG plasma protein, or mannose receptor (Dangai, D. et al., Cancer Res, 73(15): 4820-4829 (2013)).

Since B7-H4 is expressed on tumor cells and TAMs in various cancer types, directing therapeutics against B7-H4 could have tremendous synergistic outcomes in favorably altering the tumor micro-environment and eliminating cancer cells. Thus, there is a need for new immunomodulators of B7-H4.

Therefore, it is an object of the invention to provide compositions that inhibit B7-H4 mediated inhibitory signal transduction to thereby enhance or promote an immunological response by inhibiting B7-H4 suppressive signal transduction. Such compositions are useful for the treatment of cancer and infectious diseases.

It is another object of the invention to provide compositions that increase B7-H4 mediated inhibitory signal transduction thereby promoting a suppressive immunological response.

SUMMARY OF THE INVENTION

Compositions and methods of their use for modulating B7-H4 signal transduction are provided. Such compositions are useful for the treatment of inflammatory diseases and disorders and autoimmune diseases. In one embodiment immunomodulatory agents are provided that reduce B7-H4 expression, ligand binding, crosslinking, signal transduction, or a combination thereof. In one embodiment, the immunomodulatory agents specifically bind to B7-H4. The immunomodulatory agents can be antibodies or antigen binding fragments thereof, fusion proteins, aptamers, or agents that specifically bind B7-H4 and modulate signal transduction through B7-H4 signal transduction pathway. Modulation includes increasing signal transduction through the B7-H4 signal transduction pathway or inhibing signal transduction through the B7-H4 signal transduction pathway.

One embodiment provides a method for treating infection in a subject in need thereof by administering an effective amount of an agent that inhibits or blocks B7-H4 suppressive immune response in an amount effective to expand neutrophils and/or increase innate immunity. The disclosed agents can be used to increase an immune response in a subject in need thereof by inhibiting the B7-H4 suppressive immune response. An immune response can be, for example, a primary immune response to an antigen or an increase in effector cell function such as increasing antigen-specific proliferation of T cells, enhancing cytokine production by T cells, stimulating differentiation, neutrophil expansion, or a combination thereof. Exemplary agents include (i) a soluble B7-H4 polypeptide or fusion protein, (ii) a function blocking anti-B7-H4 antibody, (iii) an antibody that can be used to deplete B7-H4 positive cells, and (iv) combinations thereof. In some embodiments, the immunomodulatory agent is an antagonist of B7-H4.

In particular embodiments the agent is a B7-H4 fusion protein, for example a fusion protein that includes an extracellular domain of B7-H4 or functional variant thereof linked to an immunoglobulin domain. An exemplary fusion protein includes the amino acid sequence of SEQ ID NO:1 or a fragment thereof.

In other embodiments the agent is a B7-H4 protein or a functional fragment or variant thereof. For example, the B7-H4 protein or functional fragment or variant thereof can have at least 80%, 90%, 95%, or 100% sequence identity to SEQ ID NO:1. In one embodiment, the B7-H4 proteins or polypeptides modulate signal transduction through the B7-H4 signal transduction pathway by specifically binding to a ligand of B7-H4.

In other embodiments the agent is a soluble B7-H4 protein or a functional fragment or variant thereof. For example, the soluble B7-H4 protein can consist of an extracellular domain of B7-H4 or a functional fragment or variant thereof.

Methods of increasing an immune response in a subject typically include administering to a subject in need thereof an effective amount of an immunomodulatory agent that reduces B7-H4 expression, ligand binding, crosslinking, signal transduction, or a combination thereof. The subject can have, for example, cancer or an infectious disease.

In some embodiments, the subject, the cancer, or the disease is characterized by increased expression of B7-H4, increased expression of a B7-H4 ligand, or a combination thereof. In particular embodiments, the cancer is an ovarian, breast, lung, thyroid, gastrointestinal cancer, acute myeloid leukemia (AML), acute lymphoid leukemia (ALL), endometrial cancer, brain cancer, head and neck cancer, pancreatic cancer, and bladder cancer. The agent can be administered contemporaneously or in combination with a vaccine or a component thereof.

Immunomodulatory agents are also provided that increase B7-H4 expression, ligand binding, crosslinking, immune suppressive signaling, or a combination thereof. Such agents can be used to reduce an immune response in a subject in need thereof inducing or enhancing the suppressive immune B7-H4 response. Exemplary agents include a function activating anti-B7-H4 antibody or a soluble B7-H4 polypeptide.

Methods of reducing an immune response in a subject typically include administering a subject in need thereof an effective amount of an immunomodulatory agent that increases B7-H4 expression, ligand binding, crosslinking, negative signaling, or a combination thereof. In some embodiments, the subject has inflammation or an autoimmune disorder. In a particular embodiment, the subject has rheumatoid arthritis.

In some embodiments, the subject or the disease or condition is characterized by reduced expression of B7-H4.

Any of the disclosed methods can include administering to the subject an immunomodulatory agent alone or in combination with one or more additional therapeutic agents.

One embodiment provides a method for treating leukemia in a subject in need thereof by administering to the subject an effective amount of a pharmaceutical composition comprising a B7-H4 monoclonal antibody, soluble B7-H4 polypeptide, B7-H4 fusion protein, or combinations thereof to inhibit or reduce B7-H4 signal transduction in leukemia cells and thereby inhibit leukemia cell survival or promote an anti-tumor immune response to the leukemia cells. The leukemia can be acute myeloid leukemia.

One embodiment provides a method for assessing or predicting the efficacy of a treatment using an anti-B7-H4 binding moiety by assaying the cells of a subject in need of treatment to determine whether the cells express B7-H4, binding partners of B7-H4, or both. Exemplary cells to be assayed include, but are not limited to cancer cells obtained from the subjected. Exemplar cancer cells, include but are not limited to acute myeloid leukemia (AML) cells, endometrial cancer, brain cancer, head and neck cancer, and pancreatic cancer.

One embodiment provides an anti-B7-H4 monoclonal antibody or antigen binding fragment thereof that has a light chain having at least 50%, 60%, 70%, 80%, 85%, 90%, 95%, 99%, or 100% sequence identity to SEQ ID NO:3.

One embodiment provides a nucleic acid that encodes a light chain according to SEQ ID NO:3. Another embodiment provides a nucleic acid having at least 50%, 60%, 70%, 80%, 85%, 90%, 95%, 99%, or 100% sequence identity to SEQ ID NO:7.

One embodiment provides an anti-B7-H4 monoclonal antibody or antigen binding fragment thereof that has a heavy chain having at least 50%, 60%, 70%, 80%, 85%, 90%, 95%, 99%, or 100% sequence identity to SEQ ID NO:8.

One embodiment provides a nucleic acid encoding heavy chain SEQ ID NO:8. Another embodiment provides a nucleic acid having at least 50%, 60%, 70%, 80%, 85%, 90%, 95%, 99%, or 100% sequence identity to SEQ ID NO:12.

One embodiment provides an anti-B7-H4 antibody or antigen binding fragment thereof that has a light chain containing CDRs according to SEQ ID Nos: 4, 5, and 6.

Another embodiment provides an anti-B7-H4 antibody or an antigen binding fragment thereof having a heavy chain containing CDRs according to SEQ ID Nos: 9, 10, and 11.

In one embodiment, an anti-B7-H4 antibody or antigen binding fragment thereof has a light chain containing CDRs according to SEQ ID Nos: 4, 5, and 6 and a heavy chain containing CDRs according to SEQ ID Nos: 9, 10, and 11.

One embodiment provides an anti-B7-H4 antibody or antigen binding fragment thereof having a light chain with at least 50%, 60%, 70%, 80%, 85%, 90%, 95%, 99%, or 100% sequence identity to SEQ ID NO:3 and a heavy chain having at least 50%, 60%, 70%, 80%, 85%, 90%, 95%, 99%, or 100% sequence identity to SEQ ID NO:8.

Another embodiment provides an anti-B7-H4 monoclonal antibody or antigen binding fragment thereof that has a light chain having at least 50%, 60%, 70%, 80%, 85%, 90%, 95%, 99%, or 100% sequence identity to SEQ ID NO:13.

In one embodiment, the antibody light chain contains CDRs with amino acid sequences according to SEQ ID Nos: 14, 15, and 16.

One embodiment provides an antibody heavy chain having at least 50%, 60%, 70%, 80%, 85%, 90%, 95%, or 100% sequence identity to SEQ ID NO:29.

Another embodiment provides an antibody heavy chain containing CDRs with amino acid sequences according to SEQ ID NOs: 9, 11, and 30.

One embodiment provides an anti-B7-H4 monoclonal antibody, or antigen binding fragment thereof containing light chain CDRs according to SEQ ID Nos: 14, 15, and 16 and heavy chain CDRs according to SEQ ID Nos: 9, 11, and 30.

One embodiment provides an anti-B7-H4 antibody, or antigen binding fragment thereof containing a light chain having at least 50%, 60%, 70%, 80%, 85%, 90%, 95%, 99%, or 100% sequence identity to SEQ ID NO:13 and a heavy chain having at least 50%, 60%, 70%, 80%, 85%, 90%, 95%, 99%, or 100% sequence identity to SEQ ID NO:29.

One embodiment provides an anti-B7-H4 antibody light chain having at least 50%, 60%, 70%, 80%, 85%, 90%, 95%, 99%, or 100% sequence identity to SEQ ID NO:46.

Another embodiment provides an anti-B7-H4 antibody light chain containing CDRs with amino acid sequences according to SEQ ID Nos: 14, 16, and 47.

One embodiment provides an antibody heavy chain having at least 50%, 60%, 70%, 80%, 85%, 90%, 95%, 99%, or 100% sequence identity to SEQ ID NO:49.

Another embodiment provides an antibody heavy chain containing CDRs with amino acid sequences according to SEQ ID Nos: 9, 11, and 47.

One embodiment provides an antibody, or antigen binding fragment thereof containing light chain CDRs according to SEQ ID Nos: 14, 16, and 47, and heavy chain CDRs according to SEQ ID Nos: 9, 11, and 50.

One embodiment provides an anti-B7-H4 antibody, or an antigen binding fragment thereof containing a light chain having at least 50%, 60%, 70%, 80%, 85%, 90%, 95%, 99%, or 100% sequence identity to SEQ ID NO:46 and a heavy chain having at least 50%, 60%, 70%, 80%, 85%, 90%, 95%, 99%, or 100% sequence identity to SEQ ID NO:49.

One embodiment provides an antibody light chain having at least 50%, 60%, 70%, 80%, 85%, 90%, 95%, 99%, or 100% sequence identity to SEQ ID NO:52.

In another embodiment, an antibody light chain contains CDRs with amino acid sequences according to SEQ ID Nos: 53, 54, and 55.

One embodiment provides an antibody heavy chain having at least 50%, 60%, 70%, 80%, 85%, 90%, 95%, 99%, or 100% sequence identity to SEQ ID NO:65.

Another embodiment provides an antibody heavy chain containing CDRs with amino acid sequences according to SEQ ID Nos: 66, 67, and 68.

One embodiment provides an anti-B7-H4 antibody or antigen binding fragment thereof containing light chain CDRs according to SEQ ID Nos: 53, 54, and 55, and heavy chain CDRs according to SEQ ID Nos: 66, 67, and 68.

One embodiment provides an antibody, or antigen binding fragment thereof, containing a light chain having at least 50%, 60%, 70%, 80%, 85%, 90%, 95%, 99%, or 100% sequence identity to SEQ ID NO:52 and a heavy chain having at least 50%, 60%, 70%, 80%, 85%, 90%, 95%, 99%, or 100% sequence identity to SEQ ID NO:65.

One embodiment provides an antibody light chain having at least 50%, 60%, 70%, 80%, 85%, 90%, 95%, 99%, or 100% sequence identity to SEQ ID NO:85.

Another embodiment provides an antibody light chain containing CDRs with amino acid sequences according to SEQ ID Nos: 4, 86, and 87.

One embodiment provides an antibody heavy chain having at least 50%, 60%, 70%, 80%, 85%, 90%, 95%, 99%, or 100% sequence identity to SEQ ID NO:89.

One embodiment provides an antibody heavy chain containing CDRs with amino acid sequences according to SEQ ID Nos: 9, 90, and 91.

Another embodiment provides an anti-B7-H4 antibody, or antigen binding fragment thereof, containing light chain CDRs according to SEQ ID Nos: 4, 86, and 87 and heavy chain CDRs according to SEQ ID Nos: 9, 90, and 91.

One embodiment provides an anti-B7-H4 antibody, or antigen binding fragment thereof, containing a light chain having at least 50%, 60%, 70%, 80%, 85%, 90%, 95%, 99%, or 100% sequence identity to SEQ ID NO:85 and a heavy chain having at least 50%, 60%, 70%, 80%, 85%, 90%, 95%, 99%, or 100% sequence identity to SEQ ID NO:89.

One embodiment provides an antibody light chain having at least 50%, 60%, 70%, 80%, 85%, 90%, 95%, 99%, or 100% sequence identity to SEQ ID NO:93.

Another embodiment provides an antibody light chain containing CDRs with amino acid sequences according to SEQ ID Nos: 94, 95, and 96.

One embodiment provides an antibody heavy chain having at least 50%, 60%, 70%, 80%, 85%, 90%, 95%, 99%, or 100% sequence identity to SEQ ID NO:98.

Another embodiment provides an antibody heavy chain containing CDRs with amino acid sequences according to SEQ ID Nos: 9, 99, and 100.

One embodiment provides an anti-B7-H4 antibody, or antigen binding fragment thereof, having light chain CDRs according to SEQ ID Nos: 94, 95, and 96, and heavy chain CDRs according to SEQ ID Nos: 9, 99, and 100.

One embodiment provides an anti-B7-H4 antibody, or antigen binding fragment thereof, having a light chain having at least 50%, 60%, 70%, 80%, 85%, 90%, 95%, 99%, or 100% sequence identity to SEQ ID NO:93 and a heavy chain having at least 50%, 60%, 70%, 80%, 85%, 90%, 95%, 99%, or 100% sequence identity to SEQ ID NO:98.

One embodiment provides an antibody light chain having at least 50%, 60%, 70%, 80%, 85%, 90%, 95%, 99%, or 100% sequence identity to SEQ ID NO:102.

Another embodiment provides an antibody light chain containing CDRs with amino acid sequences according to SEQ ID Nos: 103, 104, and 105.

One embodiment provides an antibody heavy chain having at least 50%, 60%, 70%, 80%, 85%, 90%, 95%, 99%, or 100% sequence identity to SEQ ID NO:107.

Another embodiment provides an antibody heavy chain containing CDRs with amino acid sequences according to SEQ ID Nos: 9, 108, and 109.

In one embodiment an anti-B7-H4 antibody or antigen binding fragment thereof, contains light chain CDRs according to SEQ ID Nos: 103, 104, and 105 and heavy chain CDRs according to SEQ ID Nos: 9, 108, and 109.

One embodiment provides an anti-B7-H4 antibody, or antigen binding fragment thereof, containing a light chain having at least 50%, 60%, 70%, 80%, 85%, 90%, 95%, 99%, or 100% sequence identity to SEQ ID NO:102 and a heavy chain having at least 50%, 60%, 70%, 80%, 85%, 90%, 95%, 99%, or 100% sequence identity to SEQ ID NO:107.

One embodiment provides an antibody light chain having at least 50%, 60%, 70%, 80%, 85%, 90%, 95%, 99%, or 100% sequence identity to SEQ ID NO:111.

Another embodiment provides an antibody light chain containing CDRs with amino acid sequences according to SEQ ID Nos: 95, 112, and 113.

One embodiment provides an antibody heavy chain having at least 50%, 60%, 70%, 80%, 85%, 90%, 95%, 99%, or 100% sequence identity to SEQ ID NO:115.

One embodiment provides an antibody heavy chain containing CDRs with amino acid sequences according to SEQ ID Nos: 116, 117, and 118.

In one embodiment, the anti-B7-H4 antibody, or antigen binding fragment thereof, contains light chain CDRs according to SEQ ID Nos: 95, 112, and 113, and heavy chain CDRs according to SEQ ID Nos: 116, 117, and 118.

One embodiment provides an anti-B7-H4 antibody, or antigen binding fragment thereof, containing a light chain having at least 50%, 60%, 70%, 80%, 85%, 90%, 95%, 99%, or 100% sequence identity to SEQ ID NO:111 and a heavy chain having at least 50%, 60%, 70%, 80%, 85%, 90%, 95%, 99%, or 100% sequence identity to SEQ ID NO:115.

One embodiment provides an antibody light chain having at least 50%, 60%, 70%, 80%, 85%, 90%, 95%, 99%, or 100% sequence identity to SEQ ID NO:120.

Another embodiment provides an antibody light chain containing CDRs with amino acid sequences according to SEQ ID Nos: 54, 55, and 121.

One embodiment provides an antibody heavy chain having at least 50%, 60%, 70%, 80%, 85%, 90%, 95%, 99%, or 100% sequence identity to SEQ ID NO:123.

Another embodiment provides an antibody heavy chain containing CDRs with amino acid sequences according to SEQ ID Nos: 66, 124, and 125.

One embodiment provides an anti-B7-H4 antibody, or antigen binding fragment thereof, containing light chain CDRs according to SEQ ID Nos: 54, 55, and 121 and heavy chain CDRs according to SEQ ID Nos: 66, 124, and 125.

One embodiment provides an anti-B7-H4 antibody, or an antigen binding fragment thereof, containing a light chain having at least 50%, 60%, 70%, 80%, 85%, 90%, 95%, 99%, or 100% sequence identity to SEQ ID NO:120 and a heavy chain having at least 50%, 60%, 70%, 80%, 85%, 90%, 95%, 99%, or 100% sequence identity to SEQ ID NO:123.

One embodiment provides an anti-B7-H4 antibody heavy chain having at least 50%, 60%, 70%, 80%, 85%, 90%, 95%, 99%, or 100% sequence identity to SEQ ID NO:128

Another embodiment provides an anti-B7-H4 antibody heavy chain containing CDRs with amino acid sequences according to SEQ ID Nos: 9, 129, and 130.

In one embodiment, an anti-B7-H4 antibody, or antigen binding fragment thereof, contains light chain CDRs according to SEQ ID Nos: 14, 15, and 16 and heavy chain CDRs according to SEQ ID Nos: 9, 129, 130.

One embodiment provides an anti-B7-H4 antibody, or antigen binding fragment thereof, containing a light chain having at least 50%, 60%, 70%, 80%, 85%, 90%, 95%, 99%, or 100% sequence identity to SEQ ID NO:13 and a heavy chain having at least 50%, 60%, 70%, 80%, 85%, 90%, 95%, 99%, or 100% sequence identity to SEQ ID NO:128.

One embodiment provides an anti-B7-H4 antibody, or an antigen binding fragment thereof having a light chain with an amino acid sequence according to any one of SEQ ID NO:3, 13, 46, 52, 85, 93, 102, 111, or 120.

Another embodiment provides an anti-B7-H4 antibody, or an antigen binding fragment thereof having a heavy chain with an amino acid sequence according to any one of SEQ ID NO:8, 29, 49, 65, 89, 98, 107, 115, 123, or 128.

One embodiment provides an anti-B7-H4 antibody, or an antigen binding fragment thereof having a light chain with an amino acid sequence according to any one of SEQ ID NOs: 3, 13, 46, 52, 85, 93, 102, 111, or 120, and a heavy chain with an amino acid sequence according to any one of SEQ ID Nos: 8, 29, 49, 65, 89, 98, 107, 115, 123, or 128.

Also provided is an anti-B7-H4 antibody, or antigen binding fragment thereof having three light chain CDRs with amino acid sequences that are selected from the group consisting of SEQ ID Nos: 4, 5, 6, 14, 15, 16, 47, 53, 54, 55, 86, 87, 94, 95, 96, 103, 104, 105, 112, 113, or 121.

One embodiment provides an anti-B7-H4 antibody, or antigen binding fragment thereof having three heavy chain CDRs with amino acid sequences that are selected from the group consisting of SEQ ID Nos: 9, 10, 11, 30, 50, 66, 67, 68, 90, 91, 99, 100, 108, 109, 116, 117, 118, 124, 125, 129, or 130.

One embodiment provides an anti-B7-H4 antibody, or antigen binding fragment thereof having three light chain CDRs with amino acid sequences that are selected from the group consisting of SEQ ID NOs: 4, 5, 6, 14, 15, 16, 47, 53, 54, 55, 86, 87, 94, 95, 96, 103, 104, 105, 112, 113, and 121, and three heavy chain CDRs with amino acid sequences that are selected from the group consisting of SEQ ID NOs: 9, 10, 11, 30, 50, 66, 67, 68, 90, 91, 99, 100, 108, 109, 116, 117, 118, 124, 125, 129, and 130.

Another embodiment provides an anti-B7-H4 antibody or antigen binding fragment thereof having a light chain variable domain having at least 50%, 60%, 70%, 80%, 85%, 90%, 95%, 99%, or 100% sequence identity to any one of SEQ ID NOs:19, 20, 21, 22, or 23, and a heavy chain variable domain having at least 50%, 60%, 70%, 80%, 85%, 90%, 95%, 99%, or 100% sequence identity to any one of SEQ ID NOs:34, 35, 36, or 37.

One embodiment provides an an anti-B7-H4 ntibody or antigen binding fragment thereof having a light chain having an amino acid sequence according to any one of SEQ ID NOs: 24, 25, 26, 27, or 28, and a heavy chain having an amino acid sequence according to any one of SEQ ID NOs: 38, 39, 40, or 41.

Another embodiment provides an anti-B7-H4 antibody or antigen binding fragment thereof having a light chain having an amino acid sequence according to any one of SEQ ID NOs: 24, 25, 26, 27, or 28, and a heavy chain having an amino acid sequence according to any one of SEQ ID NOs: 42, 43, 44, or 45.

Also provided is an anti-B7-H4 antibody or antigen binding fragment thereof having a light chain variable domain having at least 50%, 60%, 70%, 80%, 85%, 90%, 95%, 99%, or 100% sequence identity to any one of SEQ ID NOs:58, 59, 60, or 61, and a heavy chain variable domain having at least 50%, 60%, 70%, 80%, 85%, 90%, 95%, 99%, or 100% sequence identity to any one of SEQ ID NOs: 70, 71, 72, 73, or 74.

One embodiment provides an anti-B7-H4 antibody or antigen binding fragment thereof having a light chain having an amino acid sequence according to any one of SEQ ID NOs: 62, 63, or 64, and a heavy chain having an amino acid sequence according to any one of SEQ ID NOs: 75, 76, 77, 78, or 79.

One embodiment provides an anti-B7-H4 antibody or antigen binding fragment thereof having a light chain having an amino acid sequence according to any one of SEQ ID NOs: 62, 63, or 64, and a heavy chain having an amino acid sequence according to any one of SEQ ID NOs: 80, 81, 82, 83, or 84.

Another embodiment provides an anti-B7-H4 antibody or antigen binding fragment thereof having six complementarity determining regions (CDRs), wherein the CDRs include the three light chain CDRs of a polypeptide selected from the group consisting of SEQ ID NO:4, 5, 6, 14, 15, 16, 49, 55, 56, 57, 88, 89, 96, 97, 97, 105, 106, 107, 114, 115, or 123, or a variant thereof comprising at least 50%, 60%, 70%, 80%, 85%, 90%, 95%, 99%, or more sequence identity to SEQ ID N04, 5, 6, 14, 15, 16, 49, 55, 56, 57, 88, 89, 96, 97, 97, 105, 106, 107, 114, 115, or 123, and the three heavy chain CDRs of a polypeptide selected from the group consisting of SEQ ID NO:9, 10, 11, 31, 52, 68, 69, 70, 92, 93, 101, 102, 118, 119, 120, 126, 127, 131, or 132, or a variant thereof comprising at least 50%, 60%, 70%, 80%, 85%, 90%, 95%, 99%, or more sequence identity to SEQ ID NO: 9, 10, 11, 31, 52, 68, 69, 70, 92, 93, 101, 102, 118, 119, 120, 126, 127, 131, or 132, and wherein the antibody or antigen binding fragment thereof binds to B7-H4.

Another embodiment provides an anti-B7-H4 antibody or antigen binding fragment thereof having two light chains and two heavy chains, wherein the two light chains include a polypeptide selected from the group consisting of SEQ ID NO: 24, 25, 26, 27, 28, 62, 63, or 64, or a variant thereof having at least 50%, 60%, 70%, 80%, 85%, 90%, 95%, 99%, or more sequence identity to SEQ ID NO: 24, 25, 26, 27, 28, 62, 63, or 64, and the two heavy chains include a polypeptide selected from the group consisting of SEQ ID NO: 38, 39, 40, 41, 75, 76, 77, 78, or 79, or a variant thereof having at least 50%, 60%, 70%, 80%, 85%, 90%, 95%, 99%, or more sequence identity to SEQ ID NO: 38, 39, 40, 41, 75, 76, 77, 78, or 79, and wherein the antibody or antigen binding fragment thereof binds to B7-H4.

One embodiment provides an anti-B7-H4 antibody or antigen binding fragment thereof having two light chains and two heavy chains, wherein the two light chains include a polypeptide selected from the group consisting of SEQ ID NO: 24, 25, 26, 27, 28, 62, 63, or 64, or a variant thereof having at least 50%, 60%, 70%, 80%, 85%, 90%, 95%, 99%, or more sequence identity to SEQ ID NO: 24, 25, 26, 27, 28, 62, 63, or 64, and the two heavy chains include a polypeptide selected from the group consisting of SEQ ID NO: 42, 43, 44, 45, 80, 81, 82, 83, or 84, or a variant thereof having at least 50%, 60%, 70%, 80%, 85%, 90%, 95%, 99%, or more sequence identity to SEQ ID NO: 42, 43, 44, 45, 80, 81, 82, 83, or 84, and wherein the antibody or antigen binding fragment thereof binds to B7-H4.

One embodiment provides an anti-B7-H4 antibody or antigen binding fragment thereof having two light chains and two heavy chains, wherein the two light chains include a polypeptide selected from the group consisting of SEQ ID NO: 24, 25, 26, 27, or 28, or a variant thereof having at least 50%, 60%, 70%, 80%, 85%, 90%, 95%, 99%, or more sequence identity to SEQ ID NO: 24, 25, 26, 27, or 28, and the two heavy chains include a polypeptide selected from the group consisting of SEQ ID NO: 38, 39, 40, or 41, or a variant thereof having at least 50%, 60%, 70%, 80%, 85%, 90%, 95%, 99%, or more sequence identity to SEQ ID NO: 38, 39, 40, or 41, and wherein the antibody or antigen binding fragment thereof binds to B7-H4.

Another embodiment provides an anti-B7-H4 antibody or antigen binding fragment thereof having two light chains and two heavy chains, wherein the two light chains include a polypeptide selected from the group consisting of SEQ ID NO: 24, 25, 26, 27, or 28, or a variant thereof having at least 50%, 60%, 70%, 80%, 85%, 90%, 95%, 99%, or more sequence identity to SEQ ID NO: 24, 25, 26, 27, or 28, and the two heavy chains include a polypeptide selected from the group consisting of SEQ ID NO: 42, 43, 44, or 45, or a variant thereof having at least 50%, 60%, 70%, 80%, 85%, 90%, 95%, 99%, or more sequence identity to SEQ ID NO: 42, 43, 44, or 45, and wherein the antibody or antigen binding fragment thereof binds to B7-H4.

One embodiment provides an anti-B7-H4 antibody or antigen binding fragment thereof having two light chains and two heavy chains, wherein the two light chains include a polypeptide selected from the group consisting of SEQ ID NO: 62, 63, or 64, or a variant thereof comprising at least 50%, 60%, 70%, 80%, 85%, 90%, 95%, 99%, or more sequence identity to SEQ ID NO: 62, 63, or 64, and the two heavy chains include a polypeptide selected from the group consisting of SEQ ID NO: 75, 76, 77, 78, or 79, or a variant thereof having at least 50%, 60%, 70%, 80%, 85%, 90%, 95%, 99%, or more sequence identity to SEQ ID NO: 75, 76, 77, 78, or 79, and wherein the antibody or antigen binding fragment thereof binds to B7-H4.

Another embodiment provides an anti-B7-H4 antibody or antigen binding fragment thereof having two light chains and two heavy chains, wherein the two light chains include a polypeptide selected from the group consisting of SEQ ID NO: 62, 63, or 64, or a variant thereof having at least 50%, 60%, 70%, 80%, 85%, 90%, 95%, 99%, or more sequence identity to SEQ ID NO: 62, 63, or 64, and the two heavy chains include a polypeptide selected from the group consisting of SEQ ID NO: 80, 81, 82, 83, or 84, or a variant thereof having at least 50%, 60%, 70%, 80%, 85%, 90%, 95%, 99%, or more sequence identity to SEQ ID NO: 80, 81, 82, 83, or 84, and wherein the antibody or antigen binding fragment thereof binds to B7-H4.

DETAILED DESCRIPTION OF THE INVENTION

I. Definitions

As used herein, a molecule is said to be able to "immunospecifically bind" a second molecule if such binding exhibits the specificity and affinity of an antibody to its cognate antigen. Antibodies are said to be capable of immunospecifically binding to a target region or conformation ("epitope") of an antigen if such binding involves the antigen recognition site of the immunoglobulin molecule. An antibody that immunospecifically binds to a particular antigen may bind to other antigens with lower affinity if the other antigen has some sequence or conformational similarity that is recognized by the antigen recognition site as determined by, e.g., immunoassays, BIACORE® assays, or other assays known in the art, but would not bind to a totally unrelated antigen. In some embodiments, however, antibodies (and their antigen binding fragments) will not cross-react with other antigens. Antibodies may also bind to other molecules in a way that is not immunospecific, such as to FcR receptors, by virtue of binding domains in other regions/domains of the molecule that do not involve the antigen recognition site, such as the Fc region.

As used herein, a molecule is said to "physiospecifically bind" a second molecule if such binding exhibits the specificity and affinity of a receptor to its cognate binding ligand. A molecule can be capable of physiospecifically binding to more than one other molecule.

As used herein, the term "antibody" is intended to denote an immunoglobulin molecule that possesses a "variable region" antigen recognition site and include antigen-binding fragments of antibodies. The term "variable region" is intended to distinguish such domain of the immunoglobulin from domains that are broadly shared by antibodies (such as an antibody Fc domain). The variable region includes a "hypervariable region" whose residues are responsible for antigen binding. The hypervariable region includes amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, MD (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, *J. Mol. Biol.* 196:901-917). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies (See e.g., Muyldermans et al., 2001, *Trends Biochem. Sci.* 26:230; Nuttall et al., 2000, *Cur. Pharm. Biotech.* 1:253; Reichmann and Muyldermans, 1999, *J. Immunol. Meth.* 231:25; International Publication Nos. WO 94/04678 and WO 94/25591; U.S. Pat. No. 6,005,079), single-chain Fvs (scFv) (see, e.g., see Pluckthun in *The Pharmacology of Monoclonal Antibodies*, vol. 113, Rosenburg and Moore eds. Springer-Verlag, New York, pp. 269-315 (1994)), single chain antibodies, disulfide-linked Fvs (sdFv), intrabodies, diabodies, triabodies, tetrabodies, Bis-scFv, minibodies, Fab2, Fab3 and anti-idiotypic (anti-Id) antibodies (including, e.g., anti-Id and anti-anti-Id antibodies to antibodies). In particular, such antibodies include immunoglobulin molecules of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

As used herein, the term "antigen binding fragment" of an antibody refers to one or more portions of an antibody that contain the antibody's Complementarity Determining Regions ("CDRs") and optionally the framework residues that include the antibody's "variable region" antigen recognition site, and exhibit an ability to immunospecifically bind antigen. Such fragments include Fab', $F(ab')_2$, Fv, single chain (ScFv), and mutants thereof, naturally occurring variants, and fusion proteins including the antibody's "variable region" antigen recognition site and a heterologous protein (e.g., a toxin, an antigen recognition site for a different antigen, an enzyme, a receptor or receptor ligand, etc.).

As used herein, the term "fragment" refers to a peptide or polypeptide including an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

As used herein the term "modulate" relates to a capacity to alter an effect, result, or activity (e.g., signal transduction). Such modulation can be agonistic or antagonistic. Antagonistic modulation can be partial (i.e., attenuating, but not abolishing) or it can completely abolish such activity (e.g., neutralizing). Modulation can include internalization of a receptor following binding of an antibody or a reduction in expression of a receptor on the target cell. Agonistic modulation can enhance or otherwise increase or enhance an activity (e.g., signal transduction). In a still further embodiment, such modulation can alter the nature of the interaction between a ligand and its cognate receptor so as to alter the nature of the elicited signal transduction. For example, the molecules can, by binding to the ligand or receptor, alter the ability of such molecules to bind to other ligands or receptors and thereby alter their overall activity. In some embodiments, such modulation will provide at least a 10% change in a measurable immune system activity, at least a 50% change in such activity, or at least a 2-fold, 5-fold, 10-fold, or at least a 100-fold change in such activity.

The term "substantially," as used in the context of binding or exhibited effect, is intended to denote that the observed effect is physiologically or therapeutically relevant. Thus, for example, a molecule is able to substantially block an activity of a ligand or receptor if the extent of blockage is physiologically or therapeutically relevant (for example if such extent is greater than 60% complete, greater than 70% complete, greater than 75% complete, greater than 80% complete, greater than 85% complete, greater than 90% complete, greater than 95% complete, or greater than 97% complete). Similarly, a molecule is said to have substantially the same immunospecificity and/or characteristic as another molecule, if such immunospecificities and characteristics are greater than 60% identical, greater than 70% identical, greater than 75% identical, greater than 80% identical, greater than 85% identical, greater than 90% identical, greater than 95% identical, or greater than 97% identical).

As used herein, the "co-stimulatory" signals encompass positive co-stimulatory signals (e.g., signals that result in enhancing an activity) and negative co-stimulatory signals (e.g., signals that result in inhibiting an activity).

The term "derivative" refers to an antibody or antigen-binding fragment thereof that immunospecifically binds to the same target of a parent or reference antibody but which differs in amino acid sequence from the parent or reference antibody or antigen binding fragment thereof by including one, two, three, four, five or more amino acid substitutions, additions, deletions or modifications relative to the parent or reference antibody or antigen binding fragment thereof. In some embodiments such derivatives will have substantially the same immunospecificity and/or characteristics, or the same immunospecificity and characteristics as the parent or reference antibody or antigen binding fragment thereof. The amino acid substitutions or additions of such derivatives can include naturally occurring (i.e., DNA-encoded) or non-naturally occurring amino acid residues. The term "derivative" encompasses, for example, chimeric or humanized variants, as well as variants having altered CH1, hinge, CH2, CH3 or CH4 regions, so as to form, for example antibodies, etc., having variant Fc regions that exhibit enhanced or impaired effector or binding characteristics.

As used herein, a "chimeric antibody" is a molecule in which different portions of the antibody are derived from different immunoglobulin molecules such as antibodies having a variable region derived from a non-human antibody and a human immunoglobulin constant region.

As used herein, the term "humanized antibody" refers to an immunoglobulin including a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they should be substantially identical to human immunoglobulin constant regions, i.e., at least about 85-99%, or about 95% or more identical. Hence, all parts of a humanized immunoglobulin, except possibly the CDR's, are substantially identical to corresponding parts of natural human immunoglobulin sequences. A humanized antibody is an antibody including a humanized light chain and a humanized heavy chain immunoglobulin. For example, a humanized antibody would not encompass a typical chimeric antibody, because, e.g., the entire variable region of a chimeric antibody is non-human.

The term "endogenous concentration" refers to the level at which a molecule is natively expressed (i.e., in the absence of expression vectors or recombinant promoters) by a cell (which cell can be a normal cell, a cancer cell or an infected cell).

As used herein, the terms "treat," "treating," "treatment" and "therapeutic use" refer to the elimination, reduction or amelioration of one or more symptoms of a disease or disorder. As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease.

As used herein, the term "prophylactic agent" refers to an agent that can be used in the prevention of a disorder or disease prior to the detection of any symptoms of such disorder or disease. A "prophylactically effective" amount is the amount of prophylactic agent sufficient to mediate such protection. A prophylactically effective amount may also refer to the amount of the prophylactic agent that provides a prophylactic benefit in the prevention of disease.

As used herein, the term "cancer" refers to a neoplasm or tumor resulting from abnormal uncontrolled growth of cells. As used herein, cancer explicitly includes leukemias and lymphomas. The term "cancer" refers to a disease involving cells that have the potential to metastasize to distal sites and exhibit phenotypic traits that differ from those of non-cancer cells, for example, formation of colonies in a three-dimensional substrate such as soft agar or the formation of tubular networks or web-like matrices in a three-dimensional basement membrane or extracellular matrix preparation. Non-cancer cells do not form colonies in soft agar and form distinct sphere-like structures in three-dimensional basement membrane or extracellular matrix preparations.

As used herein, an "immune cell" refers to any cell from the hemopoietic origin including, but not limited to, T cells, B cells, monocytes, dendritic cells, and macrophages.

As used herein, "inflammatory molecules" refer to molecules that result in inflammatory responses including, but not limited to, cytokines and metalloproteases such as including, but not limited to, IL-10, TNF-α, TGF-beta, IFN-γ, IL-18, IL-17, IL-6, IL-23, IL-22, IL-21, and MMPs.

As used herein, "valency" refers to the number of binding sites available per molecule. As used herein, the terms "immunologic," "immunological" or "immune" response is the development of a beneficial humoral (antibody mediated) and/or a cellular (mediated by antigen-specific T cells or their secretion products) response directed against a peptide in a recipient patient. Such a response can be an active response induced by administration of immunogen or a passive response induced by administration of antibody or primed T-cells. A cellular immune response is elicited by the presentation of polypeptide epitopes in association with Class I or Class II WIC molecules to activate antigen-specific CD4+ T helper cells and/or CD8+ cytotoxic T cells. The response may also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays (CD4+ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

An "immunogenic agent" or "immunogen" is capable of inducing an immunological response against itself on administration to a mammal, optionally in conjunction with an adjuvant.

As used herein, the terms "individual," "host," "subject," and "patient" are used interchangeably herein, and refer to a mammal, including, but not limited to, humans, rodents, such as mice and rats, and other laboratory animals.

As used herein, the term "polypeptide" refers to a chain of amino acids of any length, regardless of modification (e.g., phosphorylation or glycosylation). The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, the term "variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of the disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity.

Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Trp: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

II. Compositions

The high levels of B7-H4 expression found in numerous tumor tissues, for example, human ovarian cancers, points to a key role for B7-H4 in mediating immune suppression. Also, Tumor-Associated Macrophages (TAMs) expressing B7-H4 have been found to suppress tumor-associated antigen-specific T cell immunity (Kryczek, I. et al. (2006) "B7-H4 Expression Identifies A Novel Suppressive Macrophage Population In Human Ovarian Carcinoma," J. Exp. Med. 203(4):871-881). The intensity of B7-H4 expression in TAMs correlates significantly with Treg cell numbers in the tumor. Furthermore, B7-H4 expressed on TAMs, is associated with poor patient outcome (Kryczek, I. et al. (2006) "B7-H4 Expression Identifies A Novel Suppressive Macrophage Population In Human Ovarian Carcinoma," J. Exp. Med. 203(4):871-881). Additionally, B7-H4 can be expressed on myeloid derived suppressor cells (MDSCs) where it may exert an immune suppressive effect in viral infection (Garg, A et al. (2017) "Human Immunodeficiency Virus Type-1 Myeloid Derived Suppressor Cells Inhibit Cytomegalovirus Inflammation through Interleukin-27 and B7-H4" Sci. Rep. March 24; 7:44485). While in a study of uterine cancer, B7-H4 expression in the tumor microenvironment was associated with increased infiltration of MDSCs (Vanderstraeten, A. et al. (2014) "Mapping the immunosuppressive environment in uterine tumors: implications for immunotherapy," Cancer Immunol. Immunother. June; 63(6):545-57). Therefore, B7-H4 may be expressed on tumor cells, TAM and/or MDSCs where it may exert immune suppressive signaling in cancer.

Neutrophils are a major component of the host innate defense against infection and also contribute to autoimmune pathogenesis and chronic inflammation. During infection, neutrophils rapidly migrate to sites of inflammation, become activated, and initiate a cascade of defense mechanisms including phagocytosis, killing, and degradation of microorganisms by antimicrobial and proteolytic proteins, along with the generation of reactive oxygen species. Neutrophils also participate in tissue breakdown, remodeling, wound healing, and modulation of other inflammatory and adaptive immune components. Due to their short life span, neutrophils have to be resupplied continuously during infection and inflammation by expansion from myeloid progenitor cells in the bone marrow. In vitro B7-H4 inhibits the growth of bone marrow-derived neutrophil progenitors, suggesting an inhibitory function of B7-H4 in neutrophil expansion (Zhu, G. et al., Blood, 113:1759-1767 (2009)). Thus, compositions that modulate B7-H4 signal transduction are provided.

A. B7-114 Sequences

One embodiment provides B7-H4 polypeptides. The polypeptides can include an amino acid sequence of full-length B7-H4, or a fragment or variant thereof, or a fusion protein thereof.

One embodiment provides human B7-H4 proteins or polypeptides thereof. Sequences for human B7-H4 are known in the art. For example, a consensus sequence for B7-H4 is

```
  1 MASLGQILFW SIISIIIILA GAIALIIGFG ISGRHSITVT TVASAGNIGE DGILSCTFEP

61 DIKLSDIVIQ WLKEGVLGLV HEFKEGKDEL SEQDEMFRGR TAVFADQVIV GNASLRLKNV

121 QLTDAGTYKC YIITSKGKGN ANLEYKTGAF SMPEVNVDYN ASSETLRCEA PRWFPQPTVV

181 WASQVDQGAN FSEVSNTSFE LNSENVTMKV VSVLYNVTIN NTYSCMIEND IAKATGDIKV

241 TESEIKRRSH LQLLNSKASL CVSSFFAISW ALLPLSPYLM LK
```

(SEQ ID NO:1, Q7Z7D3 (VTCN1 HUMAN)), where amino acids 1-27 are a signal sequence (underlined according to US Patent Publication No. 2016/0039905 which is incorporated by referenced in its entirety). Sica et al. indicated that amino acids 1-20 comprise the signal sequence. UniProtKB accession #Q7Z7D3 indicates that the extracellular domain includes amino acids 25-259.

Another embodiment provides mouse B7-H4 proteins and polypeptides. Sequences for mouse B7-H4 are known in the art. For example, a consensus sequence for mouse B7-H4 is

```
MASLGQIIFWSIINIIIILAGAIALIIGFGISGKHFITVTTFTSAGNIGE

DGTLSCTFEPDIKLNGIVIQWLKEGIKGLVHEFKEGKDDLSQQHEMERGR

TAVFADQVVVGNASLRLKNVQLTDAGTYTCYIRTSKGKGNANLEYKTGAF

SMPEINVDYNASSESLRCEAPRWFPQPTVAWASQVDQGANFSEVSNTSFE

LNSENVTMKVVSVLYNVTINNTYSCMIENDIAKATGDIKVTDSEVKRRSQ

LQLLNSGPSPCVFSSAFVAGWALLSLSCCLMLR
```

(SEQ ID NO:2, Q7TSP5 (VTCN1 MOUSE) which is incorporated by reference in its entirety.)

1. Anti-B7-114 Antibody Sequences a. B1A1 Sequences

One embodiment provides a murine monoclonal antibody is produced by hybridoma clone B1A1 contains two light chains and two heavy chains and specifically binds to B7-H4.

i. Light Chain

One embodiment provides a murine monoclonal antibody or antigen binding fragment thereof that has a light chain having at least 50%, 60%, 70%, 80%, 85%, 90%, 95%, 99%, or 100% sequence identity with the following amino acid sequence:

```
                                                (SEQ ID NO: 3)
DIVMTQSHKFMSTSVGDRVSITCKASQDVRTAVAWYQQKPGQSPKLLIYS

TSYRYTGVPDRFTGSGSGTEFTFTISSVQAEDLAVYYCQQYYVTPLTFGA

GTKLELK
``` that specifically binds to B7-H4.

The CDRs are of SEQ ID NO:3 are bolded and underlined and are:

| CDR1 | KASQDVRTAVA; | (SEQ ID NO: 4) |
|------|--------------|----------------|
| CDR2 and | STSYRYT; | (SEQ ID NO: 5) |
| CDR3 | QQYYVTPLT. | (SEQ ID NO: 6) |

Another embodiment provides a nucleic acid that encodes the light chain (SEQ ID NO:3).

An exemplary nucleic acid that encodes light chain (SEQ ID NO:3) is

```
                                                (SEQ ID NO: 7)
GACATTGTGATGACCCAGTCTCACAAATTCATGTCCACATCAGTAGGAGA

CAGGGTCAGTATCACCTGCAAGGCCAGTCAGGATGTGAGAACTGCTGTAG

CCTGGTATCAACAGAAACCAGGACAATCTCCTAAACTACTGATTTACTCG

ACATCCTACCGGTACACTGGAGTCCCTGATCGCTTCACTGGCAGTGGATC

TGGGACGGAATTCACTTTCACCATCAGCAGTGTGCAGGCTGAAGACCTGG

CAGTTTATTACTGTCAGCAATATTATGTTACTCCGCTCACGTTCGGTGCT

GGGACCAAGCTGGAGCTGAAA.
``` ii. Heavy Chain

One embodiment provides a murine monoclonal antibody or antigen binding fragment thereof that has a heavy chain having at least 50%, 60%, 70%, 80%, 85%, 90%, 95%, 99%, or 100% sequence identity with the following amino acid sequence:

```
EVQLQQSGTVLARPGASVKMSCKASGYTFTSYWMHWIKQRPGQGLEWIGA

IYPGNSDTKYNQKFKDKAKLTAVTSASTAYMELSSLTNEDSAVYYCTSTV

RNVMDYWGQGTSV
```

TVSS (SEQ ID NO:8) and specifically binds to B7-H4.

The CDRs of SEQ ID NO:8 are bolded and underlined and are:

| CDR1 | SYWMH; | (SEQ ID NO: 9) |
|---|---|---|
| CDR2 and | AIYPGNSDTKYNQKFKDK; | (SEQ ID NO: 10) |
| CDR3 | TVRNVMDY. | (SEQ ID NO: 11) |

Another embodiment provides a nucleic acid encoding heavy chain (SEQ ID NO:8). An exemplary nucleic acid that encodes heavy chain (SEQ ID NO:8) is (SEQ ID NO: 12)
GAGGTTCAGCTCCAGCAGTCTGGGACTGTGCTGGCAAGGCCTGGGGCTTC

AGTGAAGATGTCCTGCAAGGCTTCTGGCTACACCTTTACCAGCTACTGGA

TGCACTGGATAAAACAGAGGCCTGGACAGGGTCTGGAATGGATTGGCGCT

ATTTATCCTGGAAATAGTGATACTAAATACAACCAGAAGTTCAAGGACAA

GGCCAAACTGACTGCAGTCACATCTGCCAGCACTGCCTACATGGAGCTCA

GCAGCCTGACAAATGAGGACTCTGCGGTCTATTACTGTACATCTACGGTA

CGGAATGTTATGGACTACTGGGGTCAAGGAACCTCAGTCACCGTCTCCTC

A.

One embodiment provides an antibody, preferably a monoclonal antibody, or antigen binding fragment thereof that has a light chain having CDRs according to SEQ ID Nos: 4, 5, and 6 and specifically binds to B7-H4.

One embodiment provides an antibody, preferably a monoclonal antibody, or an antigen binding fragment thereof having a heavy chain having CDRs according to SEQ ID Nos: 9, 10, and 11 and specifically binds to B7-H4.

One embodiment provides an antibody, preferably a monoclonal antibody, or antigen binding fragment thereof that has a light chain having CDRs according to SEQ ID Nos: 4, 5, and 6 and a heavy chain having CDRs according to SEQ ID Nos: 9, 10, and 11 and specifically binds to B7-H4.

One embodiment provides an antibody, preferably a monoclonal antibody, or an antigen binding fragment thereof having a light chain with at least 50%, 60%, 70%, 80%, 85%, 90%, 95%, 99%, or 100% sequence identity to SEQ ID NO:3 and a heavy chain having at least 50%, 60%, 70%, 80%, 85%, 90%, 95%, 99%, or 100% sequence identity to SEQ ID NO:8 and specifically binds to B7-H4.

b. B1H1 Sequences

In one embodiment a murine monoclonal antibody is produced by hybridoma clone B1H1 and contains two light chains and two heavy chains.

i. Light Chain

One embodiment provides a murine monoclonal antibody or antigen binding fragment thereof that has a light chain having at least 50%, 60%, 70%, 80%, 85%, 90%, 95%, 99%, or 100% sequence identity with the following amino acid sequence:

(SEQ ID NO: 13)
EIQMTQSPSSMSASLGDRITITCQATQDIVKSLNWYQQKPGKPPSFLIYY

TAQLAEGVPSRFSGSGSGSDYSLTISNLESEDFADYYCLQFYEFPPTFGG

GTKLEIK.

The CDRs are of SEQ ID NO:13 are bolded and underlined and are:

| CDR1 | QATQDIVKSLN; | (SEQ ID NO: 14) |
|---|---|---|
| CDR2 and | YTAQLAE; | (SEQ ID NO: 15) |
| CDR3 | LQFYEFPPT. | (SEQ ID NO: 16) |

Another embodiment provides a nucleic acid that encodes the light chain (SEQ ID NO:13).

An exemplary nucleic acid that encodes the light chain (SEQ ID NO:13) is (SEQ ID NO: 17)
GAAATCCAGATGACCCAGTCTCCATCCTCTATGTCTGCATCTCTGGGAGA

CAGAATAACCATCACTTGCCAGGCAACTCAAGACATTGTTAAGAGTTTAA

ACTGGTATCAACAAAAACCAGGGAAACCCCCTTCATTCCTGATCTATTAT

ACAGCTCAACTGGCAGAAGGGGTCCCATCAAGGTTCAGTGGCAGTGGGTC

TGGGTCAGACTATTCTCTGACAATCAGCAACCTGGAGTCTGAAGATTTTG

CAGACTATTACTGTCTACAGTTTTATGAGTTTCCTCCGACGTTCGGTGGA

GGCACCAAGCTGGAAATCAAA.

One embodiment provides a monoclonal antibody or antigen binding fragment thereof that has a light chain constant domain having at least 50%, 60%, 70%, 80%, 85%, 90%, 95%, 99%, or 100% sequence identity with the following amino acid sequence:

(SEQ ID NO: 18)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC and specifically binds to B7-H4.

ii. Humanized Light Chain

One embodiment provides an anti-B7-H4 monoclonal antibody or antigen binding fragment thereof that has a humanized light chain variable domain having at least 50%, 60%, 70%, 80%, 85%, 90%, 95%, 99%, or 100% sequence identity with one of the following amino acid sequences:

Humanized B1H1 VL1:
(SEQ ID NO: 19)
DIQMTQSPSSLSASVGDRVTITCQATQDIVKSLNWYQQKPGKPPKFLIYY

TAQLAEGVPSRFSGSGSGTDYTLTISSLQSEDFATYYCLQFYEFPPTFGG

GTKVEIK

Humanized B1H1 VL2:
(SEQ ID NO: 20)
DIQMTQSPSSLSASVGDRVTITCQATQDIVKSLNWYQQKPGKPPKFLIYY

TAQLAEGVPSRFSGSGSGTDYTLTISSLQPEDFATYYCLQFYEFPPTFGG

GTKVEIK

```
Humanized B1H1 VL3:
                                            (SEQ ID NO: 21)
DIQMTQSPSSLSASVGDRVTITCQATQDIVKSLNWYQQKPGKAPKFLIYY

TAQLAEGVPSRFSGSGSGTDYTLTISSLQPEDFATYYCLQFYEFPPTFGG

GTKVEIK

Humanized B1H1 VL4:
                                            (SEQ ID NO: 22)
DIQMTQSPSSLSASVGDRVTITCQATQDIVKSLNWYQQKPGKPPKFLIYY

TAQLAEGVPSRFSGSGSGTDFTLTISSLQPEDFATYYCLQFYEFPPTFGG

GTKVEIK

Humanized B1H1 VL5:
                                            (SEQ ID NO: 23)
DIQMTQSPSSLSASVGDRVTITCQATQDIVKSLNWYQQKPGKPPKFAIYY

TAQLAEGVPSRFSGSGSGTDYTLTISSLQPEDFATYYCLQFYEFPPTFGG

GTKVEIK
```

One embodiment provides an anti-B7-H4 monoclonal antibody or antigen binding fragment thereof that has a humanized light chain having at least 50%, 60%, 70%, 80%, 85%, 90%, 95%, 99%, or 100% sequence identity with one of the following amino acid sequences:

```
Full Length B1H1 Light chain Variant 1:
                                            (SEQ ID NO: 24)
DIQMTQSPSSLSASVGDRVTITCQATQDIVKSLNWYQQKPGKPPKFLIYY

TAQLAEGVPSRFSGSGSGTDYTLTISSLQSEDFATYYCLQFYEFPPTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Full Length B1H1 Light chain Variant 2:
                                            (SEQ ID NO: 25)
DIQMTQSPSSLSASVGDRVTITCQATQDIVKSLNWYQQKPGKPPKFLIYY

TAQLAEGVPSRFSGSGSGTDYTLTISSLQPEDFATYYCLQFYEFPPTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Full Length B1H1 Light chain Variant 3:
                                            (SEQ ID NO: 26)
DIQMTQSPSSLSASVGDRVTITCQATQDIVKSLNWYQQKPGKAPKFLIYY

TAQLAEGVPSRFSGSGSGTDYTLTISSLQPEDFATYYCLQFYEFPPTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Full Length B1H1 Light chain Variant 4:
                                            (SEQ ID NO: 27)
DIQMTQSPSSLSASVGDRVTITCQATQDIVKSLNWYQQKPGKPPKFLIYY

TAQLAEGVPSRFSGSGSGTDFTLTISSLQPEDFATYYCLQFYEFPPTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Full Length B1H1 Light chain Variant 5:
                                            (SEQ ID NO: 28)
DIQMTQSPSSLSASVGDRVTITCQATQDIVKSLNWYQQKPGKPPKFLIYY

TAQLAEGVPSRFSGSGSGTDFTLTISSLQPEDFATYYCLQFYEFPPTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
``` iii. Heavy Chain

One embodiment provides a murine monoclonal antibody or antigen binding fragment thereof that has a heavy chain having at least 50%, 60%, 70%, 80%, 85%, 90%, 95%, 99%, or 100% sequence identity with the following amino acid sequence:

```
                                            (SEQ ID NO: 29)
EVQLQQSGTVLARPGASVKMSCKVSGYPFTSYWMHWVKQRPGQGLEWIGA

IYPGKSDTEYNPNFKGKAKLTAVTSATTAYMELSSLTNEDSAVYYCTSTW

THYFDYWGQGTTLTVSS
``` and specifically binds to B7-H4.

The CDRs are of SEQ ID NO:29 are bolded and underlined and are:

```
                                            (SEQ ID NO: 9)
        CDR1 SYWMH;

(SEQ ID NO: 30)
        CDR2 AIYPGKSDTEYNPNFKG;
        and (SEQ ID NO: 11)
        CDR3 TVRNVMDY.
```

Another embodiment provides a nucleic acid encoding heavy chain (SEQ ID NO:29). An exemplary nucleic acid that encodes heavy chain (SEQ ID NO:291 is

```
                                            (SEQ ID NO: 31)
GAGGTTCAGCTCCAGCAGTCTGGGACTGTTCTGGCAAGGCCTGGGGCTTC

AGTGAAGATGTCCTGCAAGGTTTCTGGCTACCCCTTTACCAGCTACTGGA

TGCACTGGGTAAAACAGAGGCCTGGACAGGGTCTGGAATGGATTGGCGCT

ATTTATCCTGGAAAAAGTGACACTGAATACAACCCGAACTTCAAGGGCAA

GGCCAAACTGACTGCAGTCACATCTGCCACCACTGCCTACATGGAGCTCA

GCAGCCTGACAAATGAGGACTCTGCGGTCTATTACTGTACAAGTACCTGG

ACCCACTACTTTGACTACTGGGGCCAAGGCACCACTCTCACAGTCTCCTC

A.
```

One embodiment provides a murine monoclonal antibody or antigen binding fragment thereof that has a heavy chain constant domain having at least 50%, 60%, 70%, 80%, 85%, 90%, 95%, 99%, or 100% sequence identity with the following amino acid sequence: ASTKGPSVFPLAPSSKST-SGGTAALGCLVKDYFPEPVTVSWNSGALTSGVHTF-PAVLQSS GLYSLSSVVTVPSSSLGTQTYICNVNHKP-SNTKVDKKVEPKSCDKTHTCPPCPAPELLGG PSVFLFPPKPKDTLMISRTPEVTCVVVDVSHEDPE- VKFNWYVDGVEVHNAKTKPREEQY NSTYRVVSVLTVLHQDWLNGKEYKCKVSNKALP<u>AP</u>IEKTISKAKGQPREPQVYTLPPSR DELTKNQ<u>VS</u>LTCLVKGFYPSDIAVEWESNGQPENNYKTTPPVLDSDGSFFLYSKLTVDK SRWQQGNVFSCSVMHEALHNHYTQKSLSLSPGK (SEQ ID NO:32) and specifically binds to B7-H4.

The underlined and bolded amino acids represent amino acids that differ from the mutant sequence.

Another embodiment provides a mutant heavy chain constant domain having at least 50%, 60%, 70%, 80%, 85%, 90%, 95%, 99%, or 100% sequence identity with the following amino acid sequence:

(SEQ ID NO: 33)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGP<u>D</u>VFLFPPKPKDTLMISRTPEVTCVVVDVS

HEDPEVKFNWYVDGVEVHNAKTKPREEQYNSTYRVVSVLTVLHQDWLNGK

EYKCKVSNKALP<u>LP</u>E<u></u>EKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

The underlined and bolded amino acids represent amino acids that differ from the wild-type sequence.

iv. Humanized Heavy Chain

One embodiment provides an anti-B7-H4 monoclonal antibody or antigen binding fragment thereof that has a humanized heavy chain variable domain having at least 50%, 60%, 70%, 80%, 85%, 90%, 95%, 99%, or 100% sequence identity with one of the following amino acid sequences:

Humanized B1H1 VH1:
(SEQ ID NO: 34)
EVQLVQSGAEVKKPGASVKVSCKVSGYPFTSYWMHWVRQAPGQGLEWIGA

IYPGKSDTEYAPKFQGRVTLTADTSTSTAYMELSSLRSEDTAVYYCTSTW

THYFDYWGQGTTVTVSS

Humanized B1H1 VH2:
(SEQ ID NO: 35)
QVQLVQSGAEVKKPGASVKVSCKVSGYPFTSYWMEIWVRQAPGQGLEWMG

AIYPGKSDTEYAQKFQGRVTLTADTSTSTAYMELSSLRSEDTAVYYCTST

WTHYFDYWGQGTTVTVSS

Humanized B1H1 VH3:
(SEQ ID NO: 36)
QVQLVQSGAEVKKPGASVKVSCKVSGYPFTSYWMEIWVRQAPGQGLEWMG

AIYPGKSDTEYAQKFQGRVTLTADTSTSTAYMELSSLRSEDTATYYCTST

WTHYFDYWGQGTTVTVSS

Humanized B1H1 VH4:
(SEQ ID NO: 37)
QVQLVQSGAEVKKPGASVKVSCKVSGYPFTSYYMHWVRQAPGQGLEWMGA

IYPGKSDTEYAQKFQGRVTLTADTSTSTAYMELSSLRSEDTATYYCTSTW

THYFDYWGQGTTVTVSS

One embodiment provides an anti-B7-H4 monoclonal antibody or antigen binding fragment thereof that has a humanized heavy chain having at least 50%, 60%, 70%, 80%, 85%, 90%, 95%, 99%, or 100% sequence identity with one of the following amino acid sequences:

Heavy chain B1H1 Variant 1:
(SEQ ID NO: 38)
EVQLVQSGAEVKKPGASVKVSCKVSGYPFTSYWMHWVRQAPGQGLEWIGA

IYPGKSDTEYAPKFQGRVTLTADTSTSTAYMELSSLRSEDTAVYYCTSTW

THYFDYWGQGTTVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

Heavy chain B1H1 Variant 2:
(SEQ ID NO: 39)
QVQLVQSGAEVKKPGASVKVSCKVSGYPFTSYWMHWVRQAPGQGLEWMG

AIYPGKSDTEYAQKFQGRVTLTADTSTSTAYMELSSLRSEDTAVYYCTST

WTHYFDYWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK

Heavy Chain B1H1 Variant 3:
(SEQ ID NO: 40)
QVQLVQSGAEVKKPGASVKVSCKVSGYPFTSYWMHWVRQAPGQGLEWMG

AIYPGKSDTEYAQKFQGRVTLTADTSTSTAYMELSSLRSEDTATYYCTST

WTHYFDYWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK

Heavy chain B1H1 Variant 4:
(SEQ ID NO: 41)
QVQLVQSGAEVKKPGASVKVSCKVSGYPFTSYYMHWVRQAPGQGLEWMGA

IYPGKSDTEYAQKFQGRVTLTADTSTSTAYMELSSLRSEDTATYYCTSTW

THYFDYWGQGTTVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

In another embodiment, the monoclonal antibody or antigen binding fragment thereof has a humanized heavy chain having at least 50%, 60%, 70%, 80%, 85%, 90%, 95%, 99%, or 100% sequence identity with one of the following amino acid sequences:

Heavy chain B1H1 mutant variant 1:
(SEQ ID NO: 42)
EVQLVQSGAEVKKPGASVKVSCKVSGYPFTSYWMHWVRQAPGQGLEWIGA

IYPGKSDTEYAPKFQGRVTLTADTSTSTAYMELSSLRSEDTAVYYCTSTW

THYFDYWGQGTTVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTHTCPPCPAPELLGGPDVFLFPPKPKDT

LMISRTPEVTCVVVDVSHEDPEVKFNWYVDGVEVHNAKTKPREEQYNSTY

RVVSVLTVLHQDWLNGKEYKCKVSNKALPLPEEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK;

Heavy chain B1H1 mutant variant 2:
(SEQ ID NO: 43)
QVQLVQSGAEVKKPGASVKVSCKVSGYPFTSYWMHWVRQAPGQGLEWMGA

IYPGKSDTEYAQKFQGRVTLTADTSTSTAYMELSSLRSEDTAVYYCTSTW

THYFDYWGQGTTVTVSSASTKGPSVFPLAPSSKSTSGGTAALGCLVKDYF

PEPVTVSWNSGALTSGVHTFPAVLQSSGLYSLSSVVTVPSSSLGQTYICN

VNHKPSNTKVDKKVEPKSCDKTHTCPPCPAPELLGGPDVFLFPPKPKDTL

MISRTPEVTCVVVDVSHEDPEVKFNWYVDGVEVHNAKTKPREEQYNSTYR

VVSVLTVLHQDWLNGKEYKCKVSNKALPLPEEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK;

Heavy chain B1H1 mutant variant 3:
(SEQ ID NO: 44)
QVQLVQSGAEVKKPGASVKVSCKVSGYPFTSYWMHWVRQAPGQGLEWMGA

IYPGKSDTEYAQKFQGRVTLTADTSTSTAYMELSSLRSEDTATYYCTSTW

THYFDYWGQGTTVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTHTCPPCPAPELLGGPDVFLFPPKPKDT

LMISRTPEVTCVVVDVSHEDPEVKFNWYVDGVEVHNAKTKPREEQYNSTY

RVVSVLTVLHQDWLNGKEYKCKVSNKALPLPEEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK;
and

Heavy chain B1H1 mutant variant 4:
(SEQ ID NO: 45)
QVQLVQSGAEVKKPGASVKVSCKVSGYPFTSYYMHWVRQAPGQGLEWMGA

IYPGKSDTEYAQKFQGRVTLTADTSTSTAYMELSSLRSEDTATYYCTSTW

THYFDYWGQGTTVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTHTCPPCPAPELLGGPDVFLFPPKPKDT

LMISRTPEVTCVVVDVSHEDPEVKFNWYVDGVEVHNAKTKPREEQYNSTY

RVVSVLTVLHQDWLNGKEYKCKVSNKALPLPEEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK.

One embodiment provides an anti-B7H4 antibody, preferably a monoclonal antibody, or antigen binding fragment thereof that has a light chain having CDRs according to SEQ ID Nos: 14, 15, and 16.

One embodiment provides an anti-B7H4 antibody, preferably a monoclonal antibody, or an antigen binding fragment thereof having a heavy chain containing CDRs according to SEQ ID Nos: 9, 11, and 30.

One embodiment provides an anti-B7H4 antibody, preferably a monoclonal antibody, or antigen binding fragment thereof that has a light chain containing CDRs according to SEQ ID Nos: 14, 15, and 16 and a heavy chain containing CDRs according to SEQ ID Nos: 9, 11, and 30.

One embodiment provides an anti-B7H4 antibody, preferably a monoclonal antibody, or an antigen binding fragment thereof having a light chain at least 50%, 60%, 70%, 80%, 85%, 90%, 95%, 99%, or 100% sequence identity to SEQ ID NO:13 and a heavy chain having at least 50%, 60%, 70%, 80%, 85%, 90%, 95%, 99%, or 100% sequence identity to SEQ ID NO:29.

Another embodiment provides an anti-B7H4 antibody preferably a monoclonal antibody, or an antigen binding fragment thereof having a light chain variable domain having at least 50%, 60%, 70%, 80%, 85%, 90%, 95%, 99%, or 100% sequence identity to any one of SEQ ID NOs:19, 20, 21, 22, or 23, and a heavy chain variable domain having at least 50%, 60%, 70%, 80%, 85%, 90%, 95%, 99%, or 100% sequence identity to any one of SEQ ID NOs:34, 35, 36, or 37.

One embodiment provides an anti-B7H4 antibody or antigen binding fragment thereof having a light chain having an amino acid sequence according to any one of SEQ ID NOs: 24, 25, 26, 27, or 28, and a heavy chain having an amino acid sequence according to any one of SEQ ID NOs: 38, 39, 40, or 41.

Another embodiment provides an anti-B7H4 antibody or antigen binding fragment thereof having a light chain having an amino acid sequence according to any one of SEQ ID NOs: 24, 25, 26, 27, or 28, and a heavy chain having an amino acid sequence according to any one of SEQ ID NOs: 42, 43, 44, or 45.

One embodiment provides an anti-B7H4 antibody or antigen binding fragment thereof having two light chains and two heavy chains, wherein the two light chains include a polypeptide selected from the group consisting of SEQ ID NO: 24, 25, 26, 27, or 28, or a variant thereof having at least 50%, 60%, 70%, 80%, 85%, 90%, 95%, 99%, or more sequence identity to SEQ ID NO: 24, 25, 26, 27, or 28, and the two heavy chains include a polypeptide selected from the group consisting of SEQ ID NO: 38, 39, 40, or 41, or a variant thereof having at least 50%, 60%, 70%, 80%, 85%, 90%, 95%, 99%, or more sequence identity to SEQ ID NO: 38, 39, 40, or 41, and wherein the antibody or antigen binding fragment thereof binds to B7-H4.

Another embodiment provides an antibody or antigen binding fragment thereof having two light chains and two heavy chains, wherein the two light chains include a polypeptide selected from the group consisting of SEQ ID NO: 24, 25, 26, 27, or 28, or a variant thereof having at least 50%, 60%, 70%, 80%, 85%, 90%, 95%, 99%, or more sequence identity to SEQ ID NO: 24, 25, 26, 27, or 28, and the two heavy chains include a polypeptide selected from the group consisting of SEQ ID NO: 42, 43, 44, or 45, or a variant thereof having at least 50%, 60%, 70%, 80%, 85%, 90%, 95%, 99%, or more sequence identity to SEQ ID NO: 42, 43, 44, or 45, and wherein the antibody or antigen binding fragment thereof binds to B7-H4.

c. B1H3 Sequences

In one embodiment a murine monoclonal antibody is produced by hybridoma clone B1H3 and contains two light chains and two heavy chains and specifically binds B7-H4.

i. Light Chain

One embodiment provides an anti-B7-H4 murine monoclonal antibody or antigen binding fragment thereof that has a light chain having at least 50%, 60%, 70%, 80%, 85%, 90%, 95%, 99%, or 100% sequence identity with the following amino acid sequence:

(SEQ ID NO :46)
EIQMTQSPSSMSASLGDTITITCQATQDIVKSLNWYQQKPGKPPSFLIYY

TTQLAEGVPSRFSGSGSGSDYSLTISNLDSEDFADYYCLQFYEFPPTFGG

GTKLEIK

The CDRs are of SEQ ID NO:46 are bolded and underlined and are:

(SEQ ID NO: 14)
CDR1 QATQDIVKSLN;

(SEQ ID NO: 47)
CDR2 YYTTQLAE;
and (SEQ ID NO: 16)
CDR3 LQFYEFPPT.

Another embodiment provides a nucleic acid that encodes the light chain (SEQ ID NO:46).

An exemplary nucleic acid that encodes light chain (SEQ ID NO:46) is (SEQ ID NO: 48)
GAAATCCAGATGACCCAGTCTCCATCCTCTATGTCTGCATCTCTGGGAGAC

ACAATAACCATCACTTGCCAGGCAACTCAAGACATTGTTAAGAGTTTAAAC

TGGTATCAACAAAAACCAGGGAAACCCCCTTCATTCCTGATCTATTATACA

ACTCAACTGGCAGAAGGGGTCCCATCAAGGTTCAGTGGCAGTGGGTCTGGG

TCAGACTATTCTCTGACAATCAGCAACCTGGACTCTGAAGATTTTGCAGAC

TATTACTGTCTACAGTTTTATGAGTTTCCTCCGACGTTCGGTGGAGGCACC

AAGCTGGAAATCAAA.

ii. Heavy Chain

One embodiment provides an anti-B7-H4 murine monoclonal antibody or antigen binding fragment thereof that has a heavy chain having at least 50%, 60%, 70%, 80%, 85%, 90%, 95%, 99%, or 100% sequence identity with the following amino acid sequence:

(SEQ ID NO: 49)
EVQLQQSGTVLARPGASVKMSCKASGYTFSSYWMHWVKQRPGQGLEWIGAI

YPGKSDTSYNQKFQGKAKLTAVTSASTAFMELTSLTNEDSAVYYCTSTWTH

YFDYWGQGTTLTVSS.

The CDRs are of SEQ ID NO:49 are bolded and underlined and are:

(SEQ ID NO: 9)
CDR1 SYWMH;

(SEQ ID NO: 50)
CDR2 AIYPGKSDTEYNPNFKG;
and (SEQ ID NO: 11)
CDR3 TVRNVMDY.

Another embodiment provides a nucleic acid encoding heavy chain (SEQ ID NO:49).

An exemplary nucleic acid that encodes heavy chain (SEQ ID NO:49) is (SEQ ID NO: 51)
GAGGTTCAGCTCCAGCAGTCTGGGACTGTTCTGGCAAGGCCTGGGGCTTCA

GTGAAGATGTCCTGCAAGGCTTCTGGCTACACCTTTTCCAGCTACTGGATG

CACTGGGTAAAACAGAGGCCTGGACAGGGTCTGGAATGGATTGGCGCTATT

TATCCTGGAAAAAGTGATACTAGCTACAACCAGAAGTTCCAGGGCAAGGCC

AAACTGACTGCAGTCACATCTGCCAGCACTGCCTTCATGGAGCTCACCAGC

CTGACAAATGAGGACTCTGCGGTCTATTACTGTACAAGTACCTGGACCCAC

TACTTTGACTACTGGGGCCAAGGCACCACTCTCACAGTCTCCTCA.

One embodiment provides an anti-B7H4 antibody, preferably a monoclonal antibody, or antigen binding fragment thereof that has a light chain containing CDRs according to SEQ ID Nos: 14, 16, and 47.

One embodiment provides an anti-B7H4 antibody, preferably a monoclonal antibody, or an antigen binding fragment thereof having a heavy chain containing CDRs according to SEQ ID Nos: 9, 11, and 50.

One embodiment provides an anti-B7H4 antibody, preferably a monoclonal antibody, or antigen binding fragment thereof that has a light chain containing CDRs according to SEQ ID Nos: 14, 16, and 47, and a heavy chain containing CDRs according to SEQ ID Nos: 9, 11, and 50.

One embodiment provides an anti-B7H4 antibody, preferably a monoclonal antibody, or an antigen binding fragment thereof having a light chain at least 50%, 60%, 70%, 80%, 85%, 90%, 95%, 99%, or 100% sequence identity to SEQ ID NO:46 and a heavy chain having at least 50%, 60%, 70%, 80%, 85%, 90%, 95%, 99%, or 100% sequence identity to SEQ ID NO:49.

d. B1H10 Sequences

In one embodiment an anti-B7H4 murine monoclonal antibody is produced by hybridoma clone B1H10 and contains two light chains and two heavy chains.

i. Light Chain

One embodiment provides an anti-B7H4 murine monoclonal antibody or antigen binding fragment thereof that has a light chain having at least 50%, 60%, 70%, 80%, 85%, 90%, 95%, 99%, or 100% sequence identity with the following amino acid sequence:

(SEQ ID NO: 52)
DIQMTQTTSSLSASLGDRVTISCRASQDISNYLNWYQQKPDGTIKLLIYYT
SRLHSGVPSRFSGSGSGSDYSLTISNLEQEDIATYFCQQGNTLPWTFGGGT
KLEFK.

The CDRs are of SEQ ID NO:52 are bolded and underlined and are:

(SEQ ID NO: 53)
CDR1 RASQDISNYLN;

(SEQ ID NO: 54)
CDR2 YTSRLHS;
and (SEQ ID NO: 55)
CDR3 QQGNTLPWT.

Another embodiment provides a nucleic acid that encodes the light chain (SEQ ID NO:52).

An exemplary nucleic acid that encodes light chain (SEQ ID NO:52) is (SEQ ID NO: 56)
GATATCCAGATGACACAAACTACATCCTCCCTGTCTGCCTCTCTGGGAGAC

AGAGTCACCATCAGTTGCAGGGCAAGTCAGGACATTAGCAATTATTTAAAC

TGGTATCAGCAGAAACCAGATGGAACTATTAAACTCCTGATCTATTACACA

TCAAGATTACATTCAGGAGTCCCATCAAGGTTCAGTGGCAGTGGGTCTGGA

TCAGATTATTCTCTCACCATTAGCAACCTGGAGCAAGAAGATATTGCCACT

TACTTTTGCCAACAGGGTAATACGCTTCCGTGGACGTTCGGTGGAGGCACC

AAGCTGGAATTCAAA.

One embodiment provides an anti-B7H4 monoclonal antibody or antigen binding fragment thereof that has a light chain constant domain having at least 50%, 60%, 70%, 80%, 85%, 90%, 95%, 99%, or 100% sequence identity with the following amino acid sequence:

(SEQ ID NO: 57)
DIQMTQSPSSLSASVGDRVTITCRASQDISNYLNWYQQKPGKTIKLLIYY

TSRLHSGVPSRFSGSGSGTDYTLTISSLQPEDFATYFCQQGNTLPWTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC ii. Humanized B1H10 Light Chain

In another embodiment, the anti-B7H4 monoclonal antibody or antigen binding fragment thereof has a humanized light chain variable domain having at least 50%, 60%, 70%, 80%, 85%, 90%, 95%, 99%, or 100% sequence identity with one of the following amino acid sequences:

Humanized B1H10 VL1:
(SEQ ID NO: 58)
DIQMTQSPSSLSASVGDRVTITCRASQDISNYLNWYQQKPGKTIKLLIYY

TSRLHSGVPSRFSGSGSGTDYTLTISSLQPEDFATYFCQQGNTLPWTFGQ

GTKLEIK

Humanized B1H10 VL2:
(SEQ ID NO: 59)
DIQMTQSPSSLSASVGDRVTITCRASQDISNYLNWYQQKPGKAPKLLIYY

TSRLHSGVPSRFSGSGSGTDYTLTISSLQPEDFATYFCQQGNTLPWTFGQ

GTKLEIK

Humanized B1H10 VL3:
(SEQ ID NO: 60)
DIQMTQSPSSLSASVGDRVTITCRASQDISNYLNWYQQKPGKAPKLLIYY

TSRLHSGVPSRFSGSGSGTDYTLTISSLQPEDFATYFCQQGQTLPWTFGQ

GTKLEIK

Humanized B1H10 VL4:
(SEQ ID NO: 61)
DIQMTQSPSSLSASVGDRVTITCRASQDISNYLNWYQQKPGKAPKLLIYY

TSRLHSGVPSRFSGSGSGTDYTLTISSLQPEDFATYFCQQGSTLPWTFGQ

GTKLEIK

One embodiment provides an anti-B7H4 monoclonal antibody or antigen binding fragment thereof that has a humanized light chain having at least 50%, 60%, 70%, 80%, 85%, 90%, 95%, 99%, or 100% sequence identity with one of the following amino acid sequences:

Humanized B1H10 Light Chain Variant 1:
(SEQ ID NO: 62)
DIQMTQSPSSLSASVGDRVTITCRASQDISNYLNWYQQKPGKAPKLLIYY

TSRLHSGVPSRFSGSGSGTDYTLTISSLQPEDFATYFCQQGNTLPWTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Humanized B1H10 Light Chain Variant 2:
(SEQ ID NO : 63)
DIQMTQSPSSLSASVGDRVTITCRASQDISNYLNWYQQKPGKAPKLLIYY

TSRLHSGVPSRFSGSGSGTDYTLTISSLQPEDFATYFCQQGQTLPWTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Humanized B1H10 Light Chain Variant 3:
(SEQ ID NO: 64)
DIQMTQSPSSLSASVGDRVTITCRASQDISNYLNWYQQKPGKAPKLLIYY

TSRLHSGVPSRFSGSGSGTDYTLTISSLQPEDFATYFCQQGSTLPWTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC iii. Heavy Chain

One embodiment provides an anti-B7H4 murine monoclonal antibody or antigen binding fragment thereof that has a heavy chain having at least 50%, 60%, 70%, 80%, 85%, 90%, 95%, 99%, or 100% sequence identity with the following amino acid sequence:

```
                                                    (SEQ ID NO: 65)
EVQLQQSGPELVKPGASVKMSCKASGYTFTDYYMNWVRQSHGKSLEWIGR
VNPSNGGTNYNQKFKGKATLTVDKSLSTAYMQLSSLTSEDSAVYYCARRH
NYADFWGQGTTLTVSS.
```

The CDRs of SEQ ID NO:65 are bolded and underlined and are:

```
CDR1
                                                    (SEQ ID NO: 66)
DYYMN;

CDR2
                                                    (SEQ ID NO: 67)
RVNPSNGGTNYNQKFKG; and CDR3
                                                    (SEQ ID NO: 68)
RHNYADF.
```

Another embodiment provides a nucleic acid encoding heavy chain (SEQ ID NO:65).
An exemplary nucleic acid that encodes heavy chain (SEQ ID NO:65) is

```
                                                    (SEQ ID NO: 69)
GAGGTCCAGCTGCAACAGTCTGGACCTGAGCTGGTGAAGCCTGGGGCTTC

AGTGAAGATGTCCTGTAAGGCTTCTGGATACACATTCACTGACTACTACA

TGAACTGGGTGAGGCAGAGTCATGGAAAGAGCCTTGAGTGGATTGGACGT

GTTAATCCTAGCAATGGTGGTACTAACTACAACCAGAAATTCAAGGGCAA

GGCCACATTGACAGTAGACAAATCCCTCAGCACAGCCTACATGCAGCTCA

GCAGCCTGACATCTGAGGACTCTGCGGTCTATTACTGTGCAAGACGACAT

AACTACGCAGACTTCTGGGGCCAAGGCACCACTCTCACAGTCTCCTCA.
``` iv. Humanized B1H10 Heavy Chain

One embodiment provides an anti-B7H4 monoclonal antibody or antigen-binding fragment thereof that has a humanized heavy chain variable domain variant having at least 50%, 60%, 70%, 80%, 85%, 90%, 95%, 99%, or 100% sequence identity with one of the following amino acid sequences:

```
Humanized B1H10 VH1:
                                                    (SEQ ID NO: 70)
EVQLVQSGAEVKKPGASVKVSCKASGYTFTDYYMNWVRQAPGQGLEWIGR

VNPSNGGTNYAQKFQGRVTLTVDKSTSTAYMELSSLRSEDTAVYYCARRH

NYADFWGQGTTVTVSS

Humanized B1H10 VH2:
                                                    (SEQ ID NO: 71)
QVQLVQSGAEVKKPGASVKVSCKASGYTFTDYYMNWVRQAPGQGLEWMGR

VNPANGGTNYAQKFQGRVTLTVDTSTSTAYMELSSLRSEDTAVYYCARRH

NYADFWGQGTTVTVSS

Humanized B1H10 VH3:
                                                    (SEQ ID NO: 72)
QVQLVQSGAEVKKPGASVKVSCKASGYTFTDYYMNWVRQAPGQGLEWMGR

VNPSSGGTNYAQKFQGRVTLTVDTSTSTAYMELSSLRSEDTAVYYCARRH

NYADFWGQGTTVTVSS

Humanized B1H10 VH4:
                                                    (SEQ ID NO: 73)
QVQLVQSGAEVKKPGASVKVSCKASGYTFTDYYMNWVRQAPGQGLEWMGR

VNPSNGGTNYAQKFQGRVTLTVDTSKSTAYMELSSLRSEDTAVYYCARRH

NYADFWGQGTTVTVSS

Humanized B1H10 VH5:
                                                    (SEQ ID NO: 74)
QVQLVQSGAEVKKPGASVKVSCKASGYTFTDYYMNWVRQAPGQGLEWMGR

VNPSSGGTNYAQKFQGRVTLTVDTSKSTAYMELSSLRSEDTAVYYCARRH

NYADFWGQGTTVTVSS
```

One embodiment provides an anti-B7H4 monoclonal antibody or antigen binding fragment thereof that has a humanized heavy chain variant having at least 50%, 60%, 70%, 80%, 85%, 90%, 95%, 99%, or 100% sequence identity with the one of the following amino acid sequences:

```
Humanized B1H10 Heavy Chain Variant 1:
                                                    (SEQ ID NO: 75)
EVQLVQSGAEVKKPGASVKVSCKASGYTFTDYYMNWVRQAPGQGLEWIGRV

NPSNGGTNYAQKFQGRVTLTVDKSTSTAYMELSSLRSEDTAVYYCARRHNY

ADFWGQGTTVTVSSASTKGPSVFPLAPSSKSTSGGTAALGCLVKDYFPEPV

TVSWNSGALTSGVHTFPAVLQSSGLYSLSSVVTVPSSSLGTQTYICNVNHK

PSNTKVDKKVEPKSCDKTHTCPPCPAPELLGGPSVFLFPPKPKDTLMISRT

PEVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFLYSK

LTVDKSRWQQGNVFSCSVMHEALHNHYTQKSLSLSPGK

Humanized B1H10 Heavy Chain Variant 2:
                                                    (SEQ ID NO: 76)
QVQLVQSGAEVKKPGASVKVSCKASGYTFTDYYMNWVRQAPGQGLEWMGRV

NPANGGTNYAQKFQGRVTLTVDTSTSTAYMELSSLRSEDTAVYYCARRHNY

ADFWGQGTTVTVSSASTKGPSVFPLAPSSKSTSGGTAALGCLVKDYFPEPV

TVSWNSGALTSGVHTFPAVLQSSGLYSLSSVVTVPSSSLGTQTYICNVNHK

PSNTKVDKKVEPKSCDKTHTCPPCPAPELLGGPSVFLFPPKPKDTLMISRT

PEVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFLYSK

LTVDKSRWQQGNVFSCSVMHEALHNHYTQKSLSLSPGK

Humanized B1H10 Heavy Chain Variant 3:
                                                    (SEQ ID NO: 77)
QVQLVQSGAEVKKPGASVKVSCKASGYTFTDYYMNWVRQAPGQGLEWMGRV

NPSSGGTNYAQKFQGRVTLTVDTSTSTAYMELSSLRSEDTAVYYCARRHNY

ADFWGQGTTVTVSSASTKGPSVFPLAPSSKSTSGGTAALGCLVKDYFPEPV

TVSWNSGALTSGVHTFPAVLQSSGLYSLSSVVTVPSSSLGTQTYICNVNHK

PSNTKVDKKVEPKSCDKTHTCPPCPAPELLGGPSVFLFPPKPKDTLMISRT

PEVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRDEL
```

TKNQVSLTCLVKGFYPSDIAVEWESNGQPENNYKTTPPVLDSDGSFFLYSK

LTVDKSRWQQGNVFSCSVMHEALHNHYTQKSLSLSPGK

Humanized B1H10 Heavy Chain Variant 4:
(SEQ ID NO: 78)
QVQLVQSGAEVKKPGASVKVSCKASGYTFTDYYMNWVRQAPGQGLEWMGRV

NPSNGGTNYAQKFQGRVTLTVDTSKSTAYMELSSLRSEDTAVYYCARRHNY

ADFWGQGTTVTVSSASTKGPSVFPLAPSSKSTSGGTAALGCLVKDYFPEPV

TVSWNSGALTSGVHTFPAVLQSSGLYSLSSVVTVPSSSLGTQTYICNVNHK

PSNTKVDKKVEPKSCDKTHTCPPCPAPELLGGPSVFLFPPKPKDTLMISRT

PEVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFLYSK

LTVDKSRWQQGNVFSCSVMHEALHNHYTQKSLSLSPGK

Humanized B1H10 Heavy Chain Variant 5:
(SEQ ID NO: 79)
QVQLVQSGAEVKKPGASVKVSCKASGYTFTDYYMNWVRQAPGQGLEWMGRV

NPSSGGTNYAQKFQGRVTLTVDTSKSTAYMELSSLRSEDTAVYYCARRHNY

ADFWGQGTTVTVSSASTKGPSVFPLAPSSKSTSGGTAALGCLVKDYFPEPV

TVSWNSGALTSGVHTFPAVLQSSGLYSLSSVVTVPSSSLGTQTYICNVNHK

PSNTKVDKKVEPKSCDKTHTCPPCPAPELLGGPSVFLFPPKPKDTLMISRT

PEVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRDEL

TKNQVSLTCLVKGFYPSDIAVEWESNGQPENNYKTTPPVLDSDGSFFLYSK

LTVDKSRWQQGNVFSCSVMHEALHNHYTQKSLSLSPGK

One embodiment provides an anti-B7H4 monoclonal antibody or antigen binding fragment thereof that has a humanized mutant heavy chain variant having at least 50%, 60%, 70%, 80%, 85%, 90%, 95%, 99%, or 100% sequence identity with one of the following amino acid sequences:

Humanized Mutant B1H10 Heavy Chain Variant 1:
(SEQ ID NO: 80)
EVQLVQSGAEVKKPGASVKVSCKASGYTFTDYYMNWVRQAPGQGLEWIGR

VNPSNGGTNYAQKFQGRVTLTVDKSTSTAYMELSSLRSEDTAVYYCARRH

NYADFWGQGTTVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPDVFLFPPKPKDTL

MISRTPEVTCVVVDVSHEDPEVKFNWYVDGVEVHNAKTKPREEQYNSTYR

VVSVLTVLHQDWLNGKEYKCKVSNKALPLPEEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK

Humanized Mutant B1H10 Heavy Chain Variant 2:
(SEQ ID NO: 81)
QVQLVQSGAEVKKPGASVKVSCKASGYTFTDYYMNWVRQAPGQGLEWMGR

VNPANGGTNYAQKFQGRVTLTVDTSTSTAYMELSSLRSEDTAVYYCARRH

NYADFWGQGTTVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPDVFLFPPKPKDTL

MISRTPEVTCVVVDVSHEDPEVKFNWYVDGVEVHNAKTKPREEQYNSTYR

VVSVLTVLHQDWLNGKEYKCKVSNKALPLPEEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK

Humanized Mutant B1H10 Heavy Chain Variant 3:
(SEQ ID NO: 82)
QVQLVQSGAEVKKPGASVKVSCKASGYTFTDYYMNWVRQAPGQGLEWMGR

VNPSSGGTNYAQKFQGRVTLTVDTSTSTAYMELSSLRSEDTAVYYCARRH

NYADFWGQGTTVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPDVFLFPPKPKDTL

MISRTPEVTCVVVDVSHEDPEVKFNWYVDGVEVHNAKTKPREEQYNSTYR

VVSVLTVLHQDWLNGKEYKCKVSNKALPLPEEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK

Humanized Mutant B1H10 Heavy Chain Variant 4:
(SEQ ID NO: 83)
QVQLVQSGAEVKKPGASVKVSCKASGYTFTDYYMNWVRQAPGQGLEWMGR

VNPSNGGTNYAQKFQGRVTLTVDTSKSTAYMELSSLRSEDTAVYYCARRH

NYADFWGQGTTVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPDVFLFPPKPKDTL

MISRTPEVTCVVVDVSHEDPEVKFNWYVDGVEVHNAKTKPREEQYNSTYR

VVSVLTVLHQDWLNGKEYKCKVSNKALPLPEEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK

Humanized Mutant B1H10 Heavy Chain Variant 5:
(SEQ ID NO: 84)
QVQLVQSGAEVKKPGASVKVSCKASGYTFTDYYMNWVRQAPGQGLEWMGR

VNPSSGGTNYAQKFQGRVTLTVDTSKSTAYMELSSLRSEDTAVYYCARRH

NYADFWGQGTTVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPDVFLFPPKPKDTL

MISRTPEVTCVVVDVSHEDPEVKFNWYVDGVEVHNAKTKPREEQYNSTYR

VVSVLTVLHQDWLNGKEYKCKVSNKALPLPEEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK

One embodiment provides an anti-B7H4 antibody, preferably a monoclonal antibody, or antigen binding fragment thereof that has a light chain containing CDRs according to SEQ ID Nos: 53, 54, or 55.

One embodiment provides an anti-B7H4 antibody, preferably a monoclonal antibody, or an antigen binding fragment thereof having a heavy chain containing CDRs according to SEQ ID Nos: 66, 67, or 68.

One embodiment provides an anti-B7H4 antibody, preferably a monoclonal antibody, or antigen binding fragment thereof that has a light chain containing CDRs according to SEQ ID Nos: 53, 54, or 55, and a heavy chain containing CDRs according to SEQ ID Nos: 66, 67, or 68.

One embodiment provides an anti-B7H4 antibody, preferably a monoclonal antibody, or an antigen binding fragment thereof having a light chain at least 50%, 60%, 70%, 80%, 85%, 90%, 95%, 99%, or 100% sequence identity to SEQ ID NO:52 and a heavy chain having at least 50%, 60%, 70%, 80%, 85%, 90%, 95%, 99%, or 100% sequence identity to SEQ ID NO:65.

Another embodiment provides an anti-B7H4 antibody preferably a monoclonal, or an antigen binding fragment thereof having a light chain variable domain having at least 50%, 60%, 70%, 80%, 85%, 90%, 95%, 99%, or 100% sequence identity to any one of SEQ ID NOs:58, 59, 60, or 61, and a heavy chain variable domain having at least 50%, 60%, 70%, 80%, 85%, 90%, 95%, 99%, or 100% sequence identity to any one of SEQ ID NOs:70, 71, 72, 73, or 74.

One embodiment provides an anti-B7H4 antibody or antigen binding fragment thereof having a light chain having an amino acid sequence according to any one of SEQ ID NOs: 62, 63, or 64, and a heavy chain having an amino acid sequence according to any one of SEQ ID NOs: 75, 76, 77, 78, or 79.

Another embodiment provides an anti-B7H4 antibody or antigen binding fragment thereof having a light chain having an amino acid sequence according to any one of SEQ ID NOs: 62, 63, or 64, and a heavy chain having an amino acid sequence according to any one of SEQ ID NOs: 80, 81, 82, 83, or 84.

One embodiment provides an anti-B7H4 antibody or antigen binding fragment thereof having two light chains and two heavy chains, wherein the two light chains include a polypeptide selected from the group consisting of SEQ ID NO: 62, 63, or 64, or a variant thereof comprising at least 50%, 60%, 70%, 80%, 85%, 90%, 95%, 99%, or more sequence identity to SEQ ID NO: 62, 63, or 64, and the two heavy chains include a polypeptide selected from the group consisting of SEQ ID NO: 75, 76, 77, 78, or 79, or a variant thereof having at least 50%, 60%, 70%, 80%, 85%, 90%, 95%, 99%, or more sequence identity to SEQ ID NO: 75, 76, 77, 78, or 79.

Another embodiment provides an anti-B7H4 antibody or antigen binding fragment thereof having two light chains and two heavy chains, wherein the two light chains include a polypeptide selected from the group consisting of SEQ ID NO: 62, 63, or 64, or a variant thereof having at least 50%, 60%, 70%, 80%, 85%, 90%, 95%, 99%, or more sequence identity to SEQ ID NO: 62, 63, or 64, and the two heavy chains include a polypeptide selected from the group consisting of SEQ ID NO: 80, 81, 82, 83, or 84, or a variant thereof having at least 50%, 60%, 70%, 80%, 85%, 90%, 95%, 99%, or more sequence identity to SEQ ID NO: 80, 81, 82, 83, or 84.

e. B2E6 Sequences

In one embodiment an anti-B7H4 murine monoclonal antibody is produced by hybridoma clone B2E6 and contains two light chains and two heavy chains.

i. Light Chain

One embodiment provides an anti-B7H4 murine monoclonal antibody or antigen binding fragment thereof that has a light chain having at least 50%, 60%, 70%, 80%, 85%, 90%, 95%, 99%, or 100% sequence identity with the following amino acid sequence:

```
                                         (SEQ ID NO: 85)
ETVMTQSHKIMSTSVGDRVTITCKASQDVRTAVAWYQQKPGQSPKLLISS

ASYQYTGVPDRFTGSGSGTDFTFTISSLQAEDLAVYYCHQYYNTPLTFGA

GTKLELR.
```

The CDRs are of SEQ ID NO:85 are bolded and underlined and are:

```
CDR1
                                         (SEQ ID NO: 4)
    KASQDVRTAVA;

CDR2
                                         (SEQ ID NO: 86)
    SASYQYT; and

CDR3
                                         (SEQ ID NO: 87)
    HQYYNTPLT.
```

Another embodiment provides a nucleic acid that encodes the light chain (SEQ ID NO:85).

An exemplary nucleic acid that encodes light chain (SEQ ID NO:85) is

```
                                         (SEQ ID NO: 88)
GAAACTGTGATGACCCAGTCTCACAAAATCATGTCCACTTCAGTAGGAG

ACAGGGTCACCATCACCTGCAAGGCCAGTCAGGATGTGAGAACTGCTGT

GGCCTGGTATCAACAGAAACCAGGACAATCTCCTAAATTACTAATTTCC

TCGGCATCCTACCAATACACTGGAGTCCCTGATCGCTTCACTGGCAGTG

GATCTGGGACGGATTTCACTTTCACCATCAGCAGTTTGCAGGCTGAAGA

CCTGGCAGTTTATTACTGTCATCAGTATTATAATACTCCGCTCACGTTC

GGTGCTGGGACCAAGCTGGAGCTGAGA.
``` ii. Heavy Chain

One embodiment provides an anti-B7H4 murine monoclonal antibody or antigen binding fragment thereof that has a heavy chain having at least 50%, 60%, 70%, 80%, 85%, 90%, 95%, 99%, or 100% sequence identity with the following amino acid sequence:

```
                                         (SEQ ID NO: 89)
EVQLQQSGTVLARPGASVKMSCKASGYTFTSYWMHWVKQRPGQGLEWI

GAIYPGKSDTTYNQKFEGKAKLTAVTSDSTAYMDLSSLTNEDSAVYYC

TSSVRNAMDYWGQGTSVTVSS.
```

The CDRs are of SEQ ID NO:89 are bolded and underlined and are:

```
CDR1
                                         (SEQ ID NO: 9)
    SYWMH;

CDR2
                                         (SEQ ID NO: 90)
    AIYPGKSDTTYNQKFEG; and

CDR3
                                         (SEQ ID NO: 91)
    SVRNAMDY.
```

Another embodiment provides a nucleic acid encoding heavy chain (SEQ ID NO:89). An exemplary nucleic acid that encodes heavy chain (SEQ ID NO:89) is (SEQ ID NO: 92)
GAGGTTCAGCTCCAGCAGTCTGGGACTGTGCTGGCAAGGCCTGGGCTT

CAGTGAAGATGTCCTGCAAGGCTTCTGGCTACACCTTCACCAGCTACTG

GATGCACTGGGTAAAACAGAGGCCTGGACAGGGTCTGGAATGGATTGGC

GCTATTTATCCTGGAAAAAGTGATACTACCTACAACCAGAAGTTCGAGG

GCAAGGCCAAACTGACTGCAGTCACATCTGACAGCACAGCCTACATGGA

TCTCAGTAGCCTGACAAATGAGGACTCTGCGGTCTATTACTGTACATCT

TCGGTTCGGAATGCTATGGACTACTGGGGTCAAGGAACCTCAGTCACCG

TCTCCTCA.

One embodiment provides an anti-B7H4 antibody, preferably a monoclonal antibody, or antigen binding fragment thereof that has a light chain having CDRs according to SEQ ID Nos: 4, 86, and 87

One embodiment provides an anti-B7H4 antibody, preferably a monoclonal antibody, or an antigen binding fragment thereof having a heavy chain having CDRs according to SEQ ID Nos: 9, 90, and 91.

One embodiment provides an anti-B7H4 antibody, preferably a monoclonal antibody, or antigen binding fragment thereof that has a light chain containing CDRs according to SEQ ID Nos: 4, 86, and 87, and a heavy chain containing CDRs according to SEQ ID Nos: 9, 90, and 91.

One embodiment provides an anti-B7H4 antibody, preferably a monoclonal antibody, or an antigen binding fragment thereof having a light chain at least 50%, 60%, 70%, 80%, 85%, 90%, 95%, 99%, or 100% sequence identity to SEQ ID NO:85 and a heavy chain having at least 50%, 60%, 70%, 80%, 85%, 90%, 95%, 99%, or 100% sequence identity to SEQ ID NO:89.

f. B4B3 Sequences

In one embodiment an anti-B7H4 murine monoclonal antibody is produced by hybridoma clone B4B3 and contains two light chains and two heavy chains.

i. Light Chain

One embodiment provides an anti-B7H4 murine monoclonal antibody or antigen binding fragment thereof that has a light chain having at least 50%, 60%, 70%, 80%, 85%, 90%, 95%, 99%, or 100% sequence identity with the following amino acid sequence:

(SEQ ID NO: 93)
DVLMTQTPLSLPVSLGGQASISCRSSQIIVHSNGNTYLEWYLQKPGQSPK

LLIYKVSNRFSGVPDRFSGSGSGTDFTLKISRVEAEDLGVYYCFQGSHVP

WTFGGGTKLEIK

The CDRs of SEQ ID NO:93 are bolded and underlined and are:

CDR1
(SEQ ID NO: 94)
RSSQIIVHSNGNTYLE;

CDR2
(SEQ ID NO: 95)
KVSNRFS; and

CDR3
(SEQ ID NO: 96)
FQGSHVPWT.

Another embodiment provides a nucleic acid that encodes the light chain (SEQ ID NO:93).

An exemplary nucleic acid that encodes light chain (SEQ ID NO:93) is (SEQ ID NO: 97)
GATGTTTTGATGACCCAAACTCCACTCTCCCTGCCTGTCAGTCTTGGAGG

TCAAGCCTCCATCTCTTGCAGATCTAGTCAGATCATTGTACATAGTAATG

GAAACACCTATTTAGAATGGTACCTGCAGAAACCAGGCCAGTCTCCAAAG

CTCCTGATCTACAAAGTTTCCAACCGATTTTCTGGGGTCCCAGACAGGTT

CAGTGGCAGTGGATCAGGGACAGATTTCACACTCAAGATCAGCAGAGTGG

AGGCTGAGGATCTGGGAGTTTATTACTGCTTTCAAGGTTCACATGTTCCG

TGGACGTTCGGTGGAGGCACCAAGCTGGAAATCAAA.

ii. Heavy Chain

One embodiment provides an anti-B7H4 murine monoclonal antibody or antigen binding fragment thereof that has a heavy chain having at least 50%, 60%, 70%, 80%, 85%, 90%, 95%, 99%, or 100% sequence identity with the following amino acid sequence:

(SEQ ID NO: 98)
QVQLQQPGAELVKPGASVKLSCKASGYTFISYWMHWVKQRPGQGLEWIGE

IDPSDSYTYYNOKFKGKATLTVDKSSSTAYMQLSSLTSEDSAVYYCARRK

TWDWYFDVWGAGTTVTVSS.

The CDRs are of SEQ ID NO:98 are bolded and underlined and are:

CDR1
(SEQ ID NO: 9)
SYWMH;

CDR2
(SEQ ID NO: 99)
EIDPSDSYTYYNQKFKG; and

CDR3
(SEQ ID NO: 100)
RKTWDWYFDV.

Another embodiment provides a nucleic acid encoding heavy chain (SEQ ID NO:98). An exemplary nucleic acid that encodes heavy chain (SEQ ID NO:98) is (SEQ ID NO: 101)
CAGGTCCAGCTGCAGCAGCCTGGGGCTGAACTGGTGAAGCCTGGGGCTTC

AGTGAAGCTGTCCTGCAAGGCTTCTGGATACACCTTCATTAGCTACTGGA

TGCACTGGGTGAAGCAGAGGCCTGGACAAGGCCTTGAGTGGATCGGAGAG

ATTGATCCTTCTGATAGTTATACTTACTACAATCAAAAGTTCAAGGGCAA

GGCCACATTGACTGTAGACAAATCCTCCAGCACAGCCTACATGCAACTCA

GCAGCCTGACATCTGAGGACTCTGCGGTCTATTACTGTGCAAGAAGGAAA

ACCTGGGACTGGTACTTCGATGTCTGGGGCGCAGGGACCACGGTCACCGT

CTCCTCA.

One embodiment provides an anti-B7H4 antibody, preferably a monoclonal antibody, or antigen binding fragment thereof that has a light chain containing CDRs according to SEQ ID Nos: 94, 95, and 96.

One embodiment provides an anti-B7H4 antibody, preferably a monoclonal antibody, or an antigen binding fragment thereof having a heavy chain containing CDRs according to SEQ ID Nos: 9, 99, and 100.

One embodiment provides an anti-B7H4 antibody, preferably a monoclonal antibody, or antigen binding fragment thereof that has a light chain containing CDRs according to SEQ ID Nos: 94, 95, and 96, and a heavy chain containing CDRs according to SEQ ID Nos: 9, 99, and 100.

One embodiment provides an anti-B7H4 antibody, preferably a monoclonal antibody, or an antigen binding fragment thereof having a light chain at least 50%, 60%, 70%, 80%, 85%, 90%, 95%, 99%, or 100% sequence identity to SEQ ID NO:93 and a heavy chain having at least 50%, 60%, 70%, 80%, 85%, 90%, 95%, 99%, or 100% sequence identity to SEQ ID NO:98.

g. B4E11 Sequences

In one embodiment an anti-B7H4 murine monoclonal antibody is produced by hybridoma clone B4E11 and contains two light chains and two heavy chains.

i. Light Chain

One embodiment provides an anti-B7H4 murine monoclonal antibody or antigen binding fragment thereof that has a light chain having at least 50%, 60%, 70%, 80%, 85%, 90%, 95%, 99%, or 100% sequence identity with the following amino acid sequence:

(SEQ ID NO: 102)
DIVNITQSHKFMSTSVGDRVTITCKASQDVSTAVAWYQQKPGQSPKLLIS

SASYRYTGVPDRFTGSGSGTDFTFTISSVQAEDLAVYYCQQHYSTPTFGG

GTKLEIR.

The CDRs of SEQ ID NO:102 are bolded and underlined and are:

CDR1
(SEQ ID NO: 103)
KASQDVSTAVA;

CDR2
(SEQ ID NO: 104)
SASYRYT; and

CDR3
(SEQ ID NO: 105)
QQHYSTPT.

Another embodiment provides a nucleic acid that encodes the light chain (SEQ ID NO:102).

An exemplary nucleic acid that encodes light chain (SEQ ID NO:102) is (SEQ ID NO: 106)
GACATTGTGATGACCCAGTCTCACAAATTCATGTCCACATCAGTAGGAGA

CAGGGTCACTATCACCTGCAAGGCCAGTCAGGATGTGAGTACTGCTGTAG

CCTGGTATCAACAGAAACCAGGACAGTCTCCTAAACTACTGATTTCCTCG

GCATCCTACCGGTACACTGGAGTCCCTGATCGCTTCACTGGCAGTGGATC

TGGGACGGATTTCACTTTCACCATCAGCAGTGTGCAGGCTGAAGACCTGG

CAGTTTATTACTGTCAGCAACATTATAGTACTCCGACGTTCGGTGGAGGC

ACCAAGCTGGAAATCAGA.

ii. Heavy Chain

One embodiment provides an anti-B7H4 murine monoclonal antibody or antigen binding fragment thereof that has a heavy chain having at least 50%, 60%, 70%, 80%, 85%, 90%, 95%, 99%, or 100% sequence identity with the following amino acid sequence:

(SEQ ID NO: 107)
EVQLQQSGTVLARPGASVKMSCKASGYTFTSYWMHWVKERPGQGLEWIGA

IYPGDSDTRYNQKFKGRAKLTAVTSANTAYMELSSLTNDDSAVFYCTCTT

AGVLDYWGQGTSVTVSS.

The CDRs are of SEQ ID NO:107 are bolded and underlined and are:

CDR1
(SEQ ID NO: 9)
SYWMH;

CDR2
(SEQ ID NO: 108)
AIYPGDSDTRYNQKFKG; and

CDR3
(SEQ ID NO: 109)
TTAGVLDY.

Another embodiment provides a nucleic acid encoding heavy chain (SEQ ID NO:107). An exemplary nucleic acid that encodes heavy chain (SEQ ID NO:107) is (SEQ ID NO: 110)
GAGGTTCAGCTCCAGCAGTCTGGGACTGTGCTGGCAAGGCCTGGGGCTTCA

GTGAAGATGTCCTGCAAGGCTTCTGGCTACACCTTTACCAGCTACTGGATG

CACTGGGTAAAAGAGAGGCCTGGACAGGGTCTGGAATGGATTGGCGCTATT

TATCCTGGAGATAGTGATACTAGGTATAATCAGAAGTTCAAGGGCAGGGCC

AAACTGACTGCAGTCACATCTGCCAACACTGCCTACATGGAGCTCAGCAGC

CTGACAAATGATGACTCTGCGGTCTTCTACTGTACATGTACTACGGCTGGT

GTTTTGGACTACTGGGGTCAAGGAACCTCAGTCACCGTCTCCTCA.

One embodiment provides an anti-B7H4 antibody, preferably a monoclonal antibody, or antigen binding fragment thereof that has a light chain containing CDRs according to SEQ ID Nos: 103, 104, and 105.

One embodiment provides an anti-B7H4 antibody, preferably a monoclonal antibody, or an antigen binding fragment thereof having a heavy chain containing CDRs according to SEQ ID Nos: 9, 108, and 109.

One embodiment provides an anti-B7H4 antibody, preferably a monoclonal antibody, or antigen binding fragment thereof that has a light chain containing CDRs according to SEQ ID Nos: 103, 104, and 105, and a heavy chain containing CDRs according to SEQ ID Nos: 9, 108, and 109.

One embodiment provides an anti-B7H4 antibody, preferably a monoclonal antibody, or an antigen binding fragment thereof having a light chain at least 50%, 60%, 70%, 80%, 85%, 90%, 95%, 99%, or 100% sequence identity to SEQ ID NO:102 and a heavy chain having at least 50%, 60%, 70%, 80%, 85%, 90%, 95%, 99%, or 100% sequence identity to SEQ ID NO:107.

h. B6C8 Sequences

In one embodiment an anti-B7H4 murine monoclonal antibody is produced by hybridoma clone B6C8 and contains two light chains and two heavy chains.

i. Light Chain

One embodiment provides an anti-B7H4 murine monoclonal antibody or antigen binding fragment thereof that has a light chain having at least 50%, 60%, 70%, 80%, 85%, 90%, 95%, 99%, or 100% sequence identity with the following amino acid sequence:

(SEQ ID NO: 111)
DVVMTQTPLSLPVSLGDQASISCTSSQSIVHGNGNTYLEWYLQKPGQSPKWYKVSNRFSGVPDRFSGSGSGTDFTLKISRVEAEDLGVYYCFQGSHVPYTFGGGTKLEIK.

The CDRs of SEQ ID NO:111 are bolded and underlined and are:

CDR1
(SEQ ID NO: 112)
TSSQSIVHGNGNTYLE;

CDR2
(SEQ ID NO: 95)
KVSNRFS; and

CDR3
(SEQ ID NO: 113)
FQGSHVPYT.

Another embodiment provides a nucleic acid that encodes the light chain (SEQ ID NO:111).

An exemplary nucleic acid that encodes light chain (SEQ ID NO:111) is (SEQ ID NO: 114)
GATGTTGTGATGACCCAAACTCCACTCTCCCTGCCTGTCAGTCTTGGAGATCAGGCCTCCATCTCTTGCACATCTAGTCAGAGCATTGTACATGGTAATGGAAACACCTATTTAGAATGGTACCTGCAGAAGCCAGGCCAGTCTCCAAAGCTCCTGATCTACAAAGTTTCCAACCGATTTTCTGGGGTCCCAGACAGGTTCAGTGGCAGTGGATCAGGGACAGATTTCACACTCAAGATCAGCAGAGTGGAGGCTGAGGATCTGGGAGTTTATTACTGCTTTCAAGGTTCACATGTTCCGTACACGTTCGGAGGGGGGACCAAGCTGGAAATAAAA.

ii. Heavy Chain

One embodiment provides an anti-B7H4 murine monoclonal antibody or antigen binding fragment thereof that has a heavy chain having at least 50%, 60%, 70%, 80%, 85%, 90%, 95%, 99%, or 100% sequence identity with the following amino acid sequence:

(SEQ ID NO: 115)
QVQLQQPGAELVKPGASVKLSCKASGYSFTSYWMNWVKQRPGRGLEWIGRIHPSDSETHYNQKFKSKATLTVDKSSSTAYIQLSSLTSEDSAVYFCARYGLFYGNDGYAMDHWGQGTSVTVSS.

The CDRs of SEQ ID NO:115 are bolded and underlined and are:

CDR1
(SEQ ID NO: 116)
SYWMN;

CDR2
(SEQ ID NO: 117)
RIHPSDSETHYNQKFKS; and

CDR3
(SEQ ID NO: 118)
YGLFYGNDGYAMDH.

Another embodiment provides a nucleic acid encoding heavy chain (SEQ ID NO:115). An exemplary nucleic acid that encodes heavy chain (SEQ ID NO:115) is (SEQ ID NO: 119)
CAGGTCCAACTGCAGCAGCCTGGGGCTGAACTGGTGAAGCCTGGGGCTTCAGTGAAGCTGTCCTGCAAGGCTTCTGGCTACTCTTTCACCAGCTACTGGATGAACTGGGTGAAGCAGAGGCCTGGACGAGGCCTCGAGTGGATTGGAAGGATTCATCCTTCTGATAGTGAAACTCACTACAATCAAAAGTTCAAGAGCAAGGCCACACTGACTGTAGACAAATCCTCCAGCACAGCCTACATCCAACTCAGCAGCCTGACATCTGAGGACTCTGCGGTCTATTTTTGTGCAAGATACGGGCTCTTCTATGGTAACGACGGATATGCTATGGACCACTGGGGTCAAGGAACCTCAG.

One embodiment provides an anti-B7H4 antibody, preferably a monoclonal antibody, or antigen binding fragment thereof that has a light chain containing CDRs according to SEQ ID Nos: 97, 116 and 117.

One embodiment provides an anti-B7H4 antibody, preferably a monoclonal antibody, or an antigen binding fragment thereof having a heavy chain containing CDRs according to SEQ ID Nos: 118, 119, and 120.

One embodiment provides an anti-B7H4 antibody, preferably a monoclonal antibody, or antigen binding fragment thereof that has a light chain containing CDRs according to SEQ ID Nos 97, 114, and 115, and a heavy chain containing CDRs according to SEQ ID Nos: 118, 119, and 120.

One embodiment provides an antibody, preferably a monoclonal antibody, or an antigen binding fragment thereof having a light chain at least 50%, 60%, 70%, 80%, 85%, 90%, 95%, 99%, or 100% sequence identity to SEQ ID NO:113 and a heavy chain having at least 50%, 60%, 70%, 80%, 85%, 90%, 95%, 99%, or 100% sequence identity to SEQ ID NO:117.

i. B9H1 Sequences

In one embodiment an anti-B7H4 murine monoclonal antibody is produced by hybridoma clone B9H1 and contains two light chains and two heavy chains.

i. Light Chain

One embodiment provides an anti-B7H4 murine monoclonal antibody or antigen binding fragment thereof that has a light chain having at least 50%, 60%, 70%, 80%, 85%, 90%, 95%, 99%, or 100% sequence identity with the following amino acid sequence:

(SEQ ID NO: 120)
DIQMTQTTSSLSASLGDRVTISCRASQDISFYLNWYQQKPDGTVKLLIYYTSRLHSGVPSRFSGSGSGTDYSLTISNLEQEDIATYFCQQGNTLPWTFGGGTKLEIK.

The CDRs of SEQ ID NO:120 are bolded and underlined and are:

CDR1
(SEQ ID NO: 121)
RASQDISFYLN;

CDR2
(SEQ ID NO: 54)
YTSRLHS;
and

CDR3
(SEQ ID NO: 55)
QQGNTLPWT.

Another embodiment provides a nucleic acid that encodes the light chain (SEQ ID NO:120).

An exemplary nucleic acid that encodes light chain (SEQ ID NO:120) is (SEQ ID NO: 122)
GATATCCAGATGACACAGACTACATCCTCCCTGTCTGCCTCTCTGGGAGA

CAGAGTCACCATCAGTTGCAGGGCAAGTCAGGACATTAGCTTTTATTTAA

ACTGGTATCAGCAGAAACCAGATGGAACTGTTAAACTCCTGATCTACTAC

ACATCAAGATTACACTCAGGAGTCCCATCAAGGTTCAGTGGCAGTGGGTC

TGGAACAGATTATTCTCTCACCATTAGCAACCTGGAGCAAGAAGATATTG

CCACTTACTTTTGCCAACAGGGTAATACACTTCCGTGGACGTTCGGTGGA

GGCACCAAGCTGGAAATCAAA.

ii. Heavy Chain

One embodiment provides an anti-B7H4 murine monoclonal antibody or antigen binding fragment thereof that has a heavy chain having at least 50%, 60%, 70%, 80%, 85%, 90%, 95%, 99%, or 100% sequence identity with the following amino acid sequence:

(SEQ ID NO: 123)
EVQLQQSGPELVKPGASVKMSCKASGYTFTDYYMNWVKQSHGKSLEWIGRV

NPSNGGTSYNQKFKGKATLTVDKSLSAAYMQLNSLTSEDSAVYYCARRHNY

PDYWGQGTTLTVSS.

The CDRs of SEQ ID NO:123 are bolded and underlined and are:

CDR1
(SEQ ID NO: 66)
DYYMN;

CDR2
(SEQ ID NO: 124)
RVNPSNGGTSYNQKFKG;
and

CDR3
(SEQ ID NO: 125)
RHNYPDY.

Another embodiment provides a nucleic acid encoding heavy chain (SEQ ID NO:125). An exemplary nucleic acid that encodes heavy chain (SEQ ID NO:125) is (SEQ ID NO: 126)
GAGGTCCAGCTGCAACAGTCTGGACCTGAACTGGTGAAGCCTGGGGCTTC

AGTGAAGATGTCCTGTAAGGCTTCTGGATACACATTCACTGACTACTACA

TGAACTGGGTGAAGCAGAGTCATGGAAAGAGCCTTGAGTGGATTGGACGT

GTTAATCCTAGCAATGGTGGTACTAGCTACAACCAGAAGTTCAAGGGCAA

GGCCACATTGACAGTAGACAAATCCCTCAGCGCAGCCTATATGCAGCTCA

ACAGCCTGACATCTGAGGACTCTGCGGTCTATTACTGTGCAAGAAGGCAT

AACTACCCTGACTACTGGGGCCAAGGCACCACTCTCACAGTCTCCTCA.

One embodiment provides an anti-B7H4 antibody, preferably a monoclonal antibody, or antigen binding fragment thereof that has a light chain containing CDRs according to SEQ ID Nos: 54, 55, and 121.

One embodiment provides an anti-B7H4 antibody, preferably a monoclonal antibody, or an antigen binding fragment thereof having a heavy chain containing CDRs according to SEQ ID Nos: 66, 124, and 125.

One embodiment provides an anti-B7H4 antibody, preferably a monoclonal antibody, or antigen binding fragment thereof that has a light chain containing CDRs according to SEQ ID Nos: 54, 55, and 121, and a heavy chain containing CDRs according to SEQ ID Nos: 66, 124, and 125.

One embodiment provides an anti-B7H4 antibody, preferably a monoclonal antibody, or an antigen binding fragment thereof having a light chain at least 50%, 60%, 70%, 80%, 85%, 90%, 95%, 99%, or 100% sequence identity to SEQ ID NO:120 and a heavy chain having at least 50%, 60%, 70%, 80%, 85%, 90%, 95%, 99%, or 100% sequence identity to SEQ ID NO:123.

j. B10D7 Sequences

In one embodiment an anti-B7H4 murine monoclonal antibody is produced by hybridoma clone B10D7 and contains two light chains and two heavy chains.

i. Light Chain

One embodiment provides an anti-B7H4 monoclonal antibody or antigen binding fragment thereof that has a light chain having at least 50%, 60%, 70%, 80%, 85%, 90%, 95%, 99%, or 100% sequence identity with the following amino acid sequence:

(SEQ ID NO: 13)
EIQMTQSPSSMSASLGDRITITCQATQDIVKSLNWYQQKPGKPPSFLIYY

TAQLAEGVPSRFSGSGSGSDYSLTISNLESEDFADYYCLQFYEFPPTFGG

GTKLEIK.

The CDRs of SEQ ID NO:13 are bolded and underlined and are:

CDR1
(SEQ ID NO: 14)
QATQDIVKSLN;

CDR2
(SEQ ID NO: 15)
YTAQLAE;
and

CDR3
(SEQ ID NO: 16)
LQFYEFPPT.

Another embodiment provides a nucleic acid that encodes the light chain (SEQ ID NO:13).

An exemplary nucleic acid that encodes light chain (SEQ ID NO:13) is

```
                                      (SEQ ID NO: 127)
GAAATCCAGATGACCCAGTCTCCATCCTCTATGTCTGCATCTCTGGGAGA

CAGAATAACCATCACTTGCCAGGCAACTCAAGACATTGTTAAGAGTTTAA

ACTGGTATCAACAAAAACCAGGGAAACCCCCTTCATTCCTGATCTATTAT

ACAGCTCAACTGGCAGAAGGGGTCCCGTCAAGGTTCAGTGGCAGTGGGTC

TGGGTCAGACTATTCTCTGACAATCAGCAACCTGGAGTCTGAAGATTTTG

CAGACTATTACTGTCTACAGTTTTATGAGTTTCCTCCGACGTTCGGTGGA

GGCACCAAGCTGGAAATCAA.
``` ii. Heavy Chain

One embodiment provides an anti-B7H4 murine monoclonal antibody or antigen binding fragment thereof that has a heavy chain having at least 50%, 60%, 70%, 80%, 85%, 90%, 95%, 99%, or 100% sequence identity with the following amino acid sequence:

```
                                      (SEQ ID NO: 128)
EVQLQQSGTVLARPGASVKMSCKASGYPFTSYWMHWVKQRPGQGLEWIGA

IYPGNSDTRYNPNFKGKANLTAVTSATTAYMELSSLTNEESAVYYCTSTW

THYFDYWGQGTTLTVSS.
```

The CDRs of SEQ ID NO:128 are bolded and underlined and are:

```
CDR1
                                       (SEQ ID NO: 9)
SYWMH;

CDR2
                                       (SEQ ID NO: 129)
AIYPGNSDTRYNPNFKG;
and

CDR3
                                       (SEQ ID NO: 130)
TWTHYFDY.
```

Another embodiment provides a nucleic acid encoding heavy chain (SEQ ID NO:128). An exemplary nucleic acid that encodes heavy chain (SEQ ID NO:130) is

```
                                      (SEQ ID NO: 131)
GAGGTTCAGCTCCAGCAGTCTGGGACTGTGCTGGCAAGGCCTGGGCTTC

AGTGAAGATGTCCTGCAAGGCTTCTGGCTACCCCTTTACCAGCTACTGGA

TGCACTGGGTAAAGCAGAGGCCTGGACAGGGTCTGGAATGGATTGGCGCT

ATTTATCCTGGAAATAGTGATACTAGGTACAACCCGAATTTCAAGGGCAA

GGCCAACCTGACTGCAGTCACATCTGCCACCACTGCCTACATGGAGCTCA

GCAGCCTGACAAATGAGGAATCTGCGGTCTATTACTGTACAAGTACCTGG

ACCCACTACTTTGACTACTGGGGCCAAGGCACCACTCTCACAGTCTCCTC

A.
```

One embodiment provides an anti-B7H4 antibody, preferably a monoclonal antibody, or antigen binding fragment thereof that has a light chain containing CDRs according to SEQ ID Nos: 14, 15, and 16.

One embodiment provides an anti-B7H4 antibody, preferably a monoclonal antibody, or an antigen binding fragment thereof having a heavy chain containing CDRs according to SEQ ID Nos: 9, 129, and 130.

One embodiment provides an anti-B7H4 antibody, preferably a monoclonal antibody, or antigen binding fragment thereof that has a light chain containing CDRs according to SEQ ID Nos: 14, 15, and 16 and a heavy chain containing CDRs according to SEQ ID Nos: 9, 129, and 130.

One embodiment provides an anti-B7H4 antibody, preferably a monoclonal antibody, or an antigen binding fragment thereof having a light chain at least 50%, 60%, 70%, 80%, 85%, 90%, 95%, 99%, or 100% sequence identity to SEQ ID NO:13 and a heavy chain having at least 50%, 60%, 70%, 80%, 85%, 90%, 95%, 99%, or 100% sequence identity to SEQ ID NO:128.

2. Antibody Compositions

The disclosed B7-H4-binding molecules can be antibodies or antigen binding fragments thereof. The disclosed antibodies and antigen binding fragments thereof include whole immunoglobulin (i.e., an intact antibody) of any class, fragments thereof, and synthetic proteins containing at least the antigen binding variable domain of an antibody. In some embodiments, the disclosed molecule contains both an antibody light chain as well as at least the variable domain of an antibody heavy chain. In other embodiments, such molecules can further include one or more of the $CH_1$, hinge, $CH_2$, $CH_3$, and $CH_4$ regions of the heavy chain (especially, the $CH_1$ and hinge regions, or the $CH_1$, hinge and $CH_2$ regions, or the $CH_1$, hinge, $CH_2$ and $CH_3$ regions). The antibody can be selected from any class of immunoglobulins, including IgM, IgG, IgD, IgA and IgE, and any isotype, including $IgG_1$, $IgG_2$, $IgG_3$ and $IgG_4$. In some embodiments, the constant domain is a complement fixing constant domain where it is desired that the antibody exhibit cytotoxic activity, and the class is typically $IgG_1$. In other embodiments, where such cytotoxic activity is not desirable, the constant domain can be of the $IgG_2$ or $IgG_4$ class. The antibody can include sequences from more than one class or isotype, and selecting particular constant domains to optimize desired effector functions is within the ordinary skill in the art.

The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the non-modified antibody or antibody fragment.

Techniques can also be adapted for the production of single-chain antibodies specific to B7-H4. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

One embodiment provides a monoclonal antibody obtained from a substantially homogeneous population of antibodies, i.e., the individual antibodies within the population are identical except for possible naturally occurring mutations that may be present in a small subset of the antibody molecules. Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

On embodiment provides antibodies and antigen binding fragments thereof the specifically bind to human B7-H4.

One embodiment provides antibodies produced by a hybridoma from the group consisting of B1A1, B1H1, B1H3, B1H10, B2E6, B4B2, B4E11, B6C8, B9H1, and B10D7.

a. Antibodies

The immunomodulatory agent can be an antibody. Suitable antibodies are known in the art or can be prepared by one of skill in the art. Nucleic acid and polypeptide sequences for B7-H4 are known in the art, and exemplary protein sequences are provided above. The sequences can be used, as discussed in more detail below, by one of skill in the art to prepare an antibody or antigen binding fragment thereof specific for B7-H4. The antibody, or antigen binding fragment therefore, can be an agonist or antagonist of B7-H4 signaling.

The activity (i.e., agonist or antagonist) of an antibody or antigen binding fragment thereof that is specific for B7-H4, can be determined using functional assays that are known in the art, and include the assays discussed below. Typically the assays include determining if the antibody or antigen binding fragment thereof increases (i.e., agonist) or decreases (i.e., antagonist) signaling through B7-H4. Because B7-H4 signal transduction results in a suppressive immune response, agonizing B7-H4 causes a suppressed or reduced immune response. Antagonizing B7-H4 signaling inhibits the immune suppressive response resulting in an overall increase in an immune response.

In some embodiments, the disclosed antibodies and antigen binding fragments thereof immunospecifically bind to B7-H4. In some embodiments, the antibody binds to an extracellular domain of B7-H4.

For example, molecules are provided that can immunospecifically bind to B7-H4:
 (I) arrayed on the surface of a cell (especially a live cell);
 (II) arrayed on the surface of a cell (especially a live cell) at an endogenous concentration;
 (III) arrayed on the surface of a live cell, and modulates binding between B7-H4 and a ligand thereof;
 (IV) arrayed on the surface of a live cell, and reduces or inhibits immune suppression by B7-H4;
 (V) arrayed on the surface of a live cell, and induces or enhances immune suppression by B7-H4;
 (VI) arrayed on the surface of a live cell, wherein the cell is a tumor cell;
 (VII) combinations of I-IV and VI;
 (VIII) combinations of I-III and V-IV; and
 (IX) arrayed on the surface of a live myeloid or lymphoid derived cancer cells (AML or ALL), and enhances apoptosis and differentiation resulting in reduced self-renewal of cancer stem cells.

In some embodiments, the molecules are capable of inducing antibody dependent cell cytotoxicity (ADCC), complement dependent cytotoxicity (CDC) or cellular apoptosis through other mechanisms, of B7-H4 expressing cell.

To prepare an antibody or antigen binding fragment thereof that specifically binds to B7-H4, purified proteins, polypeptides, fragments, fusions, or epitopes to B7-H4 or polypeptides expressed from nucleic acid sequences thereof, can be used. The antibodies or antigen binding fragments thereof can be prepared using any suitable methods known in the art such as those discussed in more detail below.

i. Human and Humanized Antibodies

Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge.

Optionally, the antibodies are generated in other species and "humanized" for administration in humans. Humanized forms of non-human (e.g., murine) antibodies are chimeric immunoglobulins, immunoglobulin chains or fragments thereof (such as Fv, Fab, Fab', F(ab')$_2$, or other antigen-binding subsequences of antibodies) which contain minimal sequence derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also contain residues that are found neither in the recipient antibody nor in the imported CDR or framework sequences. In general, the humanized antibody will contain substantially all of at least one, and typically two, variable domains, in which all or substantially all, of the CDR regions correspond to those of a non-human immunoglobulin and all or substantially all of the FR regions are those of a human immunoglobulin consensus sequence. The humanized antibody optimally also will contain at least a portion of an immunoglobulin constant region (Fc), typically that of a human immunoglobulin.

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed by substituting rodent CDRs or CDR sequences for the corresponding sequences of a human antibody. Accordingly, a humanized form of a nonhuman antibody (or a fragment thereof) is a chimeric antibody or fragment, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody. Another method uses a particular framework derived from the consensus sequence of all human antibodies of a particular subgroup of light or heavy chains. The same framework may be used for several different humanized antibodies.

It is further important that antibodies be humanized with retention of high affinity for the antigen and other favorable biological properties. To achieve this goal, humanized antibodies can be prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

The antibody can be bound to a substrate or labeled with a detectable moiety or both bound and labeled. The detectable moieties contemplated with the present compositions include fluorescent, enzymatic and radioactive markers.

ii. Single-Chain Antibodies

Methods for the production of single-chain antibodies are well known to those of skill in the art. A single chain antibody is created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation. These Fvs lack the constant regions (Fc) present in the heavy and light chains of the native antibody.

iii. Monovalent Antibodies

In vitro methods are also suitable for preparing monovalent antibodies. Digestion of antibodies to produce fragments thereof, particularly, Fab fragments, can be accomplished using routine techniques known in the art. For instance, digestion can be performed using papain. Papain digestion of antibodies typically produces two identical antigen binding fragments, called Fab fragments, each with a single antigen binding site, and a residual Fc fragment. Pepsin treatment yields a fragment, called the F(ab')2 fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

iv. Hybrid Antibodies

The antibody can be a hybrid antibody. In hybrid antibodies, one heavy and light chain pair is homologous to that found in an antibody raised against one epitope, while the other heavy and light chain pair is homologous to a pair found in an antibody raised against another epitope. This results in the property of multi-functional valency, i.e., ability to bind at least two different epitopes simultaneously. Such hybrids can be formed by fusion of hybridomas producing the respective component antibodies, or by recombinant techniques. Such hybrids may, of course, also be formed using chimeric chains.

v. Conjugates or Fusions of Antibody Fragments

The targeting function of the antibody can be used therapeutically by coupling the antibody or a fragment thereof with a therapeutic agent. Such coupling of the antibody or fragment (e.g., at least a portion of an immunoglobulin constant region (Fc)) with the therapeutic agent can be achieved by making an immunoconjugate or by making a fusion protein, comprising the antibody or antibody fragment and the therapeutic agent.

Such coupling of the antibody or fragment with the therapeutic agent can be achieved by making an immunoconjugate or by making a fusion protein, or by linking the antibody or fragment to a nucleic acid such as an siRNA, comprising the antibody or antibody fragment and the therapeutic agent.

In some embodiments, the antibody is modified to alter its half-life. In some embodiments, it is desirable to increase the half-life of the antibody so that it is present in the circulation or at the site of treatment for longer periods of time. For example, it may be desirable to maintain titers of the antibody in the circulation or in the location to be treated for extended periods of time. Antibodies can be engineered with Fc variants that extend half-life, e.g., using Xtend™ antibody half-life prolongation technology (Xencor, Monrovia, CA). In other embodiments, the half-life of the anti-DNA antibody is decreased to reduce potential side effects. The conjugates disclosed can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin.

vi. Exemplary B7H4 Antibodies

Exemplary B7H4 antibodies or antigen binding fragments are disclosed herein. The antibodies can include one or more heavy chain and one or more light chain of mouse anti-human B7H4 antibody B1H1 or B1H10. In some embodiments, the B7H45 antibody includes some or all of the light chain CDRs, the entire light chain variable region, some or all of the heavy chain CDRs, the entire heavy chain variable region, or a combination thereof of any of mouse anti-human B7H4 antibody B1H1 or B1H10. Exemplary combinations are disclosed below.

An anti-B7H4 antibody or antigen binding fragment thereof having a light chain with an amino acid sequence according to SEQ ID NO:24 and a heavy chain having an amino acid sequence according to SEQ ID NO:38.

An anti-B7H4 antibody or antigen binding fragment thereof having a light chain with an amino acid sequence according to SEQ ID NO:24 and a heavy chain having an amino acid sequence according to SEQ ID NO:39.

An anti-B7H4 antibody or antigen binding fragment thereof having a light chain with an amino acid sequence according to SEQ ID NO:24 and a heavy chain having an amino acid sequence according to SEQ ID NO:40.

An anti-B7H4 antibody or antigen binding fragment thereof having a light chain with an amino acid sequence according to SEQ ID NO:24 and a heavy chain having an amino acid sequence according to SEQ ID NO:41.

An anti-B7H4 antibody or antigen binding fragment thereof having a light chain with an amino acid sequence according to SEQ ID NO:24 and a heavy chain having an amino acid sequence according to SEQ ID NO:42.

An anti-B7H4 antibody or antigen binding fragment thereof with a light chain having an amino acid sequence according to SEQ ID NO:24 and a heavy chain having an amino acid sequence according to SEQ ID NO:43.

An anti-B7H4 antibody or antigen binding fragment thereof with a light chain having an amino acid sequence according to SEQ ID NO:24 and a heavy chain having an amino acid sequence according to SEQ ID NO:44.

An anti-B7H4 antibody or antigen binding fragment thereof with a light chain having an amino acid sequence according to SEQ ID NO:24 and a heavy chain having an amino acid sequence according to SEQ ID NO:45.

An anti-B7H4 antibody or antigen binding fragment thereof with a light chain having an amino acid sequence according to SEQ ID NO:25 and a heavy chain having an amino acid sequence according to SEQ ID NO:38.

An anti-B7H4 antibody or antigen binding fragment thereof with a light chain having an amino acid sequence according to SEQ ID NO:25 and a heavy chain having an amino acid sequence according to SEQ ID NO:39.

An anti-B7H4 antibody or antigen binding fragment thereof with a light chain having an amino acid sequence according to SEQ ID NO:25 and a heavy chain having an amino acid sequence according to SEQ ID NO:40.

An anti-B7H4 antibody or antigen binding fragment thereof with a light chain having an amino acid sequence according to SEQ ID NO:25 and a heavy chain having an amino acid sequence according to SEQ ID NO:41.

An anti-B7H4 antibody or antigen binding fragment thereof with a light chain having an amino acid sequence according to SEQ ID NO:25 and a heavy chain having an amino acid sequence according to SEQ ID NO:42.

An anti-B7H4 antibody or antigen binding fragment thereof with a light chain having an amino acid sequence according to SEQ ID NO:25 and a heavy chain having an amino acid sequence according to SEQ ID NO:43.

An anti-B7H4 antibody or antigen binding fragment thereof with a light chain having an amino acid sequence according to SEQ ID NO:25 and a heavy chain having an amino acid sequence according to SEQ ID NO:44.

An anti-B7H4 antibody or antigen binding fragment thereof with a light chain having an amino acid sequence according to SEQ ID NO:25 and a heavy chain having an amino acid sequence according to SEQ ID NO:45.

An anti-B7H4 antibody or antigen binding fragment thereof with a light chain having an amino acid sequence according to SEQ ID NO:26 and a heavy chain having an amino acid sequence according to SEQ ID NO:38.

An anti-B7H4 antibody or antigen binding fragment thereof with a light chain having an amino acid sequence according to SEQ ID NO:26 and a heavy chain having an amino acid sequence according to SEQ ID NO:39.

An anti-B7H4 antibody or antigen binding fragment thereof with a light chain having an amino acid sequence according to SEQ ID NO:26 and a heavy chain having an amino acid sequence according to SEQ ID NO:40.

An anti-B7H4 antibody or antigen binding fragment thereof with a light chain having an amino acid sequence according to SEQ ID NO:26 and a heavy chain having an amino acid sequence according to SEQ ID NO:41.

An anti-B7H4 antibody or antigen binding fragment thereof with a light chain having an amino acid sequence according to SEQ ID NO:26 and a heavy chain having an amino acid sequence according to SEQ ID NO:42.

An anti-B7H4 antibody or antigen binding fragment thereof with a light chain having an amino acid sequence according to SEQ ID NO:26 and a heavy chain having an amino acid sequence according to SEQ ID NO:43.

An anti-B7H4 antibody or antigen binding fragment thereof with a light chain having an amino acid sequence according to SEQ ID NO:26 and a heavy chain having an amino acid sequence according to SEQ ID NO:44.

An anti-B7H4 antibody or antigen binding fragment thereof with a light chain having an amino acid sequence according to SEQ ID NO:26 and a heavy chain having an amino acid sequence according to SEQ ID NO:45.

An anti-B7H4 antibody or antigen binding fragment thereof with a light chain having an amino acid sequence according to SEQ ID NO:27 and a heavy chain having an amino acid sequence according to SEQ ID NO:38.

An anti-B7H4 antibody or antigen binding fragment thereof with a light chain having an amino acid sequence according to SEQ ID NO:27 and a heavy chain having an amino acid sequence according to SEQ ID NO:39.

An anti-B7H4 antibody or antigen binding fragment thereof with a light chain having an amino acid sequence according to SEQ ID NO:27 and a heavy chain having an amino acid sequence according to SEQ ID NO:40.

An anti-B7H4 antibody or antigen binding fragment thereof with a light chain having an amino acid sequence according to SEQ ID NO:27 and a heavy chain having an amino acid sequence according to SEQ ID NO:41.

An anti-B7H4 antibody or antigen binding fragment thereof with a light chain having an amino acid sequence according to SEQ ID NO:27 and a heavy chain having an amino acid sequence according to SEQ ID NO:42.

An anti-B7H4 antibody or antigen binding fragment thereof with a light chain having an amino acid sequence according to SEQ ID NO:27 and a heavy chain having an amino acid sequence according to SEQ ID NO:43.

An anti-B7H4 antibody or antigen binding fragment thereof with a light chain having an amino acid sequence according to SEQ ID NO:27 and a heavy chain having an amino acid sequence according to SEQ ID NO:44.

An anti-B7H4 antibody or antigen binding fragment thereof with a light chain having an amino acid sequence according to SEQ ID NO:27 and a heavy chain having an amino acid sequence according to SEQ ID NO:45.

An anti-B7H4 antibody or antigen binding fragment thereof with a light chain having an amino acid sequence according to SEQ ID NO:28 and a heavy chain having an amino acid sequence according to SEQ ID NO:38.

An anti-B7H4 antibody or antigen binding fragment thereof with a light chain having an amino acid sequence according to SEQ ID NO:28 and a heavy chain having an amino acid sequence according to SEQ ID NO:39.

An anti-B7H4 antibody or antigen binding fragment thereof with a light chain having an amino acid sequence according to SEQ ID NO:28 and a heavy chain having an amino acid sequence according to SEQ ID NO:40.

An anti-B7H4 antibody or antigen binding fragment thereof with a light chain having an amino acid sequence according to SEQ ID NO:28 and a heavy chain having an amino acid sequence according to SEQ ID NO:41.

An anti-B7H4 antibody or antigen binding fragment thereof with a light chain having an amino acid sequence according to SEQ ID NO:28 and a heavy chain having an amino acid sequence according to SEQ ID NO:42.

An anti-B7H4 antibody or antigen binding fragment thereof with a light chain having an amino acid sequence according to SEQ ID NO:28 and a heavy chain having an amino acid sequence according to SEQ ID NO:43.

An anti-B7H4 antibody or antigen binding fragment thereof with a light chain having an amino acid sequence according to SEQ ID NO:28 and a heavy chain having an amino acid sequence according to SEQ ID NO:44.

An anti-B7H4 antibody or antigen binding fragment thereof with a light chain having an amino acid sequence according to SEQ ID NO:28 and a heavy chain having an amino acid sequence according to SEQ ID NO:45.

2. Proteins and Polypeptides a. Protein and Polypeptide Compositions

The immunomodulatory agent can be a protein, polypeptide, or fusion protein. For example, the immunomodulatory agent can be an isolated or recombinant protein or polypeptide, or functional fragment, variant, or fusion protein thereof of B7-H4.

The protein or polypeptide, or functional fragment, variant, or fusion protein thereof can be an agonist or an antagonist. For example, in some embodiments an antagonist of B7-H4 is a B7-H4 polypeptide or a fragment or fusion protein thereof that binds to a ligand of B7-H4. The polypeptide can be a soluble fragment, for example the extracellular domain of B7-H4, or a functional fragment thereof, or a fusion protein thereof. In some embodiments, a soluble ligand of B7-H4 may serve as an agonist, increasing signal transduction through B7-H4.

The activity (i.e., agonist or antagonist) of a protein or polypeptide of B7-H4, or any fragment, variant or fusion protein thereof can be determined using functional assays that are known in the art, and include the assays discussed below. Typically the assays include determining if the protein, polypeptide or fragment, variant or fusion protein thereof increases (i.e., agonist) or decreases (i.e., antagonist) signaling through the B7-H4 receptor. In some embodiments the assay includes determining if the protein, polypeptide or fragment, variant, or fusion protein thereof increases (i.e., agonist) or decreases (i.e., antagonist) the immune response associated with B7-H4. Typically the assays include determining if the protein, polypeptide or fragment, variant, or fusion protein thereof increases (i.e., agonist) or decreases (i.e., antagonist) signaling through B7-H4. In some embodiments the assay includes determining if the protein, polypeptide or fragment, variant, or fusion protein thereof decreases (i.e., agonist) or increases (i.e., antagonist) an immune response negatively regulated by B7-H4. In some embodiments the assay includes determining if the protein, polypeptide or fragment, variant, or fusion protein thereof increases (i.e., antagonist) the apoptosis and differentiation of acute myeloid leukemia cells and acute lymphoblastic leukemia cells resulting in reduced self-renewal capacity of AML and ALL stem cells.

Nucleic acid and polypeptide sequences for B7-H4 are known in the art and exemplary protein and peptide sequences are provided above. The sequences can be used, as discussed in more detail below, by one of skill in the art to prepare any protein or polypeptide of B7-H4, or any fragment, variant, or fusion protein thereof. Generally, the proteins, polypeptides, fragments, variants, and fusions thereof of B7-H4 are expressed from nucleic acids that include sequences that encode a signal sequence. The signal sequence is generally cleaved from the immature polypeptide to produce the mature polypeptide lacking the signal sequence. The signal sequence can be replaced by the signal sequence of another polypeptide using standard molecule biology techniques to affect the expression levels, secretion, solubility, or other property of the polypeptide B7-H4 proteins with and without a signal sequence are disclosed. It is understood that in some cases, the mature protein as it is known or described in the art, i.e., the protein sequence without the signal sequence, is a putative mature protein. During normal cell expression, a signal sequence can be removed by a cellular peptidase to yield a mature protein. The sequence of the mature protein can be determined or confirmed using methods that are known in the art.

i. Fragments

As used herein, a fragment of B7-H4 refers to any subset of the polypeptide that is at least one amino acid shorter than full length protein. Useful fragments include those that retain the ability to bind to their natural ligand or ligands. A polypeptide that is a fragment of any full-length B7-H4 typically has at least 20 percent, 30 percent, 40 percent, 50 percent, 60 percent, 70 percent, 80 percent, 90 percent, 95 percent, 98 percent, 99 percent, 100 percent, or even more than 100 percent of the ability to bind its natural ligand respectively as compared to the full-length protein.

Fragments of B7-H4 include cell free fragments. Cell free polypeptides can be fragments of full-length, transmembrane, polypeptides that may be shed, secreted or otherwise extracted from the producing cells. Cell free fragments of polypeptides can include some or all of the extracellular domain of the polypeptide, and lack some or all of the intracellular and/or transmembrane domains of the full-length protein. In one embodiment, polypeptide fragments include the entire extracellular domain of the full-length protein. In other embodiments, the cell free fragments of the polypeptides include fragments of the extracellular domain that retain biological activity of full-length protein. The extracellular domain can include 1, 2, 3, 4, or 5 contiguous amino acids from the transmembrane domain, and/or 1, 2, 3, 4, or 5 contiguous amino acids from the signal sequence. Alternatively, the extracellular domain can have 1, 2, 3, 4, 5 or more amino acids removed from the C-terminus, N-terminus, or both. In some embodiments the extracellular domain is the only functional domain of the fragment (e.g., the ligand binding domain).

ii. Variants

Variants of B7-H4, and fragments thereof are also provided. In some embodiments, the variant is at least 50, 60, 70, 80, 85, 90, 95, 96, 97, 98, or 99 percent identical to any one of SEQ ID NO: 1. Useful variants include those that increase biological activity, as indicated by any of the assays described herein, or that increase half-life or stability of the protein. The protein and polypeptides of B7-H4, and fragments, variants, and fusion proteins thereof can be engineered to increase biological activity. For example, in some embodiments, a B7-H4 polypeptide, protein, or fragment, variant or fusion thereof has been modified with at least one amino acid substitution, deletion, or insertion that increases a function thereof.

Finally, variant polypeptides can be engineered to have an increased half-life relative to wild type. These variants typically are modified to resist enzymatic degradation. Exemplary modifications include modified amino acid residues and modified peptide bonds that resist enzymatic degradation. Various modifications to achieve this are known in the art. The variants can be modified to adjust for effects of affinity for the receptor on the half-life of proteins, polypeptides, fragments, or fusions thereof at serum and endosomal pH.

iii. Fusion Proteins

Fusion polypeptides have a first fusion partner including all or a part of a polypeptide B7-H4 fused to a second polypeptide directly or via a linker peptide sequence that is fused to the second polypeptide. The fusion proteins optionally contain a domain that functions to dimerize or multimerize two or more fusion proteins. The peptide/polypeptide linker domain can either be a separate domain, or alternatively can be contained within one of the other domains (first polypeptide or second polypeptide) of the fusion protein. Similarly, the domain that functions to dimerize or multimerize the fusion proteins can either be a separate domain, or alternatively can be contained within one of the other domains (first polypeptide, second polypeptide or peptide/polypeptide linker domain) of the fusion protein. In one embodiment, the dimerization/multimerization domain and the peptide/polypeptide linker domain are the same.

Fusion proteins disclosed herein are of formula I:

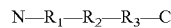

wherein "N" represents the N-terminus of the fusion protein, "C" represents the C-terminus of the fusion protein. In some embodiments, "$R_1$" is a polypeptide or protein of B7-H4 or fragment or variant thereof, "$R_2$" is an optional peptide/polypeptide linker domain, and "$R_3$" is a second polypeptide. Alternatively, $R_3$ may be a polypeptide or protein of B7-H4, or fragment or variant thereof and $R_1$ may be a second polypeptide. In some embodiments, the B7-H4 polypeptide is the extracellular domain or a fragment thereof such as the Ig-like C2-domain, or the region framed by the cysteines that form a disulfide bond as discussed above.

Dimerization or multimerization can occur between or among two or more fusion proteins through dimerization or multimerization domains. Alternatively, dimerization or multimerization of fusion proteins can occur by chemical crosslinking. The dimers or multimers that are formed can be homodimeric/homomultimeric or heterodimeric/heteromultimeric.

In some embodiments, the fusion protein includes the extracellular domain of B7-H4, or a fragment or variant thereof, fused to an Ig Fc region. Recombinant Ig fusion proteins can be prepared by fusing the coding region of the extracellular domain of an extracellular domain or a fragment or variant thereof to the Fc region of human IgG1, IgG2, IgG3 or IgG4 or mouse IgG2a, or other suitable Ig domain, as described previously (Chapoval, et al., *Methods Mol. Med.,* 45:247-255 (2000)).

iv. Polypeptide Modifications

The polypeptides and fusion proteins may be modified by chemical moieties that may be present in polypeptides in a normal cellular environment, for example, phosphorylation, methylation, amidation, sulfation, acylation, glycosylation, sumoylation and ubiquitylation. Fusion proteins may also be modified with a label capable of providing a detectable signal, either directly or indirectly, including, but not limited to, radioisotopes and fluorescent compounds.

The polypeptides and fusion proteins may also be modified by chemical moieties that are not normally added to polypeptides in a cellular environment. For example, the disclosed fusion proteins may also be modified by covalent attachment of polymer chains, including, but not limited to, polyethylene glycol polymer (PEG) chains (i.e., pegylation). Conjugation of macromolecules to PEG has emerged recently as an effective strategy to alter the pharmacokinetic (PK) profiles of a variety of drugs, and thereby to improve their therapeutic potential. PEG conjugation increases retention of drugs in the circulation by protecting against enzymatic digestion, slowing filtration by the kidneys and reducing the generation of neutralizing antibodies. In addition, PEG conjugates can be used to allow multimerization of the fusion proteins.

Modifications may be introduced into the molecule by reacting targeted amino acid residues of the polypeptide with an organic derivatizing agent that is capable of reacting with selected side chains or terminal residues. Another modification is cyclization of the protein.

Examples of chemical derivatives of the polypeptides include lysinyl and amino terminal residues derivatized with succinic or other carboxylic acid anhydrides. Derivatization with a cyclic carboxylic anhydride has the effect of reversing the charge of the lysinyl residues. Other suitable reagents for derivatizing amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Carboxyl side groups, aspartyl or glutamyl, may be selectively modified by reaction with carbodiimides (R—N=C=N—R') such as 1-cyclohexyl-3-(2-morpholinyl-(4-ethyl)carbodiimide or 1-ethyl-3-(4-azonia-4,4-dimethylpentyl) carbodiimide. Furthermore, aspartyl and glutamyl residues can be converted to asparaginyl and glutaminyl residues by reaction with ammonia. Fusion proteins may also include one or more D-amino acids that are substituted for one or more L-amino acids.

v. Modified Binding Properties

Binding properties of the proteins, polypeptides, fragments, variants and fusions thereof are relevant to the dose and dose regimen to be administered. In one embodiment the disclosed the proteins, polypeptides, fragments, variants and fusions thereof have binding properties to a B7-H4 ligand that demonstrate a higher term, or higher percentage, of occupancy of a binding site (e.g., on the ligand) relative to other receptor molecules that bind thereto. In other embodiments, the disclosed proteins, polypeptides, fragments, variants and fusions thereof have reduced binding affinity to a B7-H4 ligand relative to wild type protein.

In some embodiments the proteins, polypeptides, fragments, variants and fusions thereof have a relatively high affinity for B7-H4 ligand, and may therefore have a relatively slow off rate. In other embodiments, the proteins polypeptides, fragments, variants and fusions thereof are administered intermittently over a period of days, weeks or months to dampen immune responses which are allowed to recover prior to the next administration, which may serve to alter the immune response without completely turning the immune response on or off and may avoid long term side effects.

3. Isolated Nucleic Acid Molecules

Isolated nucleic acid sequences encoding the proteins, polypeptides, fragments, variants and fusions thereof are disclosed herein. As used herein, "isolated nucleic acid" refers to a nucleic acid that is separated from other nucleic acid molecules that are present in a mammalian genome, including nucleic acids that normally flank one or both sides of the nucleic acid in a mammalian genome. The term "isolated" as used herein with respect to nucleic acids also includes the combination with any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule independent of other sequences (e.g., a chemically synthesized nucleic acid, or a cDNA or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

Nucleic acids encoding the proteins, polypeptides, fragments, variants and fusions thereof may be optimized for expression in the expression host of choice. Codons may be substituted with alternative codons encoding the same amino acid to account for differences in codon usage between the mammal from which the nucleic acid sequence is derived and the expression host. In this manner, the nucleic acids may be synthesized using expression host-preferred codons.

Nucleic acids can be in sense or antisense orientation, or can be complementary to a reference sequence encoding a polypeptide or protein of B7-H4. Nucleic acids can be DNA, RNA, or nucleic acid analogs. Nucleic acid analogs can be modified at the base moiety, sugar moiety, or phosphate backbone. Such modification can improve, for example, stability, hybridization, or solubility of the nucleic acid. Modifications at the base moiety can include deoxyuridine for deoxythymidine, and 5-methyl-2'-deoxycytidine or 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone.

Nucleic acids encoding polypeptides can be administered to subjects in need thereof. Nucleic delivery involves introduction of "foreign" nucleic acids into a cell and ultimately, into a live animal. Compositions and methods for delivering nucleic acids to a subject are known in the art (see Understanding Gene Therapy, Lemoine, N. R., ed., BIOS Scientific Publishers, Oxford, 2008).

4. Vectors and Host Cells

Vectors encoding the proteins, polypeptides, fragments, variants and fusions thereof are also provided. Nucleic acids, such as those described above, can be inserted into vectors for expression in cells. As used herein, a "vector" is a replicon, such as a plasmid, phage, virus or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalo virus, retroviruses, vaccinia viruses, adenoviruses, and adeno-associated viruses. Numerous vectors and expression systems are commercially available from such corporations as Novagen (Madison, WI), Clontech (Palo Alto, CA), Stratagene (La Jolla, CA), and Invitrogen Life Technologies (Carlsbad, CA).

An expression vector can include a tag sequence. Tag sequences, are typically expressed as a fusion with the encoded polypeptide. Such tags can be inserted anywhere within the polypeptide including at either the carboxyl or amino terminus. Examples of useful tags include, but are not limited to, green fluorescent protein (GFP), glutathione S-transferase (GST), polyhistidine, c-myc, hemagglutinin, Flag™ tag (Kodak, New Haven, CT), maltose E binding protein and protein A. In one embodiment, a nucleic acid molecule encoding one of the disclosed polypeptides is present in a vector containing nucleic acids that encode one or more domains of an Ig heavy chain constant region, for example, having an amino acid sequence corresponding to the hinge, $C_H2$ and $C_H3$ regions of a human immunoglobulin Cγ1 chain.

Vectors containing nucleic acids to be expressed can be transferred into host cells. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Host cells (e.g., a prokaryotic cell or a eukaryotic cell such as a CHO cell) can be used to, for example, produce the proteins, polypeptides, fragments, variants and fusions thereof described herein.

The vectors described can be used to express the proteins, polypeptides, fragments, variants and fusions thereof in cells. An exemplary vector includes, but is not limited to, an adenoviral vector. One approach includes nucleic acid transfer into primary cells in culture followed by autologous transplantation of the ex vivo transformed cells into the host, either systemically or into a particular organ or tissue. Ex vivo methods can include, for example, the steps of harvesting cells from a subject, culturing the cells, transducing them with an expression vector, and maintaining the cells under conditions suitable for expression of the encoded polypeptides. These methods are known in the art of molecular biology. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject. In one embodiment, expression vectors containing nucleic acids encoding fusion proteins are transfected into cells that are administered to a subject in need thereof.

In vivo nucleic acid therapy can be accomplished by direct transfer of a functionally active DNA into mammalian somatic tissue or organ in vivo. For example, nucleic acids encoding polypeptides disclosed herein can be administered directly to lymphoid tissues. Alternatively, lymphoid tissue specific targeting can be achieved using lymphoid tissue-specific transcriptional regulatory elements (TREs) such as a B lymphocyte-, T lymphocyte-, or dendritic cell-specific TRE. Lymphoid tissue specific TREs are known in the art.

Nucleic acids may also be administered in vivo by viral means. Nucleic acid molecules encoding fusion proteins may be packaged into retrovirus vectors using packaging cell lines that produce replication-defective retroviruses, as is well-known in the art. Other virus vectors may also be used, including recombinant adenoviruses and vaccinia virus, which can be rendered non-replicating. In addition to naked DNA or RNA, or viral vectors, engineered bacteria may be used as vectors.

Nucleic acids may also be delivered by other carriers, including liposomes, polymeric micro- and nanoparticles and polycations such as asialoglycoprotein/polylysine.

In addition to virus- and carrier-mediated gene transfer in vivo, physical means well-known in the art can be used for direct transfer of DNA, including administration of plasmid DNA and particle-bombardment mediated gene transfer.

5. Small Molecules

The immunomodulatory agent can be a small molecule. Small molecules agonists and antagonists B7-H4 are known in the art or can be identified using routine screening methods.

In some embodiments, screening assays can include random screening of large libraries of test compounds. Alternatively, the assays may be used to focus on particular classes of compounds suspected of modulating the level of B7-H4. Assays can include determinations of B7-H4 signaling activity, or inhibitory response mediated by B7-H4. Other assays can include determinations of nucleic acid transcription or translation, mRNA levels, mRNA stability, mRNA degradation, transcription rates, and translation rates.

C. Pharmaceutical Compositions

Pharmaceutical compositions including the disclosed immunomodulatory agents are provided. Pharmaceutical compositions containing the immunomodulatory agent can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

For the disclosed immunomodulatory agents, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For the disclosed immunomodulatory agents, generally dosage levels of 0.001 to 20 mg/kg of body weight daily are administered to mammals. Generally, for intravenous injection or infusion, dosage may be lower.

In certain embodiments, the immunomodulatory agent is administered locally, for example by injection directly into a site to be treated. Typically, the injection causes an increased localized concentration of the immunomodulatory agent composition which is greater than that which can be achieved by systemic administration. The immunomodulatory agent compositions can be combined with a matrix as described above to assist in creating an increased localized concentration of the polypeptide compositions by reducing the passive diffusion of the polypeptides out of the site to be treated.

1. Formulations for Parenteral Administration

In some embodiments, compositions disclosed herein, including those containing peptides and polypeptides, are administered in an aqueous solution, by parenteral injection. The formulation may also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Oral Administration

In embodiments the compositions are formulated for oral delivery. Oral solid dosage forms are described generally in Remington's Pharmaceutical Sciences, 18th Ed. 1990 (Mack Publishing Co. Easton PA 18042) at Chapter 89. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the disclosed. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder (e.g., lyophilized) form. Liposomal or proteinoid encapsulation may be used to formulate the compositions. Liposomal encapsulation may be used and the liposomes may be derivatized with various polymers (e.g., U.S. Pat. No. 5,013, 556). See also Marshall, K. In: Modern Pharmaceutics Edited by G. S. Banker and C. T. Rhodes Chapter 10, 1979. In general, the formulation will include the peptide (or chemically modified forms thereof) and inert ingredients which protect peptide in the stomach environment, and release of the biologically active material in the intestine.

The agents can be chemically modified so that oral delivery of the derivative is efficacious. Generally, the chemical modification contemplated is the attachment of at least one moiety to the component molecule itself, where the moiety permits uptake into the blood stream from the stomach or intestine, or uptake directly into the intestinal mucosa. Also desired is the increase in overall stability of the component or components and increase in circulation time in the body. PEGylation is an exemplary chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane [see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) *J. Appl. Biochem.* 4:185-189].

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

Controlled release oral formulations may be desirable. The agent can be incorporated into an inert matrix which permits release by either diffusion or leaching mechanisms, e.g., gums. Slowly degenerating matrices may also be incorporated into the formulation. Another form of a controlled release is based on the Oros therapeutic system (Alza Corp.), i.e., the drug is enclosed in a semipermeable membrane which allows water to enter and push drug out through a single small opening due to osmotic effects.

For oral formulations, the location of release may be the stomach, the small intestine (the duodenum, the jejunum, or the ileum), or the large intestine. In some embodiments, the release will avoid the deleterious effects of the stomach environment, either by protection of the agent (or derivative) or by release of the agent (or derivative) beyond the stomach environment, such as in the intestine. To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D™, Aquateric™ cellulose acetate phthalate (CAP), Eudragit L™, Eudragit S™, and Shellac™. These coatings may be used as mixed films.

3. Formulations for Topical Administration

The disclosed immunomodulatory agents can be applied topically. Topical administration does not work well for most peptide formulations, although it can be effective especially if applied to the lungs, nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator.

Transdermal formulations may also be prepared. These will typically be ointments, lotions, sprays, or patches, all of which can be prepared using standard technology. Transdermal formulations may require the inclusion of penetration enhancers.

4. Controlled Delivery Polymeric Matrices

The immunomodulatory agents disclosed herein can also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where the agent is dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of fusion polypeptides or nucleic acids encoding the fusion polypeptides, although in some embodiments biodegradable matrices are preferred. These may be natural or synthetic polymers, although synthetic polymers are preferred in some embodiments due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release*, 5:13-22 (1987); Mathiowitz, et al., *Reactive Polymers*, 6:275-283 (1987); and Mathiowitz, et al., *J. Appl. Polymer Sci.*, 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

III. Methods of Manufacture

A. Methods of Making Antibodies

The antibodies can be generated in cell culture, in phage, or in various animals, including but not limited to cows, rabbits, goats, mice, rats, hamsters, guinea pigs, sheep, dogs, cats, monkeys, chimpanzees, apes. Therefore, in one embodiment, an antibody is a mammalian antibody. Phage techniques can be used to isolate an initial antibody or to generate variants with altered specificity or avidity characteristics. Such techniques are routine and well known in the art. In one embodiment, the antibody is produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include Delves, *Antibody Production: Essential Techniques* (Wiley, 1997); Shephard, et al., *Monoclonal Antibodies* (Oxford University Press, 2000); Goding, *Monoclonal Antibodies: Principles and Practice* (Academic Press, 1993); *Current Protocols in Immunology* (John Wiley & Sons, most recent edition).

The disclosed antibodies can be modified by recombinant means to increase greater efficacy of the antibody in mediating the desired function. Thus, it is within the scope of the invention that antibodies can be modified by substitutions using recombinant means. Typically, the substitutions will be conservative substitutions. For example, at least one amino acid in the constant region of the antibody can be replaced with a different residue. See, e.g., U.S. Pat. Nos. 5,624,821, 6,194,551, Application No. WO 9958572; and Angal, et al., Mol.

Immunol. 30:105-08 (1993). The modification in amino acids includes deletions, additions, and substitutions of amino acids. In some cases, such changes are made to reduce undesired activities, e.g., complement-dependent cytotoxicity. Frequently, the antibodies are labeled by joining, either covalently or non-covalently, a substance which provides for a detectable signal. A wide variety of labels and conjugation techniques are known and are reported extensively in both the scientific and patent literature. These antibodies can be screened for binding to proteins, polypeptides, or fusion proteins of B7-H4. See, e.g., *Antibody Engineering: A Practical Approach* (Oxford University Press, 1996).

For example, suitable antibodies with the desired biologic activities can be identified using in vitro assays including but not limited to: proliferation, migration, adhesion, soft agar growth, angiogenesis, cell-cell communication, apoptosis, transport, signal transduction, and in vivo assays such as the inhibition of tumor growth. The antibodies provided herein can also be useful in diagnostic applications. As capture or non-neutralizing antibodies, they can be screened for the ability to bind to the specific antigen without inhibiting the receptor-binding or biological activity of the antigen. As neutralizing antibodies, the antibodies can be useful in competitive binding assays.

Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the non-modified antibody or antibody fragment.

Techniques can also be adapted for the production of single-chain antibodies specific to an antigenic peptide. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

A monoclonal antibody is obtained from a substantially homogeneous population of antibodies, i.e., the individual antibodies within the population are identical except for possible naturally occurring mutations that may be present in a small subset of the antibody molecules. Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

Monoclonal antibodies can be made using any procedure which produces monoclonal antibodies. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

Antibodies may also be made by recombinant DNA methods. DNA encoding the disclosed antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques.

Methods of making antibodies using protein chemistry are also known in the art. One method of producing proteins comprising the antibodies is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, CA). One skilled in the art can readily appreciate that a peptide or polypeptide corresponding to the antibody, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. Alternatively, the peptide or polypeptide is independently synthesized in vivo as described above. Once isolated, these independent peptides or polypeptides may be linked to form an antibody or antigen binding fragment thereof via similar peptide condensation reactions.

For example, enzymatic ligation of cloned or synthetic peptide segments allow relatively short peptide fragments to be joined to produce larger peptide fragments, polypeptides or whole protein domains. Alternatively, native chemical ligation of synthetic peptides can be utilized to synthetically construct large peptides or polypeptides from shorter peptide fragments. This method includesa two-step chemical reaction. The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site.

B. Methods for Producing Proteins

The disclosed proteins, polypeptides, fragments, variants and fusions thereof can be manufactured using conventional techniques that are known in the art. Isolated fusion proteins can be obtained by, for example, chemical synthesis or by recombinant production in a host cell. To recombinantly produce a protein, polypeptide, fragment, variant or fusion thereof, a nucleic acid containing a nucleotide sequence encoding the protein, polypeptide, fragment, variant or fusion thereof can be used to transform, transduce, or transfect a bacterial or eukaryotic host cell (e.g., an insect, yeast, or mammalian cell). In general, nucleic acid constructs include a regulatory sequence operably linked to a nucleotide sequence encoding the protein, polypeptide, fragment, variant or fusion thereof. Regulatory sequences (also referred to herein as expression control sequences) typically do not encode a gene product, but instead affect the expression of the nucleic acid sequences to which they are operably linked.

Useful prokaryotic and eukaryotic systems for expressing and producing polypeptides are well known in the art include, for example, *Escherichia coli* strains such as BL-21, and cultured mammalian cells such as CHO cells.

In eukaryotic host cells, a number of viral-based expression systems can be utilized to express fusion proteins. Viral based expression systems are well known in the art and include, but are not limited to, baculoviral, SV40, retroviral, or vaccinia based viral vectors.

Mammalian cell lines that stably express proteins, polypeptides, fragments, variants or fusions thereof, can be produced using expression vectors with appropriate control elements and a selectable marker. For example, the eukaryotic expression vectors pCR3.1 (Invitrogen Life Technologies) and p91023(B) (see Wong et al. (1985) *Science* 228: 810-815) are suitable for expression of proteins, polypeptides, fragments, variants or fusions thereof, in, for example, Chinese hamster ovary (CHO) cells, COS-1 cells, human embryonic kidney 293 cells, NIH3T3 cells, BHK21 cells, MDCK cells, and human vascular endothelial cells (HUVEC). Additional suitable expression systems include the GS Gene Expression System™ available through Lonza Group Ltd.

Following introduction of an expression vector by electroporation, lipofection, calcium phosphate, or calcium chloride co-precipitation, DEAE dextran, or other suitable transfection method, stable cell lines can be selected (e.g., by metabolic selection, or antibiotic resistance to G418, kanamycin, or hygromycin). The transfected cells can be cultured such that the polypeptide of interest is expressed, and the polypeptide can be recovered from, for example, the cell culture supernatant or from lysed cells. Alternatively, a protein, polypeptide, fragment, variant or fusion thereof, can be produced by (a) ligating amplified sequences into a mammalian expression vector such as pcDNA3 (Invitrogen Life Technologies), and (b) transcribing and translating in vitro using wheat germ extract or rabbit reticulocyte lysate.

Proteins, polypeptides, fragments, variants or fusions thereof, can be isolated using, for example, chromatographic methods such as affinity chromatography, ion exchange chromatography, hydrophobic interaction chromatography, DEAE ion exchange, gel filtration, and hydroxylapatite chromatography. In some embodiments, Proteins, polypeptides, fragments, variants or fusions thereof can be engineered to contain an additional domain containing amino acid sequence that allows the polypeptides to be captured onto an affinity matrix. For example, an Fc-fusion polypeptide in a cell culture supernatant or a cytoplasmic extract can be isolated using a protein A column. In addition, a tag such as c-myc, hemagglutinin, polyhistidine, or Flag™ (Kodak) can be used to aid polypeptide purification. Such tags can be inserted anywhere within the polypeptide, including at either the carboxyl or amino terminus. Other fusions that can be useful include enzymes that aid in the detection of the polypeptide, such as alkaline phosphatase. Immunoaffinity chromatography also can be used to purify polypeptides. Fusion proteins can additionally be engineered to contain a secretory signal (if there is not a secretory signal already present) that causes the Proteins, polypeptides, fragments, variants or fusions thereof to be secreted by the cells in which it is produced. The secreted Proteins, polypeptides, fragments, variants or fusions thereof can then conveniently be isolated from the cell media.

C. Methods for Producing Isolated Nucleic Acid Molecules

Isolated nucleic acid molecules can be produced by standard techniques, including, without limitation, common molecular cloning and chemical nucleic acid synthesis techniques. For example, polymerase chain reaction (PCR) techniques can be used to obtain an isolated nucleic acid encoding a variant polypeptide. PCR is a technique in which target nucleic acids are enzymatically amplified. Typically, sequence information from the ends of the region of interest or beyond can be employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292-1293.

Isolated nucleic acids can be chemically synthesized, either as a single nucleic acid molecule or as a series of oligonucleotides (e.g., using phosphoramidite technology for automated DNA synthesis in the 3' to 5' direction). For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase can be used to extend the oligonucleotides, resulting in a single, double-stranded nucleic acid molecule per oligonucleotide pair, which then can be ligated into a vector. Isolated nucleic acids can also obtained by mutagenesis. Protein-encoding nucleic acids can be mutated using standard techniques, including oligonucleotide-directed mutagenesis and/or site-directed mutagenesis through PCR. See, *Short Protocols in Molecular Biology*. Chapter 8, Green Publishing Associates and John Wiley & Sons, edited by Ausubel et al, 1992.

IV. Assays and Antibody Screening

Assays for Antibody Screening Include:
1. Analysis of binding affinity of B7-H4-Fc to ligands in comparison to B7-H4.
2. Functional assays to confirm B7-H4-Fc prevents signaling by B7-H4 expressing cells. Reporter cells may be utilized for these assays, or primary B7-H4+ cells are another option.

B7-H4 deficient ("knockout) mice or wild type mice can be utilized for the generation of high affinity mAbs against B7-H4 using proprietary immunization techniques. Autoimmune prone mice NZB/WF1 can be used to generate mAbs to overcome "tolerance".
1. Phase I screening: mAb binding to cell lines transfected to express cell surface B7-H4. Additionally, mAbs should have the capacity to bind endogenously expressed B7-H4 on the surface of primary human cell subsets. These mAbs should be highly specific for B7-H4. Antibodies can be screened using ELISA with purified B7-H4 protein to detect ant-B7-H4 antibodies.
2. Phase II screening: B7-H4 specific mAbs should block the binding of B7-H4 to its ligands and/or target cells.
3. Phase III screening: Functional assays to confirm that B7-H4 mAbs or combination of mAbs modulate B7-H4 signaling. These assays will utilize cell lines that express endogenous B7-H4, or primary cells such as human monocytes, macrophages and dendritic cell subsets to assess function in the presence of B7-H4 mAbs. Additionally, reporter cells lines may be used to determine if signaling pathways such as NFkB (NFkB reporter) or NFAT (NFAT reporter) are altered following culture with B7-H4 mAbs.
4. Phase IV screening: Functional assays to determine if B7-H4 mAbs are capable of inducing antibody dependent cell cytotoxicity (ADCC), complement dependent cytotoxicity (CDC) or cellular apoptosis through other mechanisms, of B7-H4 expressing cell lines. In particular, B7-H4 mAbs will be tested for the ability to deplete through one of these methods leukemia cell lines, known to express B7-H4 on the cell surface. B7-H4 mAbs may also be engineered to deplete B7-H4 expressing cells and tested as described later in this document through known methods.
5. Phase V screening: Functional assays to determine if B7-H4 mAbs are capable of delivering or inducing a negative signal (agonist) via B7-H4 into B7-H4 expressing cells to inhibit cellular function. Cell lines that endogenously express B7-H4, or transfectants of cell lines will be assessed for changes in phenotype and survival following culture with B7-H4 mAbs. In other assays, reporter cell lines will be used to determine in B7-H4 mAbs modulate positive signaling pathways such as NF-kB (NF-kB reporter) or other known cell signaling reporters. Induction of apoptosis in cell lines will be also be evaluated.

Phase II and III assays can be used to predict the concentrations of B7-H4 mAb(s) required to block physiological levels of ligands in vivo.

V. Method of Use

Antagonists or agonists of B7-H4 can be used to modulate immune responses in subjects in need of such treatment.

Exemplary methods are discussed in more detail below.

A. Immune Response Stimulation

1. Therapeutic Strategies

Methods of inducing or enhancing an immune response in a subject are provided. Typically, the methods include administering a subject an effective amount of immunomodulatory agent, or cells primed ex vivo with the immunomodulatory agent. The immune response can be, for example, a primary immune response to an antigen or an increase effector cell function such as increasing antigen-specific proliferation of T cells, enhancing cytokine production by T cells, stimulating differentiation, or a combination thereof. In some embodiments, the agent can increase the development of naïve T cells into Th1, Th17, Th22, or other cells that secrete, or cause other cells to secrete, inflammatory molecules, including, but not limited to, IL-10, TNF-α, TGF-beta, IFN-γ, IL-17, IL-6, IL-23, IL-22, IL-21, and MMPs. In some embodiments, the agent can reduce or inhibit the activity of Tregs, reduce the production of cytokines such as IL-10 from Tregs, reduce the differentiation of Tregs, reduce the number of Tregs, reduce the ratio of Tregs within an immune cell population, or reduce the survival of Tregs. The immunomodulatory agent can be administered to a subject in need thereof in an effective amount to overcome T cell exhaustion and/or T cell anergy. Overcoming T cell exhaustion or T cell anergy can be determined by measuring T cell function using known techniques.

The methods can be used in vivo or ex vivo as immune response-stimulating therapeutic applications. Thus in some embodiments, the agent, or nucleic acid encoding the agent, is administered directly to the subject. In some embodiments, the agent or nucleic acid encoding the agent, is contacted with cells (e.g., immune cells) ex vivo, and the treat cells are administered to the subject (e.g. adoptive transfer). In general, the disclosed immunomodulatory agents can be used for treating a subject having or being predisposed to any disease or disorder to which the subject's immune system mounts an immune response. The agents can enable a more robust immune response to be possible. The disclosed compositions are useful to stimulate or enhance immune responses involving T cells.

The immunomodulatory agents utilized for increasing an immune response are typically those that reduce B7-H4 expression, ligand binding, crosslinking, negative signaling, or a combination thereof. For example, the agent can be an antagonist of B7-H4, such as an antagonist (blocking) anti-B7-H4 antibody or antigen binding fragment thereof. The agent can also be a B7-H4 polypeptide, for example, a soluble polypeptide, or fusion protein thereof that can serve as a decoy receptor for one or more B7-H4 ligands or receptors.

B7-H4 blockade, for example using function blocking anti-B7-H4 antibodies, can be an alternative agent or complementary agent to soluble B7-H4 polypeptides and fusion proteins. For example, in some embodiments, B7-H4 blockade is combined with a decoy receptor such as soluble B7-H4 or fusion protein thereof. The combined treatment (e.g., B7-H4-Fc and B7-H4 blockade) may be complementary.

In some embodiments, immune response stimulating therapy (e.g., in the treatment of cancer or infections) includes depletion of B7-H4+ cells.

Development and identification of B7-H4 depleting mAbs can be carried out according to known construction and screening methods including those discussed herein. See, for example, Reff, et al, Blood. Vol83, No 2, 1994: pp 435-445, which describes preparation of an anti-CD20 chimeric antibody that binds to human C1q, and mediates complement-dependent cell lysis (CDCC) in the presence of human complement, and anti-body-dependent cellular cytotoxicity (ADCC) with human effector cells. Rituximab destroys B cells and is therefore used to treat diseases which are characterized by overactive, dysfunctional, or excessive numbers of B cells. Other B cell-depleting antibodies include ocrelizumab and ofatumumab. In another example, CD3 Abs can preferentially target and deplete activated effector T cells while preserving CD4$^+$Foxp3$^+$ Tregs. The antibodies transiently deplete T cells although they display no or little complement-dependent and antibody-dependent cellular cytotoxicity. Redirected cell lysis due to the ability to crosslink CD3 molecules expressed by two different cells (cytotoxic CD8+ T cells on one side and other target T cells on the other side) has been shown, however, T cell depletion mostly results from AICD (reviewed in You, *Front Immunol.* 2015; 6: 242).

A subject in need of enhancing their immune response can be administered with an agent that inhibits or blocks B7-H4 suppressive immune response in an amount effective to increase the uptake of antigen by antigen presenting cells (APCs).

2. Subjects to be Treated a. Treatment of Cancer

The disclosed compositions and methods can be used to treat cancer. Generally, the agents are used to stimulate or enhance an immune response to cancer in the subject by administering to the subject an amount of an immunomodulatory agent that reduces B7-H4 expression, ligand binding, crosslinking, negative signaling, or a combination thereof. Cancer cells acquire a characteristic set of functional capabilities during their development, albeit through various mechanisms. Such capabilities include evading apoptosis, self-sufficiency in growth signals, insensitivity to anti-growth signals, tissue invasion/metastasis, limitless replicative potential, and sustained angiogenesis. The term "cancer cell" is meant to encompass both pre-malignant and malignant cancer cells. In some embodiments, cancer refers to a benign tumor, which has remained localized. In other embodiments, cancer refers to a malignant tumor, which has invaded and destroyed neighboring body structures and spread to distant sites. In yet other embodiments, the cancer is associated with a specific cancer antigen (e.g., pan-carcinoma antigen (KS ¼), ovarian carcinoma antigen (CA125), prostate specific antigen (PSA), carcinoembryonic antigen (CEA), CD19, CD20, HER2/neu, etc.).

The methods and compositions disclosed herein are useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xenoderma pegmentosum, keratoactanthoma, seminoma, thyroid follicular cancer and teratocarcinoma.

Cancers caused by aberrations in apoptosis can also be treated by the disclosed methods and compositions. Such cancers may include, but are not be limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions in the ovary, bladder, breast, colon, lung, skin, pancreas, or uterus. In other specific embodiments, sarcoma, melanoma, or leukemia is treated or prevented by the methods and compositions.

The disclosed compositions and methods are particularly useful for the treatment of cancers that are associated with cells that express abnormally high levels of B7-H4.

Specific cancers and related disorders that can be treated or prevented by methods and compositions disclosed herein include, but are not limited to, leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as, but not limited to, Hodgkin's disease or non-Hodgkin's disease lymphomas (e.g., diffuse anaplastic lymphoma kinase (ALK) negative, large B-cell lymphoma (DLBCL); diffuse anaplastic lymphoma kinase (ALK) positive, large B-cell lymphoma (DLBCL); anaplastic lymphoma kinase (ALK) positive, ALK+anaplastic large-cell lymphoma (ALCL), acute myeloid lymphoma (AML)); multiple myelomas such as, but not limited to, smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including, but not limited to, ocular melanoma such as iris melanoma, choroidal melanoma, and ciliary body melanoma, and retinoblastoma; vaginal cancers, including, but not limited to, squamous cell carcinoma, adenocarcinoma, and melanoma;

vulvar cancer, including but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or ureter); Wilms' tumor; bladder cancers including, but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

b. Treatment of Infections

The disclosed compositions and methods can be used to treat infections and infectious diseases. Generally, the agents are used to stimulate or enhance an immune response to infection causing agent in the subject by administering to the subject an amount of an immunomodulatory agent that reduces B7-H4 expression, ligand binding, crosslinking, negative signaling, or a combination thereof. The method can reduce one or more symptoms of the infection.

Neutrophils are a major component of the host innate defense against infection and also contribute to autoimmune pathogenesis and chronic inflammation. During infection, neutrophils rapidly migrate to sites of inflammation, become activated, and initiate a cascade of defense mechanisms including phagocytosis, killing, and degradation of microorganisms by antimicrobial and proteolytic proteins, along with the generation of reactive oxygen species. Neutrophils also participate in tissue breakdown, remodeling, wound healing, and modulation of other inflammatory and adaptive immune components. Due to their short life span, neutrophils have to be resupplied continuously during infection and inflammation by expansion from myeloid progenitor cells in the bone marrow. In vitro B7-H4 inhibits the growth of bone marrow-derived neutrophil progenitors, suggesting an inhibitory function of B7-H4 in neutrophil expansion (Zhu, G. et al., Blood, 113:1759-1767 (2009)).

One embodiment provides a method for treating infection in a subject in need thereof by administering an effective amount of an agent that inhibits or blocks B7-H4 suppressive immune response in an amount effective to expand neutrophils and/or increase innate immunity.

The infection or disease can be caused by a bacterium, virus, protozoan, helminth, or other microbial pathogen that enters intracellularly and is attacked, i.e., by cytotoxic T lymphocytes.

The infection or disease can be acute or chronic. An acute infection is typically an infection of short duration. During an acute microbial infection, immune cells begin expressing immunomodulatory receptors. Accordingly, in some embodiments, the method includes increasing an immune stimulatory response against an acute infection.

The infection can be caused by, for example, but not limited to *Candida albicans, Listeria monocytogenes, Streptococcus pyogenes, Streptococcus pneumoniae, Neisseria meningitidis, Staphylococcus aureus, Escherichia coli, Acinetobacter baumannii, Pseudomonas aeruginosa* or *Mycobacterium*.

In some embodiments, the disclosed compositions are used to treat chronic infections, for example infections in which T cell exhaustion or T cell anergy has occurred causing the infection to remain with the host over a prolonged period of time.

Exemplary infections to be treated are chronic infections cause by a hepatitis virus, a human immunodeficiency virus (HIV), a human T-lymphotrophic virus (HTLV), a herpes virus, an Epstein-Barr virus, or a human papilloma virus.

Because viral infections are cleared primarily by T cells, an increase in T-cell activity would be therapeutically useful in situations where more rapid or thorough clearance of an infective viral agent would be beneficial to an animal or human subject. Thus, the disclosed compositions can be administered for the treatment of local or systemic viral infections, including, but not limited to, immunodeficiency (e.g., HIV), papilloma (e.g., HPV), herpes (e.g., HSV), encephalitis, influenza (e.g., human influenza virus A), and common cold (e.g., human rhinovirus) and other viral infections, caused by, for example, HTLV, hepatitis virus, respiratory syncytial virus, vaccinia virus, and rabies virus. The molecules can be administered topically to treat viral skin diseases such as herpes lesions or shingles, or genital warts. The molecules can also be administered systemically to treat systemic viral diseases, including, but not limited to, AIDS, influenza, the common cold, or encephalitis.

Representative infections that can be treated, include but are not limited to infections cause by microorganisms including, but not limited to, *Actinomyces, Anabaena, Bacillus, Bacteroides, Bdellovibrio, Bordetella, Borrelia, Campylobacter, Caulobacter, Chlamydia, Chlorobium, Chroma-*

*tium, Clostridium, Corynebacterium, Cytophaga, Deinococcus, Escherichia, Francisella, Halobacterium, Heliobacter, Haemophilus, Hemophilus* influenza type B(HIB), *Hyphomicrobium, Legionella, Leptspirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus,* and *Treponema, Vibrio, Yersinia, Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni.*

Other microorganisms that can be treated using the disclosed compositions and methods include, bacteria, such as those of *Klebsiella, Serratia, Pasteurella*; pathogens associated with cholera, tetanus, botulism, anthrax, plague, and Lyme disease; or fungal or parasitic pathogens, such as *Candida* (*albicans, krusei, glabrata, tropicalis*, etc.), *Cryptococcus, Aspergillus* (*fumigatus, niger*, etc.), Genus *Mucorales* (*mucor, absidia, rhizophus*), *Sporothrix* (*schenkii*), *Blastomyces* (*dermatitidis*), *Paracoccidioides* (*brasiliensis*), *Coccidioides* (*immitis*) and *Histoplasma* (*capsulatuma*), *Entamoeba, histolytica, Balantidium coli, Naegleria fowleri, Acanthamoeba* sp., *Giardia Zambia, Cryptosporidium* sp., *Pneumocystis carinii, Plasmodium vivax, Babesia microti, Trypanosoma brucei, Trypanosoma cruzi, Toxoplasma gondi*, etc.), *Sporothrix, Blastomyces, Paracoccidioides, Coccidioides, Histoplasma, Entamoeba, Histolytica, Balantidium, Naegleria, Acanthamoeba, Giardia, Cryptosporidium, Pneumocystis, Plasmodium, Babesia,* or *Trypanosoma,* etc.

B. Immune Response Inhibition

1. Therapeutic Strategies

Methods of reducing or inhibiting an immune response in a subject are provided. Typically the methods include administering a subject an effective amount of immunomodulatory agent, or cells primed ex vivo with the immunomodulatory agent. The immune response can be, for example, a primary immune response to an antigen or an increase effector cell function such as increasing antigen-specific proliferation of T cells, enhancing cytokine production by T cells, stimulating differentiation, or a combination thereof. Thus in some embodiments, the agent reduces T cell proliferation, T cell cytokine production, T cell differentiation, or a combination thereof. In some embodiments, the agent can reduce the development of naïve T cells into Th1, Th17, Th22, or other cells that secrete, or cause other cells to secrete, inflammatory molecules, including, but not limited to, IL-1β, TNF-α, TGF-beta, IFN-γ, IL-17, IL-6, IL-23, IL-22, IL-21, and MMPs. In some embodiments, the agent can increase or promote the activity of Tregs, increase the production of cytokines such as IL-10 from Tregs, increase the differentiation of Tregs, increase the number of Tregs, increase the ratio of Tregs within an immune cell population, or increase the survival of Tregs.

The methods can be used in vivo or ex vivo as immune response-inhibiting therapeutic applications. Thus in some embodiments, the agent, or nucleic acid encoding the agent, is administered directly to the subject. In some embodiments, the agent or nucleic acid encoding the agent, is contacted with cells (e.g., immune cells) ex vivo, and the treat cells are administered to the subject (e.g. adoptive transfer). In general, the disclosed immunomodulatory agents can be used for treating a subject having or being predisposed to any disease or disorder to which the subject's immune system mounts an overactive or inappropriate immune response. The agents can enable a less robust immune response to be possible. The disclosed compositions are useful to reduce or inhibit immune responses involving T cells.

The immunomodulatory agents utilized for reducing an immune response are typically those that increase B7-H4 expression, ligand binding, crosslinking, negative signaling, or a combination thereof. For example, the agent can be an agonist of B7-H4, such as an agonist (stimulating) anti-B7-H4 antibody or antigen binding fragment thereof.

a. Inflammatory Responses

The disclosed compositions and methods can be used to treat inflammation. Generally, the agents are used to reduce or inhibit an immune response in the subject by administering to the subject an amount of an immunomodulatory agent that increases B7-H4 expression, ligand binding, crosslinking, negative signaling, or a combination thereof. The method can reduce or more symptoms of the inflammation. In inflammation can be acute, chronic, or persistent inflammation.

In some embodiments, the immunomodulatory agents slow down the immune system. For example, agent can be used to control hyper-inflammatory response causing damage healthy tissues. Accordingly, in some embodiments, the agents are administered to a subject undergoing a hyper-inflammatory response. In such cases, controlling excessive immune responses can be beneficial to the subject.

b. Inflammatory and Autoimmune Diseases/Disorders

Agents that increase B7-H4 expression, ligand binding, crosslinking, negative signaling, or a combination thereof can also be used to treat inflammatory or autoimmune diseases and disorders. Representative inflammatory or autoimmune diseases/disorders include, but are not limited to, rheumatoid arthritis, systemic lupus erythematosus, alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Behcet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis—juvenile, discoid lupus, essential mixed cryoglobulinemia, fibromyalgia—fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis *nodosa*, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

In some embodiments the inflammation or autoimmune disease is caused by a pathogen, or is the result of an infection.

VI. Combination Therapies

The disclosed immunomodulatory agents can be administered to a subject in need thereof alone or in combination with one or more additional therapeutic agents. In some embodiments, the immunomodulatory agent and the additional therapeutic agent are administered separately, but simultaneously. The immunomodulatory agent and the additional therapeutic agent can also be administered as part of the same composition. In other embodiments, the immunomodulatory agent and the second therapeutic agent are administered separately and at different times, but as part of the same treatment regime.

The subject can be administered a first therapeutic agent 1, 2, 3, 4, 5, 6, or more hours, or 1, 2, 3, 4, 5, 6, 7, or more days before administration of a second therapeutic agent. In some embodiments, the subject can be administered one or more doses of the first agent every 1, 2, 3, 4, 5, 6 7, 14, 21, 28, 35, or 48 days prior to a first administration of second agent. The immunomodulatory agent can be the first or the second therapeutic agent.

The immunomodulatory agent and the additional therapeutic agent can be administered as part of a therapeutic regimen. For example, if a first therapeutic agent can be administered to a subject every fourth day, the second therapeutic agent can be administered on the first, second, third, or fourth day, or combinations thereof. The first therapeutic agent or second therapeutic agent may be repeatedly administered throughout the entire treatment regimen.

Exemplary molecules include, but are not limited to, cytokines, chemotherapeutic agents, radionuclides, other immunotherapeutics, enzymes, antibiotics, antivirals (especially protease inhibitors alone or in combination with nucleosides for treatment of HIV or Hepatitis B or C), anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, ligands that bind to Toll-Like Receptors (including but not limited to CpG oligonucleotides) to activate the innate immune system, molecules that mobilize and optimize the adaptive immune system, other molecules that activate or up-regulate the action of cytotoxic T lymphocytes, natural killer cells and helper T-cells, and other molecules that deactivate or down-regulate suppressor or regulatory T-cells.

The additional therapeutic agents are selected based on the condition, disorder or disease to be treated. For example, the immunomodulatory agent can be co-administered with one or more additional agents that function to enhance or promote an immune response or reduce or inhibit an immune response.

A. Increasing Immune Responses
1. Antimicrobials

For example, a B7-H4 immunomodulatory agent can be used in a preventive or prophylactic role in the treatment and prevention of disease as discussed above, and also in the context of severe trauma injuries like major burn, open bone fracture, accidental amputation or other wounds. Therefore, the B7-H4 immunomodulatory agents can be administered to the subject in combination with an antimicrobial such as an antibiotic, an antifungal, an antiviral, an antiparasitics, or essential oil.

In some embodiments, the subject is administered the B7-H4 immunomodulatory agent and/or the antimicrobial at time of admission to the hospital to prevent further bacterial, fungal or viral complications. The antibiotic can target pathogens and the B7-H4 immunomodulatory agent can stimulate the immune system to provide an enhanced response to treat or prevent further infection or disease.

2. Chemotherapeutic Agents

The B7-H4 immunomodulatory agents can be combined with one or more chemotherapeutic agents and pro-apoptotic agents. Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ (2) and combinations thereof.

3. Other Immunomodulators
a. PD-1 antagonists

In some embodiments, B7-H4 immunomodulatory agents are co-administered with a PD-1 antagonist. Programmed Death-1 (PD-1) is a member of the CD28 family of receptors that delivers a negative immune response when induced on T cells. Contact between PD-1 and one of its ligands (B7-H1 or B7-DC) induces an inhibitory response that decreases T cell multiplication and/or the strength and/or duration of a T cell response. Suitable PD-1 antagonists are described in U.S. Pat. Nos. 8,114,845, 8,609,089, and 8,709,416, which are specifically incorporated by reference herein in their entities, and include compounds or agents that either bind to and block a ligand of PD-1 to interfere with or inhibit the binding of the ligand to the PD-1 receptor, or bind directly to and block the PD-1 receptor without inducing inhibitory signal transduction through the PD-1 receptor.

In some embodiments, the PD-1 receptor antagonist binds directly to the PD-1 receptor without triggering inhibitory signal transduction and also binds to a ligand of the PD-1 receptor to reduce or inhibit the ligand from triggering signal transduction through the PD-1 receptor. By reducing the number and/or amount of ligands that bind to PD-1 receptor and trigger the transduction of an inhibitory signal, fewer cells are attenuated by the negative signal delivered by PD-1 signal transduction and a more robust immune response can be achieved.

It is believed that PD-1 signaling is driven by binding to a PD-1 ligand (such as B7-H1 or B7-DC) in close proximity to a peptide antigen presented by major histocompatibility complex (MHC) (see, for example, Freeman, *Proc. Natl. Acad. Sci. U.S.A*, 105:10275-10276 (2008)). Therefore, proteins, antibodies or small molecules that prevent co-ligation of PD-1 and TCR on the T cell membrane are also useful PD-1 antagonists.

In some embodiments, the PD-1 receptor antagonists are small molecule antagonists or antibodies that reduce or interfere with PD-1 receptor signal transduction by binding to ligands of PD-1 or to PD-1 itself, especially where co-ligation of PD-1 with TCR does not follow such binding, thereby not triggering inhibitory signal transduction through the PD-1 receptor. Other PD-1 antagonists contemplated by the methods of this invention include antibodies that bind to PD-1 or ligands of PD-1, and other antibodies.

Suitable anti-PD-1 antibodies include, but are not limited to, those described in the following publications:
PCT/IL03/00425 (Hardy et al., WO/2003/099196)
PCT/JP2006/309606 (Korman et al., WO/2006/121168)
PCT/US2008/008925 (Li et al., WO/2009/014708)
PCT/JP03/08420 (Honjo et al., WO/2004/004771)
PCT/JP04/00549 (Honjo et al., WO/2004/072286)
PCT/M2003/006304 (Collins et al., WO/2004/056875)
PCT/US2007/088851 (Ahmed et al., WO/2008/083174)
PCT/US2006/026046 (Korman et al., WO/2007/005874)
PCT/US2008/084923 (Terrett et al., WO/2009/073533)
Berger et al., *Clin. Cancer Res.*, 14:30443051 (2008).

A specific example of an anti-PD-1 antibody is an antibody described in Kosak, US 20070166281 (pub. 19 Jul. 2007) at par. 42), a human anti-PD-1 antibody, which in some embodiments is administered at a dose of 3 mg/kg.

Exemplary anti-B7-H1 antibodies include, but are not limited to, those described in the following publications:
PCT/US06/022423 (WO/2006/133396, pub. 14 Dec. 2006)
PCT/US07/088851 (WO/2008/083174, pub. 10 Jul. 2008)
US 2006/0110383 (pub. 25 May 2006)

A specific example of an anti-B7-H1 antibody is an antibody described (WO/2007/005874, published 11 Jan. 2007)), a human anti-B7-H1 antibody.

Additional anti-PD-1 and anti-B7-H1 antibodies are disclosed in 2014/0044738, which is specifically incorporated by reference herein in its entirety.

For anti-B7-DC antibodies see U.S. Pat. Nos. 7,411,051, 7,052,694, 7,390,888, and U.S. Published Application No. 2006/0099203.

Other exemplary PD-1 receptor antagonists include, but are not limited to B7-DC polypeptides, including homologs and variants of these, as well as active fragments of any of the foregoing, and fusion proteins that incorporate any of these. In some embodiments, the fusion protein includes the soluble portion of B7-DC coupled to the Fc portion of an antibody, such as human IgG, and does not incorporate all or part of the transmembrane portion of human B7-DC.

The PD-1 antagonist can also be a fragment of a mammalian B7-H1, for example from mouse or primate, such as a human, wherein the fragment binds to and blocks PD-1 but does not result in inhibitory signal transduction through PD-1. The fragments can also be part of a fusion protein, for example an Ig fusion protein.

Other useful polypeptides PD-1 antagonists include those that bind to the ligands of the PD-1 receptor. These include the PD-1 receptor protein, or soluble fragments thereof, which can bind to the PD-1 ligands, such as B7-H1 or B7-DC, and prevent binding to the endogenous PD-1 receptor, thereby preventing inhibitory signal transduction. B7-H1 has also been shown to bind the protein B7.1 (Butte et al., Immunity, Vol. 27, pp. 111-122, (2007)). Such fragments also include the soluble ECD portion of the PD-1 protein that includes mutations, such as the A99L mutation, that increases binding to the natural ligands (Molnar et al., *PNAS*, 105:10483-10488 (2008)). B7-1 or soluble fragments thereof, which can bind to the B7-H1 ligand and prevent binding to the endogenous PD-1 receptor, thereby preventing inhibitory signal transduction, are also useful.

PD-1 and B7-H1 anti-sense nucleic acids, both DNA and RNA, as well as siRNA molecules can also be PD-1 antagonists. Such anti-sense molecules prevent expression of PD-1 on T cells as well as production of T cell ligands, such as B7-H1, PD-L1 and/or PD-L2. For example, siRNA (for example, of about 21 nucleotides in length, which is specific for the gene encoding PD-1, or encoding a PD-1 ligand, and which oligonucleotides can be readily purchased commercially) complexed with carriers, such as polyethyleneimine (see Cubillos-Ruiz et al., J. Clin. Invest. 119(8): 2231-2244 (2009), are readily taken up by cells that express PD-1 as well as ligands of PD-1 and reduce expression of these receptors and ligands to achieve a decrease in inhibitory signal transduction in T cells, thereby activating T cells.

b. CTLA4 Antagonists

Other molecules useful in mediating the effects of T cells in an immune response are also contemplated as additional therapeutic agents. In some embodiments, the molecule is an antagonist of CTLA4, for example an antagonistic anti-CTLA4 antibody. An example of an anti-CTLA4 antibody contemplated for use in the methods of the invention includes an antibody as described in PCT/US2006/043690 (Fischkoff et al., WO/2007/056539).

Dosages for anti-PD-1, anti-B7-H1, and anti-CTLA4 antibody, are known in the art and can be in the range of, for example, 0.1 to 100 mg/kg, or with shorter ranges of 1 to 50 mg/kg, or 10 to 20 mg/kg. An appropriate dose for a human subject can be between 5 and 15 mg/kg, with 10 mg/kg of antibody (for example, human anti-PD-1 antibody) being a specific embodiment.

Specific examples of an anti-CTLA4 antibody useful in the methods of the invention are Ipilimumab, a human anti-CTLA4 antibody, administered at a dose of, for example, about 10 mg/kg, and Tremelimumab a human anti-CTLA4 antibody, administered at a dose of, for example, about 15 mg/kg. See also Sammartino, et al., *Clinical Kidney Journal*, 3(2):135-137 (2010), published online December 2009.

In other embodiments, the antagonist is a small molecule. A series of small organic compounds have been shown to bind to the B7-1 ligand to prevent binding to CTLA4 (see Erbe et al., *J. Biol. Chem.*, 277:7363-7368 (2002). Such small organics could be administered alone or together with an anti-CTLA4 antibody to reduce inhibitory signal transduction of T cells.

4. Potentiating Agents

In some embodiments, additional therapeutic agents include a potentiating agent. The potentiating agent acts to increase efficacy the immune response up-regulator, possibly by more than one mechanism, although the precise mechanism of action is not essential to the broad practice of the present invention.

In some embodiments, the potentiating agent is cyclophosphamide. Cyclophosphamide (CTX, Cytoxan®, or Neosar®) is an oxazahosphorine drug and analogs include ifosfamide (IFO, Ifex), perfosfamide, trophosphamide (trofosfamide; Ixoten), and pharmaceutically acceptable salts, solvates, prodrugs and metabolites thereof (US patent application 20070202077 which is incorporated in its entirety). Ifosfamide (MITOXANA®) is a structural analog of cyclophosphamide and its mechanism of action is considered to be identical or substantially similar to that of cyclophosphamide. Perfosfamide (4-hydroperoxycyclophosphamide) and trophosphamide are also alkylating agents, which are structurally related to cyclophosphamide. For example, perfosfamide alkylates DNA, thereby inhibiting DNA replication and RNA and protein synthesis. New oxazaphosphorines derivatives have been designed and evaluated with an attempt to improve the selectivity and response with reduced host toxicity (Liang J, Huang M, Duan W, Yu X Q, Zhou S. Design of new oxazaphosphorine anticancer drugs. Curr Pharm Des. 2007; 13(9):963-78. Review). These include mafosfamide (NSC 345842), glufosfamide (D19575, beta- D-glucosylisophosphoramide mustard), S-(−)-bromofosfamide (CBM-11), NSC 612567 (aldophosphamide perhydrothiazine) and NSC 613060 (aldophosphamide thiazolidine). Mafosfamide is an oxazaphosphorine analog that is a chemically stable 4-thioethane sulfonic acid salt of 4-hydroxy-CPA. Glufosfamide is IFO derivative in which the isophosphoramide mustard, the alkylating metabolite of IFO, is glycosidically linked to a beta-D-glucose molecule. Additional cyclophosphamide analogs are described in U.S. Pat. No. 5,190,929 entitled "Cyclophosphamide analogs useful as anti-tumor agents" which is incorporated herein by reference in its entirety.

While CTX itself is nontoxic, some of its metabolites are cytotoxic alkylating agents that induce DNA crosslinking and, at higher doses, strand breaks. Many cells are resistant to CTX because they express high levels of the detoxifying enzyme aldehyde dehydrogenase (ALDH). CTX targets proliferating lymphocytes, as lymphocytes (but not hematopoietic stem cells) express only low levels of ALDH, and cycling cells are most sensitive to DNA alkylation agents.

Low doses of CTX (<200 mg/kg) can have immune stimulatory effects, including stimulation of anti-tumor immune responses in humans and mouse models of cancer (Brode & Cooke *Crit Rev. Immunol.* 28:109-126 (2008)). These low doses are sub-therapeutic and do not have a direct anti-tumor activity. In contrast, high doses of CTX inhibit the anti-tumor response. Several mechanisms may explain the role of CTX in potentiation of anti-tumor immune response: (a) depletion of CD4+CD25+FoxP3+ Treg (and specifically proliferating Treg, which may be especially suppressive), (b) depletion of B lymphocytes; (c) induction of nitric oxide (NO), resulting in suppression of tumor cell growth; (d) mobilization and expansion of CD11b+Gr-1+ MDSC. These primary effects have numerous secondary effects; for example following Treg depletion macrophages produce more IFN-γ and less IL-10. CTX has also been shown to induce type I IFN expression and promote homeostatic proliferation of lymphocytes.

Treg depletion is most often cited as the mechanism by which CTX potentiates the anti-tumor immune response. This conclusion is based in part by the results of adoptive transfer experiments. In the AB1-HA tumor model, CTX treatment at Day 9 gives a 75% cure rate. Transfer of purified Treg at Day 12 almost completely inhibited the CTX response (van der Most et al. *Cancer Immunol. Immunother.* 58:1219-1228 (2009). A similar result was observed in the HHD2 tumor model: adoptive transfer of CD4+CD25+ Treg after CTX pretreatment eliminated therapeutic response to vaccine (Taieb, J. *J. Immunol.* 176:2722-2729 (2006)).

Numerous human clinical trials have demonstrated that low dose CTX is a safe, well-tolerated, and effective agent for promoting anti-tumor immune responses (Bas, & Mastrangelo *Cancer Immunol. Immunother.* 47:1-12 (1998)).

The optimal dose for CTX to potentiate an anti-tumor immune response, is one that lowers overall T cell counts by lowering Treg levels below the normal range but is sub-therapeutic (see Machiels et al. Cancer Res. 61:3689-3697 (2001)).

In human clinical trials where CTX has been used as an immunopotentiating agent, a dose of 300 mg/m$^2$ has usually been used. For an average male (6 ft, 170 pound (78 kg) with a body surface area of 1.98 m$^2$), 300 mg/m$^2$ is 8 mg/kg, or 624 mg of total protein. In mouse models of cancer, efficacy has been seen at doses ranging from 15-150 mg/kg, which relates to 0.45-4.5 mg of total protein in a 30 g mouse (Machiels et al. *Cancer Res.* 61:3689-3697 (2001), Hengst et al *Cancer Res.* 41:2163-2167 (1981), Hengst *Cancer Res.* 40:2135-2141 (1980)).

For larger mammals, such as a primate, such as a human, patient, such mg/m$^2$ doses may be used but unit doses administered over a finite time interval may also be used. Such unit doses may be administered on a daily basis for a finite time period, such as up to 3 days, or up to 5 days, or up to 7 days, or up to 10 days, or up to 15 days or up to 20 days or up to 25 days, are all specifically contemplated by the invention. The same regimen may be applied for the other potentiating agents recited herein.

In other embodiments, the potentiating agent is an agent that reduces activity and/or number of regulatory T lymphocytes (T-regs), such as Sunitinib)(SUTENT®, anti-TGFβ or Imatinib)(GLEEVAC®). The recited treatment regimen may also include administering an adjuvant.

Useful potentiating agents also include mitosis inhibitors, such as paclitaxol, aromatase inhibitors (e.g. Letrozole) and angiogenesis inhibitors (VEGF inhibitors e.g. Avastin, VEGF-Trap) (see, for example, Li et al., Vascular endothelial growth factor blockade reduces intratumoral regulatory T cells and enhances the efficacy of a GM-CSF-secreting cancer immunotherapy. Clin Cancer Res. 2006 Nov. 15; 12(22):6808-16.), anthracyclines, oxaliplatin, doxorubicin, TLR4 antagonists, and IL-18 antagonists.

B. Reducing Immune Responses

1. Immunosuppressive Agents

In some embodiments, the immune response, or inflammatory/autoimmune disease/disorder is treated by administering to the subject a B7-H4 immunomodulatory agent and a second agent that is an immune suppressant. Immunosuppressive agents include, but are not limited to antibodies against other lymphocyte surface markers (e.g., CD40, alpha-4 integrin) or against cytokines), fusion proteins (e.g., CTLA-4-Ig (Orencia®), TNFR-Ig (Enbrel®)), TNF-α blockers such as Enbrel, Remicade, Cimzia and Humira, cyclophosphamide (CTX) (i.e., Endoxan®, Cytoxan®, Neosar®, Procytox®, Revimmune™), methotrexate (MTX) (i.e., Rheumatrex®, Trexall®), belimumab (i.e., Benlysta®), or other immunosuppressive drugs (e.g., cyclosporin A, FK506-like compounds, rapamycin compounds, or steroids), anti-proliferatives, cytotoxic agents, or other compounds that may assist in immunosuppression.

The therapeutic agent can be a CTLA-4 fusion protein, such as CTLA-4-Ig (abatacept). CTLA-4-Ig fusion proteins compete with the co-stimulatory receptor, CD28, on T cells for binding to CD80/CD86 (B7-1/B7-2) on antigen presenting cells, and thus function to inhibit T cell activation. In another embodiment, the therapeutic agent is a CTLA-4-Ig fusion protein known as belatacept. Belatacept contains two amino acid substitutions (L104E and A29Y) that markedly increase its avidity to CD86 in vivo. In another embodiment, the therapeutic agent is Maxy-4.

In another embodiment, the therapeutic agent is cyclophosphamide (CTX). Cyclophosphamide (the generic name for Endoxan®, Cytoxan®, Neosar®, Procytox®, Revimmune™), also known as cytophosphane, is a nitrogen mustard alkylating agent from the oxazophorines group. It is used to treat various types of cancer and some autoimmune disorders. Cyclophosphamide (CTX) is the primary drug used for diffuse proliferative glomerulonephritis in patients with renal lupus.

The therapeutic agent can be administered in an effective amount to reduce the blood or serum levels of anti-double stranded DNA (anti-ds DNA) auto antibodies and/or to reduce proteinuria in a patient in need thereof.

In another embodiment, the therapeutic agent increases the amount of adenosine in the serum, see for example, WO 08/147482. For example, the second therapeutic agent can be CD73-Ig, recombinant CD73, or another agent (e.g., a cytokine or monoclonal antibody or small molecule) that increases the expression of CD73, see for example WO 04/084933. In another embodiment the therapeutic agent is Interferon-beta.

The therapeutic agent can be a small molecule that inhibits or reduces differentiation, proliferation, activity, and/or cytokine production and/or secretion by Th1, Th17, Th22, and/or other cells that secrete, or cause other cells to secrete, inflammatory molecules, including, but not limited to, IL-10, TNF-$\alpha$, TGF-beta, IFN-$\gamma$, IL-18 IL-17, IL-6, IL-23, IL-22, IL-21, and MMPs. In another embodiment, the therapeutic agent is a small molecule that interacts with Tregs, enhances Treg activity, promotes or enhances IL-10 secretion by Tregs, increases the number of Tregs, increases the suppressive capacity of Tregs, or combinations thereof.

In some embodiments, the composition increases Treg activity or production. Exemplary Treg enhancing agents include but are not limited to glucocorticoid fluticasone, salmeteroal, antibodies to IL-12, IFN-$\gamma$, and IL-4; vitamin D3, and dexamethasone, and combinations thereof.

In some embodiments, the therapeutic agent is an antibody, for example, a functions blocking antibody against a proinflammatory molecule such as IL-6, IL-23, IL-22 or IL-21.

As used herein the term "rapamycin compound" includes the neutral tricyclic compound rapamycin, rapamycin derivatives, rapamycin analogs, and other macrolide compounds which are thought to have the same mechanism of action as rapamycin (e.g., inhibition of cytokine function). The language "rapamycin compounds" includes compounds with structural similarity to rapamycin, e.g., compounds with a similar macrocyclic structure, which have been modified to enhance their therapeutic effectiveness. Exemplary Rapamycin compounds are known in the art (See, e.g. WO95122972, WO 95116691, WO 95104738, U.S. Pat. Nos. 6,015,809; 5,989,591; 5,567,709; 5,559,112; 5,530,006; 5,484,790; 5,385,908; 5,202,332; 5,162,333; 5,780,462; 5,120,727).

The language "FK506-like compounds" includes FK506, and FK506 derivatives and analogs, e.g., compounds with structural similarity to FK506, e.g., compounds with a similar macrocyclic structure which have been modified to enhance their therapeutic effectiveness. Examples of FK506-like compounds include, for example, those described in WO 00101385. In some embodiments, the language "rapamycin compound" as used herein does not include FK506-like compounds.

2. Anti-inflammatories

Other suitable therapeutic agents include, but are not limited to, anti-inflammatory agents. The anti-inflammatory agent can be non-steroidal, steroidal, or a combination thereof. One embodiment provides oral compositions containing about 1% (w/w) to about 5% (w/w), typically about 2.5% (w/w) or an anti-inflammatory agent. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chloroprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

VII. Kits

The disclosed B7-H4 immunomodulatory agents can be packaged in a hermetically sealed container, such as an ampoule or sachette, indicating the quantity. The agent can be supplied as a dry sterilized lyophilized powder or water free concentrate in a hermetically sealed container and can be reconstituted, e.g., with water or saline to the appropriate concentration for administration to a subject. For example, the agent can be supplied as a dry sterile lyophilized powder in a hermetically sealed container at a unit dosage of at least 5 mg, or at least 10 mg, at least 15 mg, at least 25 mg, at least 35 mg, at least 45 mg, at least 50 mg, or at least 75 mg. The lyophilized agent can be stored at between 2 and 8° C. in their original container and are typically administered within 12 hours, or within 6 hours, or within 5 hours, or within 3 hours, or within 1 hour after being reconstituted.

In an alternative embodiment, the agent can be supplied in liquid form in a hermetically sealed container indicating the quantity and concentration. In some embodiments, the liquid form of the agent can be supplied in a hermetically sealed container including at least 1 mg/ml, or at least 2.5 mg/ml, at least 5 mg/ml, at least 8 mg/ml, at least 10 mg/ml, at least 15 mg/ml, at least 25 mg/ml, at least 50 mg/ml, at least 100 mg/ml, at least 150 mg/ml, at least 200 mg/ml of the agent.

Pharmaceutical packs and kits including one or more containers filled with agent are also provided. Additionally, one or more other prophylactic or therapeutic agents useful for the treatment of a disease can also be included in the pharmaceutical pack or kit. The pharmaceutical pack or kit can also include one or more containers filled with one or more of the ingredients of the disclosed pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration.

Kits designed for the above-described methods are also provided. Embodiments typically include one or more B7-H4 immunomodulatory agents. In particular embodiments, a kit also includes one or more other prophylactic or therapeutic agents useful for the treatment of cancer, in one or more containers. In other embodiments, a kit also includes one or more anti-inflammatory agents useful for the treatment inflammatory and autoimmune diseases, in one or more containers.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

---

We claim:

1. An anti-B7H4 antibody or antigen binding fragment thereof comprising a light chain having an amino acid sequence according to SEQ ID NO: 63 and a heavy chain having an amino acid sequence according to SEQ ID NO: 81.

2. A pharmaceutical composition comprising an effective amount of an immunomodulatory agent that reduces B7-H4 expression, ligand binding, crosslinking, negative signaling, or a combination thereof consisting of the anti-B7-H4 antibody or antigen binding fragment of claim 1 to increase an immune response in a subject in need thereof.

3. A vector comprising a nucleic acid sequence or nucleic acid sequences encoding an antibody or antigen binding fragment thereof of claim 1.

4. A host cell comprising a nucleic acid sequence or a vector according to claim 3.

5. A method of increasing an immune response in a subject in need thereof comprising administering to the subject the pharmaceutical composition of—claim 2.

6. The method of claim 5, wherein the subject has cancer characterized by increased expression of B7-H4.

7. The method of claim 6, wherein the cancer is ovarian cancer.

8. The method of claim 5, wherein the subject is contemporaneously administered with a vaccine or a component thereof.

9. The method of claim 5, further comprising administering to the subject a second therapeutic agent.

10. A pharmaceutical composition comprising an effective amount of an immunomodulatory agent that increases B7-H4 expression, ligand binding, crosslinking, negative signaling, or a combination thereof selected from the group consisting of the anti-B7-H4 antibody or antigen of claim 1, to decrease an immune response in a subject in need thereof.

11. A method of reducing an immune response in a subject in need thereof comprising administering to the subject the pharmaceutical composition of claim 10.

12. The method of claim 11, wherein the subject has inflammation.

13. The method of claim 11, wherein the subject has an autoimmune disorder.

14. The method of claim 13, wherein the autoimmune disorder is rheumatoid arthritis.

15. The method of any one of claim 11, wherein the subject or a disease or condition characterized reduced expression of B7-H4.

16. The method of any one of claim 11, further comprising administering to the subject a second therapeutic agent.

* * * * *